United States Patent
Aalamifar

(10) Patent No.: US 12,033,316 B2
(45) Date of Patent: Jul. 9, 2024

(54) SYSTEMS AND METHODS OF MEASURING THE BODY BASED ON IMAGE ANALYSIS

(71) Applicant: PediaMetrix Inc., Rockville, MD (US)

(72) Inventor: Fereshteh Aalamifar, Rockville, MD (US)

(73) Assignee: PediaMetrix Inc., Rockville, MD (US)

(*) Notice: Subject to any disclaimer, the term of this patent is extended or adjusted under 35 U.S.C. 154(b) by 489 days.

(21) Appl. No.: 16/982,900

(22) PCT Filed: Mar. 25, 2019

(86) PCT No.: PCT/US2019/023843
§ 371 (c)(1),
(2) Date: Sep. 21, 2020

(87) PCT Pub. No.: WO2019/190968
PCT Pub. Date: Oct. 3, 2019

(65) Prior Publication Data
US 2021/0004957 A1 Jan. 7, 2021

Related U.S. Application Data

(60) Provisional application No. 62/647,884, filed on Mar. 26, 2018.

(51) Int. Cl.
*G06T 7/00* (2017.01)
*A61B 5/107* (2006.01)
(Continued)

(52) U.S. Cl.
CPC .......... *G06T 7/0012* (2013.01); *A61B 5/1079* (2013.01); *G06T 7/10* (2017.01);
(Continued)

(58) Field of Classification Search
CPC .......... G06T 7/0012; G06T 7/10; G06T 7/60; G06T 2207/30004; G06T 7/0016;
(Continued)

(56) References Cited

U.S. PATENT DOCUMENTS 5,917,929 A 6/1999 Marshall et al.
6,834,207 B2 12/2004 Miyauchi et al.
(Continued)

FOREIGN PATENT DOCUMENTS

CN 201505136 U 6/2010
CN 106960461 A * 7/2017
(Continued)

OTHER PUBLICATIONS

Barbero-Garcia et al. "Low-Cost Smartphone-Based Photogrammetry for the Analysis of Cranial Deformation in Infants." World Neurosurgery, vol. 102, Jun. 2017, pp. 545-554 (Year: 2017).*
(Continued)

*Primary Examiner* — Jon Chang
(74) *Attorney, Agent, or Firm* — Oblon, McClelland, Maier & Neustadt, L.L.P.

(57) ABSTRACT

The present disclosure is generally related to systems and methods that can be implemented in a mobile application to allow users, such as parents and care providers, to measure and monitor, for example, a patient's body including an infant's head shape, at the point of care. The point of care can be, for instance, the home environment, a doctor's office, or a hospital setting. After acquiring 2D and/or 3D images of the body part, parameters reflecting potential deformity can be calculated. If abnormal measurements are determined, the user can be guided through therapeutic options to improve the condition. Based on the severity of the condition, different recommendations can be provided. Moreover, longitudinal monitoring and evaluation of the parameters can be performed. Monitoring of the normal child development can also be performed through longitudinal determination of parameters and comparison to normative values. Data can be shared with clinician's office.

19 Claims, 38 Drawing Sheets

(51) Int. Cl.
*G06T 7/10* (2017.01)
*G06T 7/60* (2017.01)

(52) U.S. Cl.
CPC ............ *G06T 7/60* (2013.01); *A61B 2576/02* (2013.01); *G06T 2207/30004* (2013.01)

(58) Field of Classification Search
CPC . G06T 2207/20081; G06T 2207/20084; A61B 5/1079; A61B 2576/02; A61B 5/1077; A61B 2560/0233; A61B 2576/00; A61B 5/6898; A61B 5/7275; A61B 5/107; G16H 50/30; G16H 50/20; G16H 30/40; G16H 50/70

See application file for complete search history.

(56) References Cited

U.S. PATENT DOCUMENTS

| | | | |
|---|---|---|---|
| 7,266,225 | B2 | 9/2007 | Mariani et al. |
| 7,280,682 | B2 | 10/2007 | Littlefield et al. |
| 7,545,965 | B2 | 6/2009 | Suzuki et al. |
| 7,587,274 | B2 | 9/2009 | Kaldewey et al. |
| 9,443,161 | B2 | 9/2016 | Guo |
| 9,734,285 | B2 | 8/2017 | Venon et al. |
| 2016/0182817 | A1* | 6/2016 | Scharl ................ H04N 23/635 348/50 |
| 2017/0228129 | A1 | 8/2017 | Shen et al. |
| 2019/0028637 | A1* | 1/2019 | Kolesov ................ H04N 23/63 |

FOREIGN PATENT DOCUMENTS

EP 3 261 056 A1 12/2017
WO WO 2016/172447 A1 10/2016

OTHER PUBLICATIONS

Atmosukarto et al. "3D Head Shape Quantification for Infants with and without Deformational Plagiocephaly." (author manuscript), NIH Public Access, Jul. 2010, pp. 1-31 (Year: 2010).*
Hutchison et al. "Quantification of Plagiocephaly and Brachycephaly in Infants Using a Digital Photographic Technique." Cleft Palate—Craniofacial Journal, vol. 42, No. 5, Sep. 2005, pp. 539-547 (Year: 2005).*
English Translation of CN 106960461 A (Year: 2017).*
International Search Report and Written Opinion dated Jun. 17, 2019 in PCT/US2019/023843 filed on Mar. 25, 2019.
Extended European Search Report dated Nov. 24, 2021 in European Patent Application No. 19776157.0, 12 pages.
B. Lynne Hutchison, et al., "Quantification of Plagiocephaly and Brachycephaly in Infants Using a Digital Photographic Technique," Cleft Palate—Craniofacial Journal, vol. 42, No. 5, XP055861406, Sep. 2005, pp. 539-547.

* cited by examiner

|  |  | Present Disclosure | Prior Results |
|---|---|---|---|
| Limit of Agreement | CI | 5.3 | 7.5 |
|  | CVAI | 3.85 | 6.6 |
| Bias | CI | -1.9 | -1.8 |
|  | CVAI | 1.2 | -3.0 |

FIG. 11

SYSTEMS AND METHODS OF MEASURING THE BODY BASED ON IMAGE ANALYSIS

CROSS-REFERENCE TO RELATED APPLICATIONS

The present application claims priority to U.S. Provisional Application No. 62/647,884, filed Mar. 26, 2018, the teaching of which is hereby incorporated by reference in its entirety for all purposes.

BACKGROUND

Field of the Disclosure

The present disclosure relates to systems and methods that allow a user to measure, analyze, record, and monitor, from image analysis, a body part of a patient. In particular, the present disclosure relates to using the systems and methods for measurement, analysis, monitoring, and records of head shape and growth, ear deformities, shape of the fingers, arms, legs and feet, shape of the back and vertebral body, facial features, body shape changes with disease, trauma, or injury, and the like.

Description of the Related Art

As related to infants, body deformities, such as flat head syndrome or craniosynostosis, are often underdiagnosed and, as a result, a critical treatment window may lapse. This is due, in part, to the infrequency of doctor visits during a critical period of development. Such body deformities may manifest across the body, including as flat head syndrome, craniosynostosis, ear deformities, bow legs, knock knees, in-toeing gait, out-toeing gait, and other deformities impacting the spine, hands, arms, and face.

Flat head syndrome (FHS), in particular, is a condition characterized by geometrical distortion of the cranium. In addition to deformities caused by FHS and the associated psychological pressure, it has been shown that FHS is related to a series of developmental delays that may continue through 3 years of age and can even persist during school years. In fact, a significant correlation exists between FHS and developmental delays in early childhood. Fortunately, unlike developmental delay, FHS can be detected early on in a quantitative and objective manner. While timely evaluation during infancy may ensure those children receive appropriate and specific care, quantitative measures of head shape are not routinely performed as pediatrician visits can be months apart. Moreover, first time parents may have little awareness about the risks of untreated FHS. If FHS remains undiagnosed at 4-6 months of age, intense therapy may become the only option.

Timing of the diagnosis, therefore, becomes critical in determining an appropriate treatment method and, thereby, minimizing undue burden to the patient. Treatment for FHS can include repositioning or helmet therapy. For instance, when mild to moderate FHS is detected early, repositioning therapy can be done by parents at home and at no cost, often with positive outcomes. Helmet therapy, though costly and requiring an infant to wear the helmet for 23 hours of a day for up to 4 months, can be effective in more severe cases and/or older infants. Physical therapy can also help when torticollis (i.e., neck muscle stiffness) is involved, important in context of the reality that 70-90% of plagiocephaly cases also demonstrate torticollis.

As mentioned, the ability to treat an infant suffering from a deformity such as FHS requires early diagnosis. Currently, diagnoses of FHS rely on timely referrals to orthotists, pediatric neurosurgeons, or plastic surgeons that use visual assessment, a craniometer, or, occasionally, 3D imaging to determine the type and severity of the cranial malformation. Such referrals and logistical hurdles can result in months of waiting before a proper diagnosis can be made and necessary treatment can be initiated. In some cases, untreated FHS or its underlying causes can lead to long-term health complications including mandibular asymmetry, elevated risk of auditory processing disorders, and abnormal drainage of the Eustachian tube.

Therefore, as described in the present disclosure, it becomes necessary to develop a method to enable at-home measurement and analysis of, for instance, infant head shapes, thereby giving parents control in determining cranial abnormalities of the children and allowing them to seek appropriate medical care in a timely manner. Such an approach can also exploit the unprecedented use of smartphone technologies by parents, and specifically first time parents, in seeking medical advice and their presence in social media, thereby raising awareness as to bodily deformities.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to systems and methods of measuring the body based on image analysis.

According to an embodiment, the present disclosure further relates to a system, comprising an image sensor configured to acquire one or more images of a head of a patient, the head of the patient having a cranial shape, a display, and processing circuitry configured to receive the one or more images of the head of the patient, determine a cranial contour based on the received one or more images of the head of the patient, calculate at least one cranial parameter based on the determined cranial contour, the at least one cranial parameter being one selected from a group including cephalic index and cranial vault asymmetry index, compare the at least one cranial parameter to a pre-determined threshold of the at least one cranial parameter, and determine, based on the comparison, an abnormality of the cranial shape of the head of the patient.

According to an embodiment, the present disclosure further relates to a method, comprising receiving, by processing circuitry, one or more images of a head of a patient, the head of the patient having a cranial shape, determining, by the processing circuitry, a cranial contour based on the received one or more images of the head of the patient, calculating, by the processing circuitry, at least one cranial parameter based on the determined cranial contour, the at least one cranial parameter being one selected from a group including cephalic index and cranial vault asymmetry index, comparing, by the processing circuitry, the at least one cranial parameter to a pre-determined threshold of the at least one cranial parameter, and determining, based on the comparison and by the processing circuitry, an abnormality of a cranial shape of the head of the patient.

According to an embodiment, the present disclosure further relates to a system, comprising an image sensor configured to acquire one or more images of a region of a body of a patient, a display, and processing circuitry configured to receive the one or more images of the region of the body of the patient, calculate at least one region parameter based on the received one or more images, determine, based on the at least one region parameter, an abnormality of the region of the body of the patient.

According to an embodiment, the present disclosure further relates to a system, comprising an image sensor, a display, a touch screen panel, and processing circuitry implementing a user interface ("UI") by being configured to guide a user in acquiring, via the image sensor, one or more images of a region of a body of a patient, and display an evaluation of at least one parameter of the region of the body of the patient, the evaluation of the at least one parameter indicating whether the region of the body of the patient is abnormal, wherein the at least one parameter of the region of the body of the patient is calculated based on the acquired one or more images of the region of the body of the patient.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 11 is a tabular representation of a Bland-Altman Plot comparing experimentally determined head measurements with ground truth head measurements, according to an exemplary embodiment of the present disclosure;

DETAILED DESCRIPTION

Figure 1C:
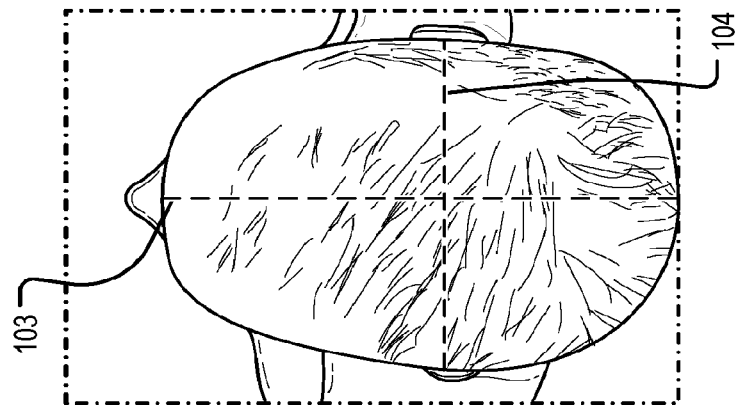
FIG. 1C is an illustration of an exemplary presentation of flat head syndrome, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Anatomical deformities can manifest within a variety of bodily structures, often portending maladies. As introduction, a subset of a variety of anatomical deformities will be described below.

The deformity can be, for instance, an ear deformity. Such ear deformities can include Stahl's ear, prominent ear, helical rim, cryptotia, lidding, cup ear, conchal crus, or a combination of deformities. Some ear deformities are temporary. For instance, if the deformity was caused by abnormal positioning in the uterus or during birth, it may resolve as the child grows and the ear takes more normal form. Other ear deformities will need medical intervention—either non-surgical or surgical—to correct the ear anomaly. As it is unknown which ear deformities will correct on their own and which will not, it is important to detect and diagnose such abnormalities at an early stage. Some deformities can be resolved by noninvasive molding performed at pediatric offices, wherein a 'cast' is used to guide growth. If undiagnosed until the infant is older, for instance, beyond 4 weeks of age, plastic surgery may be the only option.

Similarly, the deformity can be any one of a number of deformities of the extremities. Bow legs, knock knees, flat feet, in-toeing, and out-toeing gaits of the lower extremities in children, though common, often cause undue parental anxiety, prompting frequent visits to general practice. Further to the above, the deformity can be a deformity of the upper extremities, including finger deformities.

As described in the present disclosure, and briefly introduced here, properly processed and analyzed 2D or 3D photographs acquired by parents' or caregivers' using smart devices or other scanning devices may provide early and at the point of care diagnosis of, for instance, ear deformities. Processing and analysis can be performed by, for instance, shape analysis, image-based measurements, machine learning technologies and deep learning methods trained to detect and monitor deformities of the body. For instance, a system of the present disclosure can implement a method for determining deformities of the ear and extremities as well as the spine, hand, arm, and face, among others. In determining the above-described deformities, a method of the present disclosure enables caregivers or parents at the point of care to detect these deformities, share the results remotely with their health provider and monitor the progress at the convenience of the home or office.

As is the focus herein, a system implementing a method of the present disclosure can also be applied to cranial abnormalities.

Figure 1B:
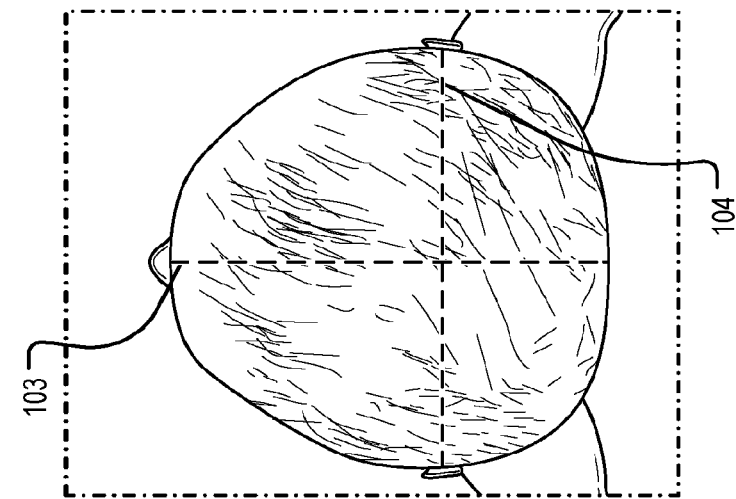
FIG. 1B is an illustration of an exemplary presentation of flat head syndrome, according to an exemplary embodiment of the present disclosure.
Figure 1A:
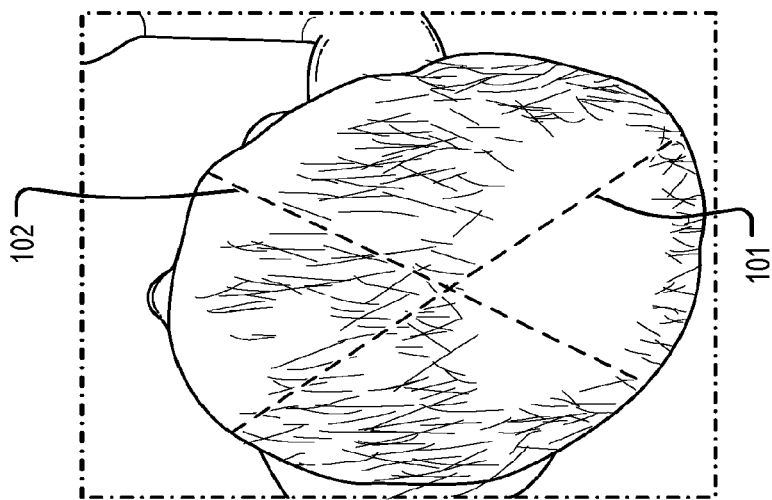
FIG. 1A is an illustration of an exemplary presentation of flat head syndrome, according to an exemplary embodiment of the present disclosure.
Figure 2C:
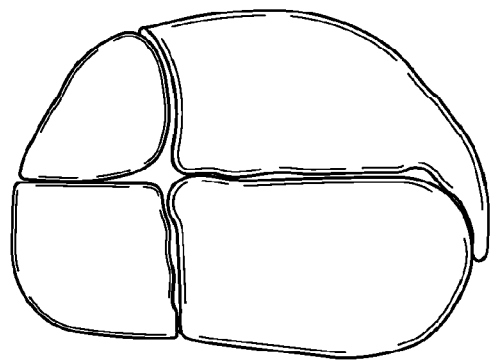
FIG. 2C is an illustration of a type of craniosynostosis, according to an exemplary embodiment of the present disclosure.
Figure 2B:
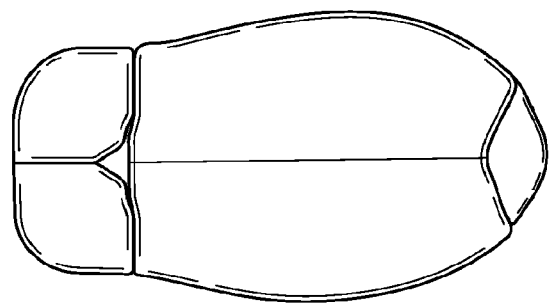
FIG. 2B is an illustration of a type of craniosynostosis, according to an exemplary embodiment of the present disclosure.
Figure 2A:
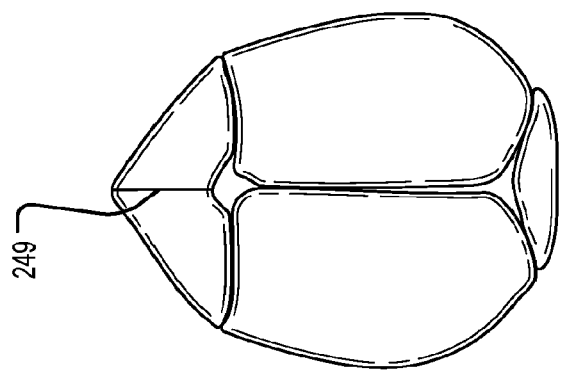
FIG. 2A is an illustration of a type of craniosynostosis, according to an exemplary embodiment of the present disclosure.
Figure 2E:
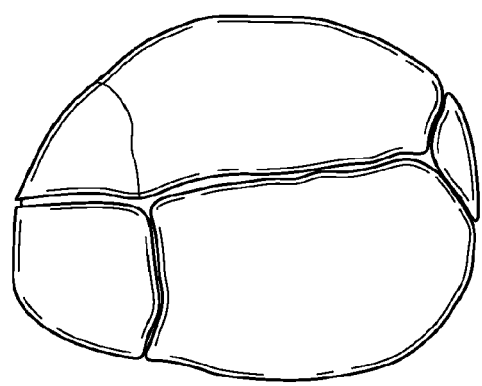
FIG. 2E is an illustration of a type of craniosynostosis, according to an exemplary embodiment of the present disclosure.
Figure 2D:
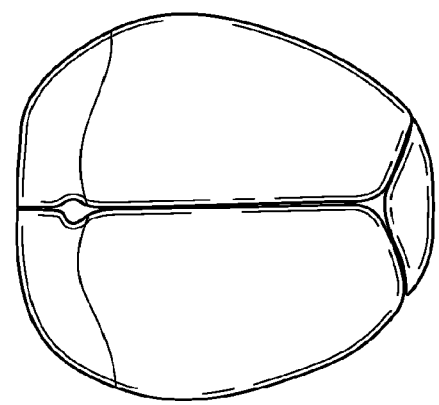
FIG. 2D is an illustration of a type of craniosynostosis, according to an exemplary embodiment of the present disclosure.

FIG. 1A through FIG. 1C illustrate cases of flat head syndrome (FHS). In one case, FHS can manifest as an asymmetrical distortion referred to as plagiocephaly (FIG. 1A). As shown in FIG. 1B, FHS can manifest as a flattening of the back of the head referred to as brachycephaly. With reference to FIG. 1C, FHS can manifest as an elongation of the head referred to as scaphocephaly.

Sometimes responsible for FHS, examples of craniosynostosis are shown in FIG. 2A through FIG. 2E. Craniosynostosis, in which one or more cranial sutures fail to ossify at the correct time, affects 1 in every 2,000 births and can result in brain damage leading to neurodevelopmental sequalae. FIG. 2A, FIG. 2B, FIG. 2C, FIG. 2D, and FIG. 2E illustrate, respectively, metopic craniosynostosis (trigonocephaly), sagittal synostosis (scaphocephaly), lambdoid synostosis (posterior plagiocephaly), bicoronal synostosis (brachycephaly), and unicoronal synostosis (anterior plagiocephaly). In the majority of cases, one or more cranial sutures ossify prematurely. With regard to trigonocephaly, the metopic suture 249 closes, or ossifies, prematurely and the cranial shape develops abnormally, accordingly. Failure to diagnose craniosynostosis can lead to lifelong morbidity including speech difficulties or blindness. Conversely, over diagnosis can subject the child to unnecessary invasive and potentially morbid cranial surgeries. Therefore, early and accurate detection of craniosynostosis is critical to minimizing potential damage and facilitating less invasive surgical treatment with improved outcomes.

With reference again to FIG. 1A through FIG. 1C, of the common treatments of FHS, repositioning therapy can be readily administered by parents at home and involves positioning a baby's head such that pressure is placed at the bulging area while enough room for growth is left at the flat side. To this end, placing a baby on their stomach while awake is the most recommended position. Alternatively, a baby may be placed on their side or on their back looking sideways. Pillows having designed cavities may also be used. In addition, parents can become aware of the underlying causes of FHS, such as torticollis (i.e, weak neck muscles at one side of the head). This weakness can be addressed by exercise or by visiting physiotherapists. If an infant's head shape remains deformed after administering repositioning therapy or if FHS is discovered too late in the infant's development, as can be the case, helmet therapy may be prescribed. Following measurement of the infant's head shape in three dimensions (using a 3D scanner, for example), a customized correctional helmet, designed to worn by the infant 23 hours of the day, can be fabricated. In an example, head volume can be determined.

Time-sensitive diagnosis of FHS, therefore, is critical to successful treatment outcomes. For instance, repositioning therapy is most effective before 4-6 months of age. Accordingly, as described in detail below, the present disclosure describes, in part, a system including but not limited to software that allows parents or care providers to be aware of the condition, detect and monitor an infant's head shape, helps to identify FHS and the degree of severity at early stages, tracks infant head shape and growth, provides options and instructions for repositioning and/or helmet therapy, and refers parents to appropriate medical professionals and/or therapy providers.

In each of the above-described cases illustrated in FIG. 1A through FIG. 1C, FHS can be defined, in part, according to cranial dimensions. Plagiocephaly can be defined by a first diagonal 101 and a second diagonal 102 (FIG. 1A), brachycephaly can be defined by a length 103 and a width 104 (FIG. 1B), and scaphocephaly can be defined by a length 103 and a width 104 (FIG. 1C). These cranial dimensions can be further used in the determination of cranial parameters used during head shape evaluation, including cephalic index (CI), cranial vault asymmetry (CVA), and cranial vault asymmetry index (CVAI). CI refers to a ratio of the head width 104 to the head length 103 while CVAI refers to a ratio of asymmetry between a right diagonal and a left diagonal, or a first diagonal 101 and second diagonal 102, and can be defined as the ratio of CVA divided by the larger of the first diagonal and the second diagonal, where CVA is defined by subtracting the maximum and minimum diagonals of the head in top view. Comparisons of these cranial parameters to benchmark values can indicate a condition of a patient. For example, an infant's head can be diagnosed with mild plagiocephaly when CVAI is greater than 3.5%. An infant's head can be diagnosed with brachycephaly when CI is larger than 90%. An infant's head can be diagnosed with scaphocephaly when CI is less than 76%.

Currently determined via craniometer during doctor's office visits, an approach for determining the above-described cranial parameters, for instance, outside of a professional setting is needed. To this end, cranial parameters can be calculated with statistically comparable diagnostic accuracy through manual extraction of landmark features within a 2D top view image of an infant's head. Accordingly, the present disclosure describes, in part, image processing that allow a novice user to generate and analyze cranial parameters conveniently, with accuracy and consistency, following acquisition of images of an infant's head. This allows automation of the process and, therefore, scaling to mass numbers of users around the world, including remote and underserved areas.

Herein described are systems and methods for image-based measurement and longitudinal monitoring of body deformities including but not limited to FHS, craniosynostosis, bowed legs, ear deformities, and finger deformities. The systems and methods of the present disclosure can include providing customized guidance to parents, care providers and other users to promote practices that correct the deformity or the underlying cause. The methods and systems disclosed herein can be performed by processing circuitry resident in a mobile or stationary computing system and can allow users to, for instance, monitor the deformity at the point of care, receive instant quantitative and qualitative measurements relating to different deformities, receive a preliminary diagnosis, and receive instructions for therapeutic methods. The methods and systems disclosed herein can be performed by processing circuitry and displayed to a user via a software user interface. Further to the above, and based on the severity of the condition, a method of the present disclosure may recommend the user to be evaluated by a medical professional. Such recommendation may include providing a list of related medical care providers in the geographical vicinity, their wait time, and ratings.

In addition, if requested by users, the measurements can be sent to health providers in an instant or on a regular basis. The measurements can include cranial parameters indicating or representing the head circumference, CI, CVAI, head volume, craniosynostosis, and the like. Measurements can be complemented by physician measures completed during doctor's visits. Additionally, records of patient measurements and shapes can be stored on remote servers for monitoring purposes.

According to an embodiment, processing circuitry for processing the images and generating analysis may either run on a mobile device, computer or on remote servers in the cloud. The processing circuitry can use image analysis, shape analysis, machine learning and deep learning methods for detection of FHS, in particular, as well as craniosynostosis, ear deformities, bowed legs, and other deformities and conditions.

According to an embodiment, the present disclosure includes computerized methods to calculate head shape, and other cranial parameters, including but not limited to CI, CVA/CVAI, head circumference, and the like. The calculated head shape and other cranial parameters can be based on photographic images acquired from, for example, a top view image (bird's eye view image), front view image, side view image, or back view image or a combination thereof. The calculated head shape and other cranial parameters can also be based on a 3D scan of an infant's head acquired by a camera such as a smartphone camera or tablet camera or another photographic device. Either of the above acquired 2D or 3D images may include the nose, ears and forehead (e.g. clues on the location of eyebrows) of the infant.

Figure 3A:
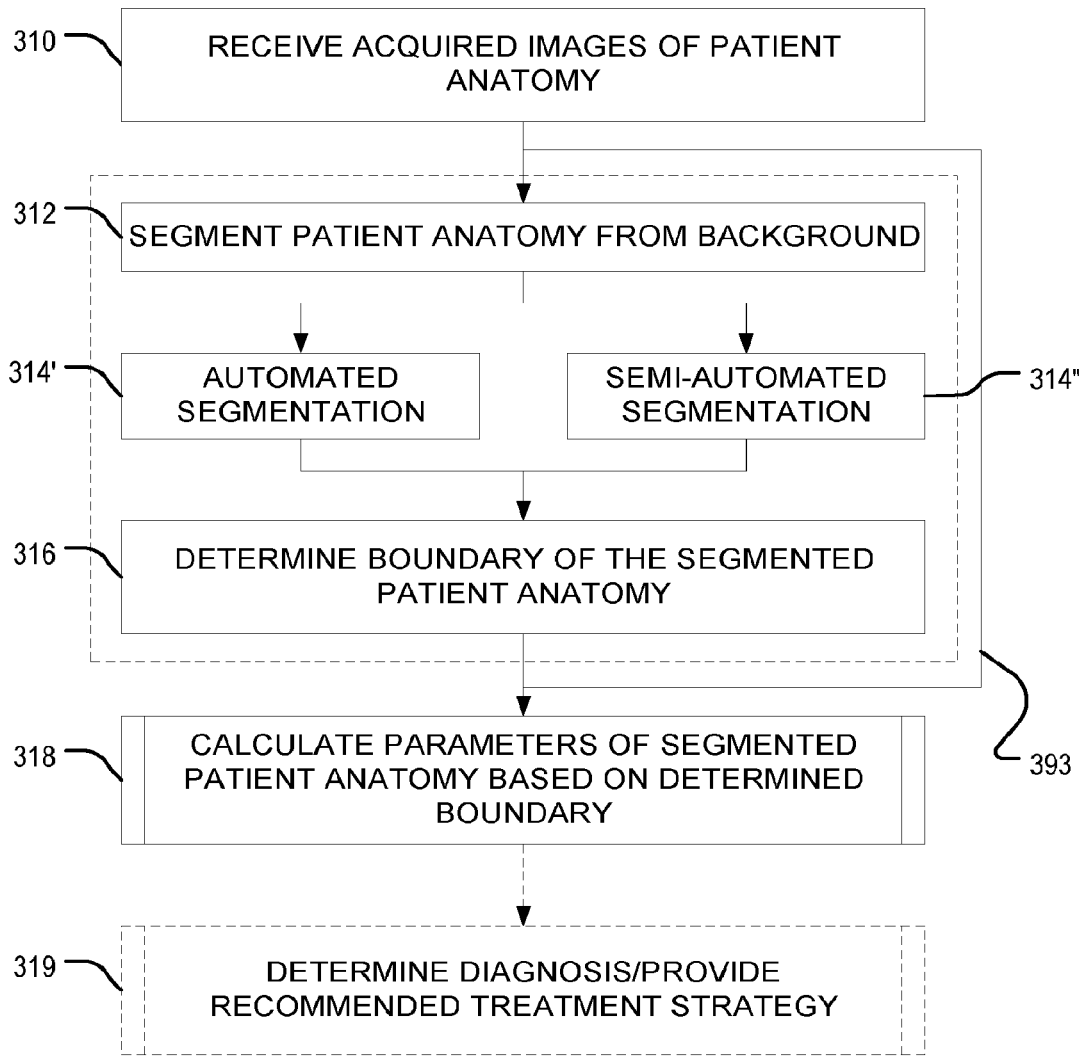
FIG. 3A is a flow diagram of a method of measuring a body part of a patient, according to an exemplary embodiment of the present disclosure.

With reference now to FIG. 3A, process 300 describes a general method of the present disclosure as applied to 2D images. A similar approach for 3D images, as described with respect to FIG. 13A through FIG. 13C, can be employed mutatis mutandis. In particular, process 300 describes a method of determining a diagnosis and/or providing a recommended treatment strategy for a patient. The method can be performed by processing circuitry of a mobile device, such as a smartphone, a terminal workstation, a remote server, and the like.

At step 310 of process 300, one or more acquired images of a region of anatomy of a patient can be received. The one or more acquired images can be acquired by an image sensor. In an embodiment, the image sensor can be integrated within a smartphone.

In an embodiment, the one or more acquired images received at step 310 of process 300 can be directly delivered 393 to step 318 of process 300, steps within the dashed box of FIG. 3A being ignored, and at least one parameter can be calculated based on the received one or more images of the region of the body of the patient. Accordingly, the calculated at least one parameter can be passed to step 319 of process 300, where it can be determined, based on the calculated at least one parameter, whether the region of the body of the patient is abnormal. This type of accelerated pathway may be applicable to both 2D and 3D implementations and may be appropriate when, for example, a whole image analysis is performed and the at least one parameter is calculated directly therefrom.

Alternatively, and as will be the focus, for simplicity, of the remaining embodiments herein, the one or more acquired images received at step 310 of process 300 can be delivered to a segmentation step at step 312.

At step 312 of process 300, the one or more acquired images can be segmented in order to isolate a particular region of patient anatomy from the surrounding environment. The segmentation can be an automated process, as described at step 314' of process 300, or a semi-automated process, as described at step 314" of process 300. With respect to an automated process at step 314', the segmentation can proceed by automatic segmentation methods, such as thresholding of the image according to known pixel relationships, or by application of a machine learning method such as a convolutional neural network, the convolutional neural network being trained to identify the region of anatomy of the patient and segment it from the image, accordingly. Such machine learning approaches will be described in detail with respect to FIG. 20 through FIG. 23B. With respect to a semi-automated process at step 314", the processing circuitry can be configured to receiver a user command indicating where the head and/or background of the image is. A segmentation algorithm, such as region growing, level set, active contour, graph cuts or other method based on image appearance, and shape analysis can be applied.

Based on the above, a boundary of the segmented anatomy of the patient can be determined at step 316 of process 300. In an embodiment, the boundary of the segmented anatomy of the patient is a head circumference.

At sub process 318 of process 300, the boundary of the segmented anatomy of the patient can be used to determine parameters of the segmented anatomy of the patient. In an embodiment, the parameters can be organ and tissue specific, including geometric relationships such as length, width, circumference, and volume.

At sub process 319 of process 300, the calculated parameters of the segmented anatomy of the patient can be compared with known benchmarks for a specific parameter of a specific organ or tissue, and a diagnosis or a recommended treatment can be determined, accordingly.

Figure 3B:
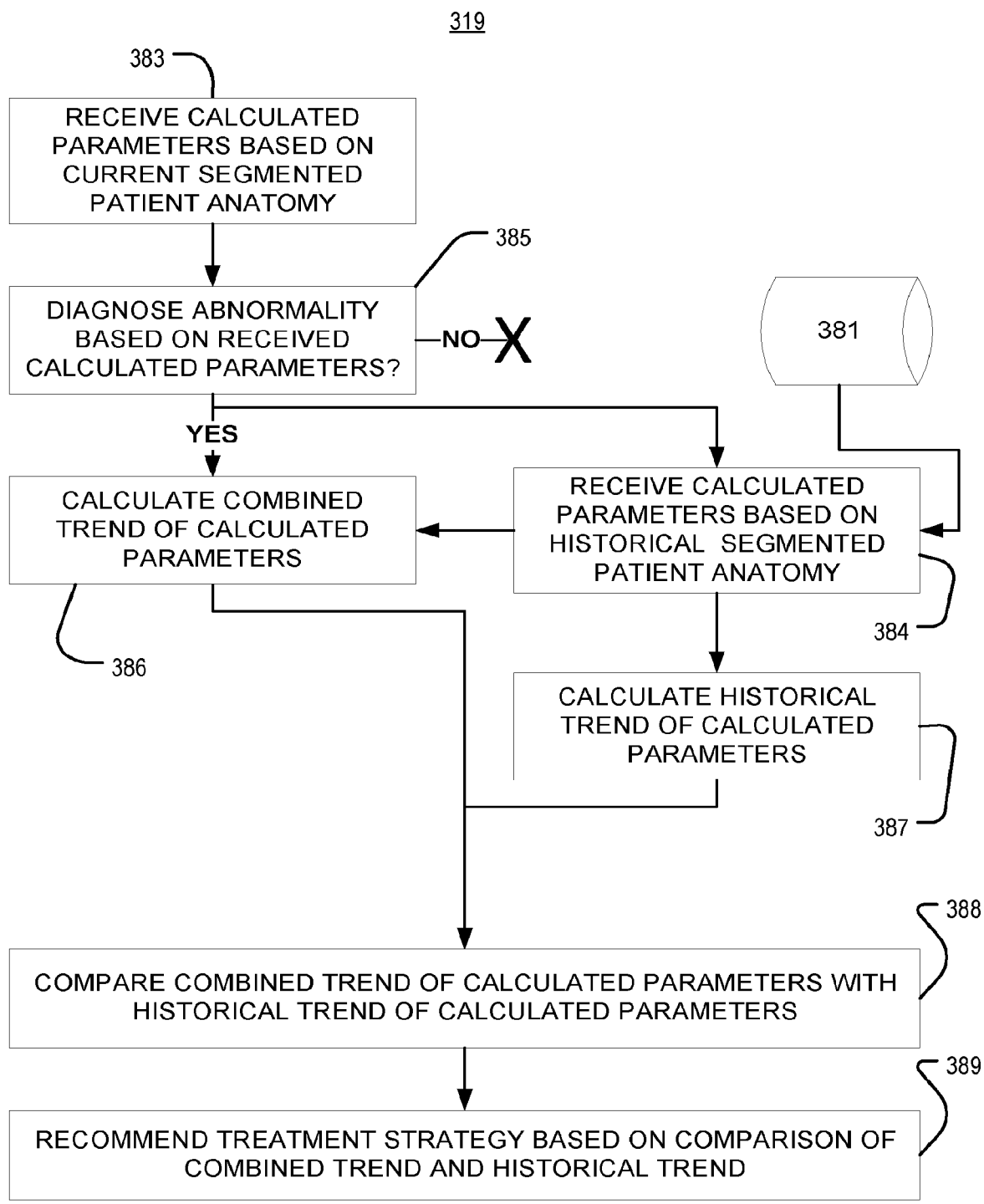
FIG. 3B is a flow diagram of a method of evaluating a measured body part of a patient, according to an exemplary embodiment of the present disclosure.

According to an embodiment, the above-described transient application of the method 300, and sub-process 319, in particular, can also be considered in the context of a continuous application, wherein longitudinal data of patient growth is considered. Therefore, FIG. 3B is a flow diagram of sub process 319, wherein determining a diagnosis and providing recommended treatment strategy can be performed in context of historical patient data.

At step 383 of sub process 319, calculated parameters (step 318 of process 300), or current parameters, based on the current segmented patient anatomy can be received by processing circuitry.

At step 385 of sub process 319, as generally described with respect to FIG. 3A, the calculated parameters of the segmented anatomy of the patient can be compared with known benchmarks for a specific parameter of a specific organ or tissue, and a diagnosis or a recommended treatment can be determined, accordingly. If the calculated parameters do not meet a pre-determined benchmark for a positive diagnosis, sub process 319 may end. If, however, the calculated parameters meet the pre-determined benchmark for the positive diagnosis, sub process 319 can proceed to step 386.

At step 384 of sub process 319, calculated parameters based on historical segmented patient anatomy, or historical parameters, can be received from a database (e.g., local server or remote server 381), where historical, or longitudinal, patient data can be stored.

At step 386 of sub process 319, the current parameters can be appended to the historical parameters and a combined model can be generated, the combined model indicating a trend of the parameters over time.

Similarly, at step 387 of sub process 319, a model of the historical parameters can be generated, the historical model indicating a trend of the parameters up to and excluding the current calculation of parameters.

Accordingly, at step 388 of sub process 319, the combined model and the historical model can be compared to determine, for instance, differences between the curves or trends of the models. Moreover, the curves can be used to estimate future parameters of the segmented patient anatomy, providing predictive power in evaluating the progression of a patient.

In this way, as at step 389 of sub process 319, it may be possible to determine if a therapy has been effective or if the patient is developing within healthy parameters. For instance, though a patient may still be diagnosed as having an abnormal condition, a comparison of the combined model and the historical model may indicate that the abnormal condition is improving and the current therapy should continue. Alternatively, the comparison of the combined model and the historical model may indicate that the abnormal condition is worsening and that an alternative treatment should be recommended and pursued. Alternatively, the model can be used to monitor normal infant growth.

This type of longitudinal patient evaluation can also be shared with a physician in order to provide a complete picture of normal development or development of an abnormal condition of the patient.

Figure 3C:
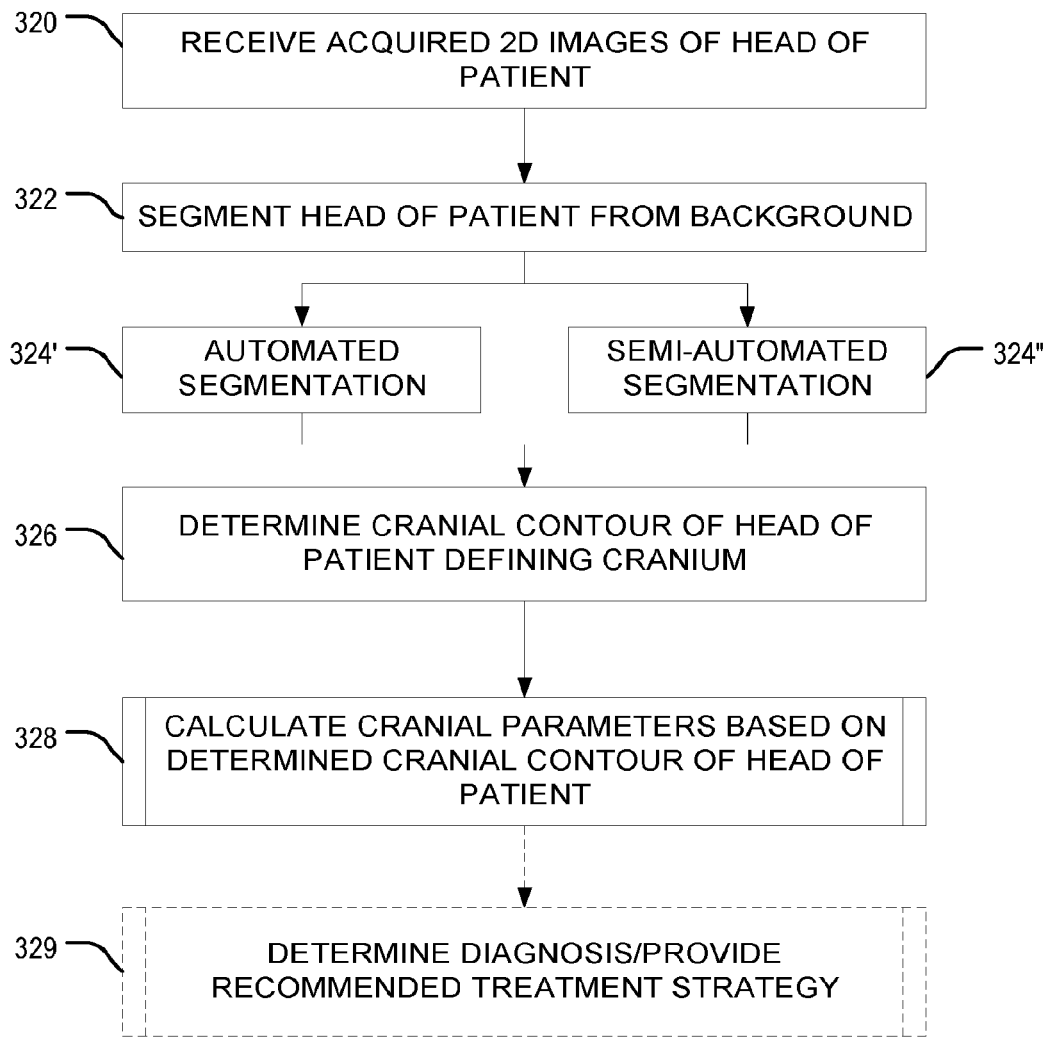
FIG. 3C is a flow diagram of a method of measuring cranial parameters of a head of a patient, according to an exemplary embodiment of the present disclosure.

The general process 300 of FIG. 3A and FIG. 3B can be better appreciated through an exemplary implementation of process 300 in a cranial application, as described in FIG. 3C. For practicality, process 300 of FIG. 3C can be considered implemented on a mobile device having at least one integrated image sensor and display. It can be appreciated that the integrated image sensor may be a depth sensor.

At step 320 of process 300, one or more acquired images of a head of a patient can be received. The one or more acquired images can be acquired by an image sensor of a camera. In an embodiment, the camera can be integrated within a smartphone. Each of the one or more acquired images can be 2D images of a birds' eye view, a side view, a back view or a front view of the head of the patient. Alternatively, each of the one or more acquired images can be a 3D image acquired via, for instance, application of structured light to the head of the patient, a plurality of cameras, or another 3D imaging system, as would be understood by one of ordinary skill in the art. A 3D image application will be described in more detail with respect to FIG. 13A through FIG. 13C.

At step 322 of process 300, the one or more acquired images can be segmented in order to isolate the head of the patient from the surrounding environment. The segmentation can be an automated process, as described at step 324' of process 300, or a semi-automated process, as described at step 324" of process 300. With respect to an automated process at step 314', the segmentation can proceed by automatic segmentation methods, such as thresholding of the image, according to known pixel relationships or by application of a machine learning method such as a convolutional neural network, the convolutional neural network being trained to identify the region of anatomy of the patient and segment it from the image, accordingly. With respect to a semi-automated process at step 314", the processing circuitry can be configured to receive a user command indicating where the head and/or background of the image are. A segmentation algorithm, such as region growing, level set, active contour, graph cuts or other method based on image appearance, and shape analysis can be applied. In an example, a user indicates the head of the patient and, via region growing, the head of the patient can be isolated from the background.

Figure 4B:
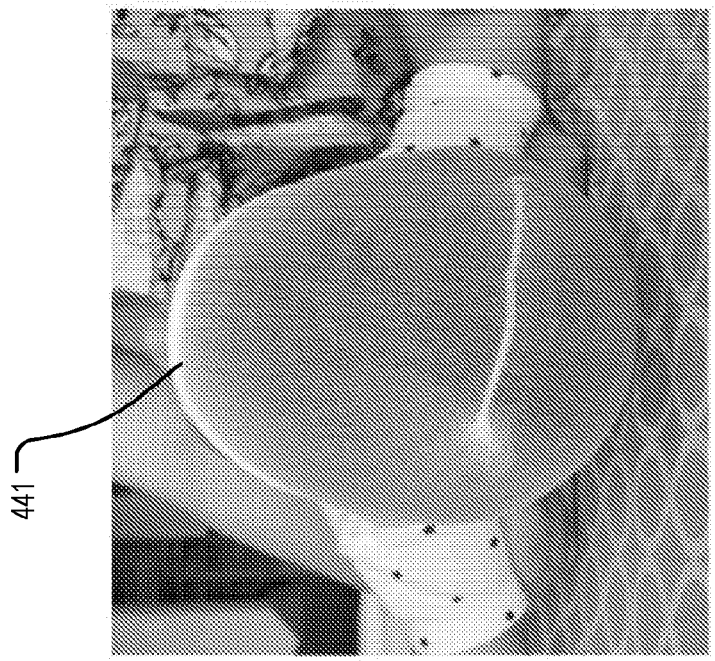
FIG. 4B is an image of a thin cap used to cover the head of an infant in order to reduce hair artifacts during head contour extraction, according to an exemplary embodiment of the present disclosure.
Figure 4A:
FIG. 4A is an image of an uncovered head of an infant, according to an exemplary embodiment of the present disclosure.

According to an embodiment, in order to facilitate segmentation, as described in steps 314' and 314" of process 300, the head of the patient may be outfitted with a thin cap, as shown in FIG. 4A and FIG. 4B. An uncovered head of a patient can be seen in FIG. 4A, while FIG. 4B shows a head of a patient covered with a cap 441 to enhance contrast with the background and expedite segmentation during processing. The cap 441 may be a thin cap. For practical purposes, the cap 441 can also secure hair of the patient close to the head to mitigate hair artifacts during cranial contour extraction. Alternatively, and to the same end, dual cameras can be used, allowing blurring of the background and removal thereof.

Figure 5:
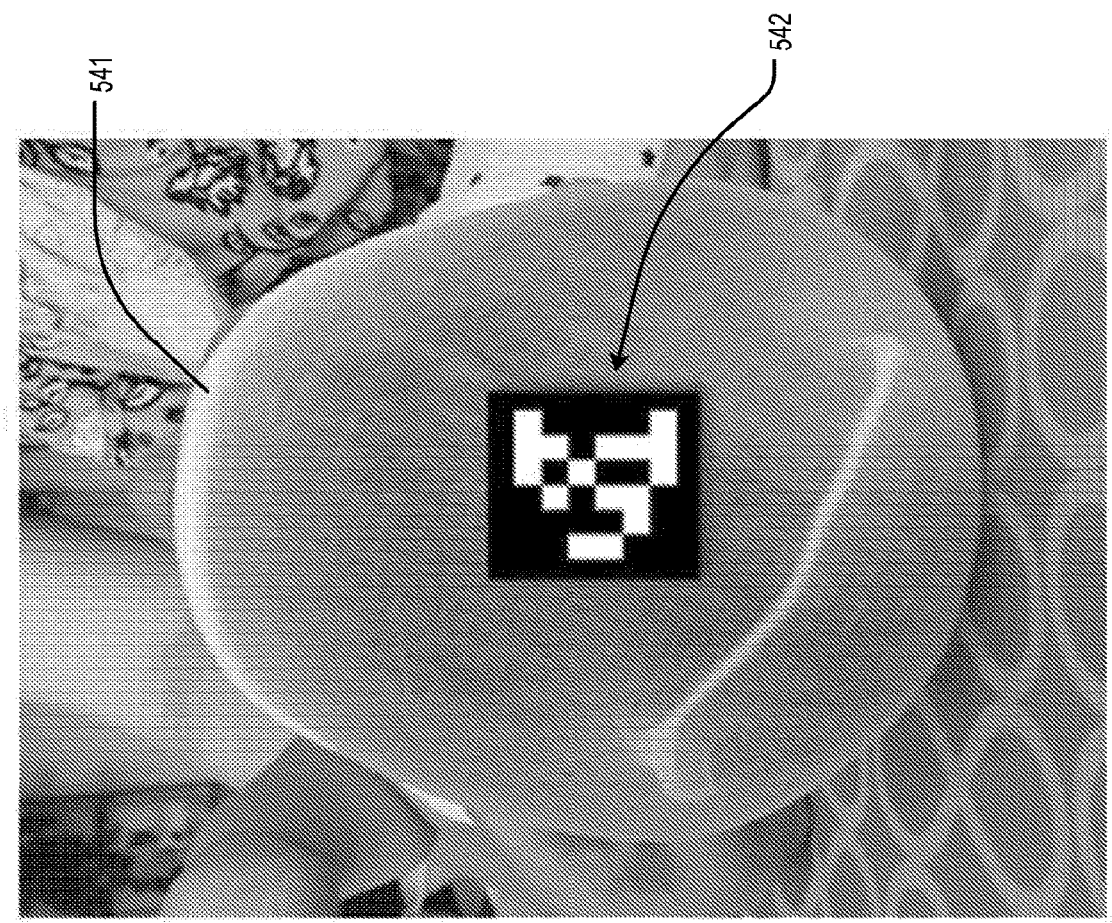
FIG. 5 is an image of a thin cap having an identifying marker, according to an exemplary embodiment of the present disclosure.

According to an embodiment, and as shown in FIG. 5, a marker 542 of a known physical size and geometry can be embedded within a cap 541, or otherwise made visible within the image frame, to allow the processing circuitry to calculate usable measurements, such as head circumference. (CI and CVAI do not require such a known geometry marker as they are unit-less indices.) The location of the marker 542, or calibration marker, may also provide information as to the orientation of the camera during image acquisition such that, when a plurality of images of a head of a patient are obtained, they can be correlated. The above-described marker 542 may be rendered of little use if, for instance, a stereoscopic camera or depth sensor, either external to or embedded within the mobile device is included, as quantifiable measurements of depth can be provided thereby.

Based on the above, a cranial contour of the segmented head of the patient can be determined at step 326 of process 300. In an embodiment, the cranial contour of the segmented head of the patient is a head circumference.

According to an embodiment, the head circumference may be isolated using any one of the above-described segmentation and analysis methods. In an example, and with regard first to step 324" of process 300, a region growing method can be used, wherein a seed point inside the head of the patient can be indicated by a user. This point can be an initial region from which the region expands to encompass the whole head by comparing neighboring pixels to the current region in an iterative process. With regard now to sub process 326 of process 300, the processing circuitry can then be configured to identify the boundary of the region as the cranial contour. The circumference of this cranial contour can be used for head circumference. In an embodiment, the user may be asked to select certain landmarks, such as a nose and/or ears, to initialize the calculations carried out in sub process 328.

At sub process 328 of process 300, the cranial contour of the segmented head of the patient can be used to determine cranial parameters of the segmented head of the patient. In an embodiment, the cranial parameters can include fundamental parameters such as length, width, right diagonal and left diagonal, among others. In an embodiment, the cranial parameters can include complex cranial parameters such as CI, CVA, and CVAI, among others.

At sub process 329 of process 300, the determined cranial parameters of the segmented head of the patient can be compared with known benchmarks for a specific cranial parameter, and a diagnosis or a recommend treatment can be determined, accordingly. For instance, as described previously, if CI of a head of a patient is greater than 90%, the patient can be diagnosed as having brachycephaly and attendant treatment can be recommended. The treatment may include visiting a physician or surgeon and may include repositioning therapy, as described previously in this disclosure.

Figure 3D:
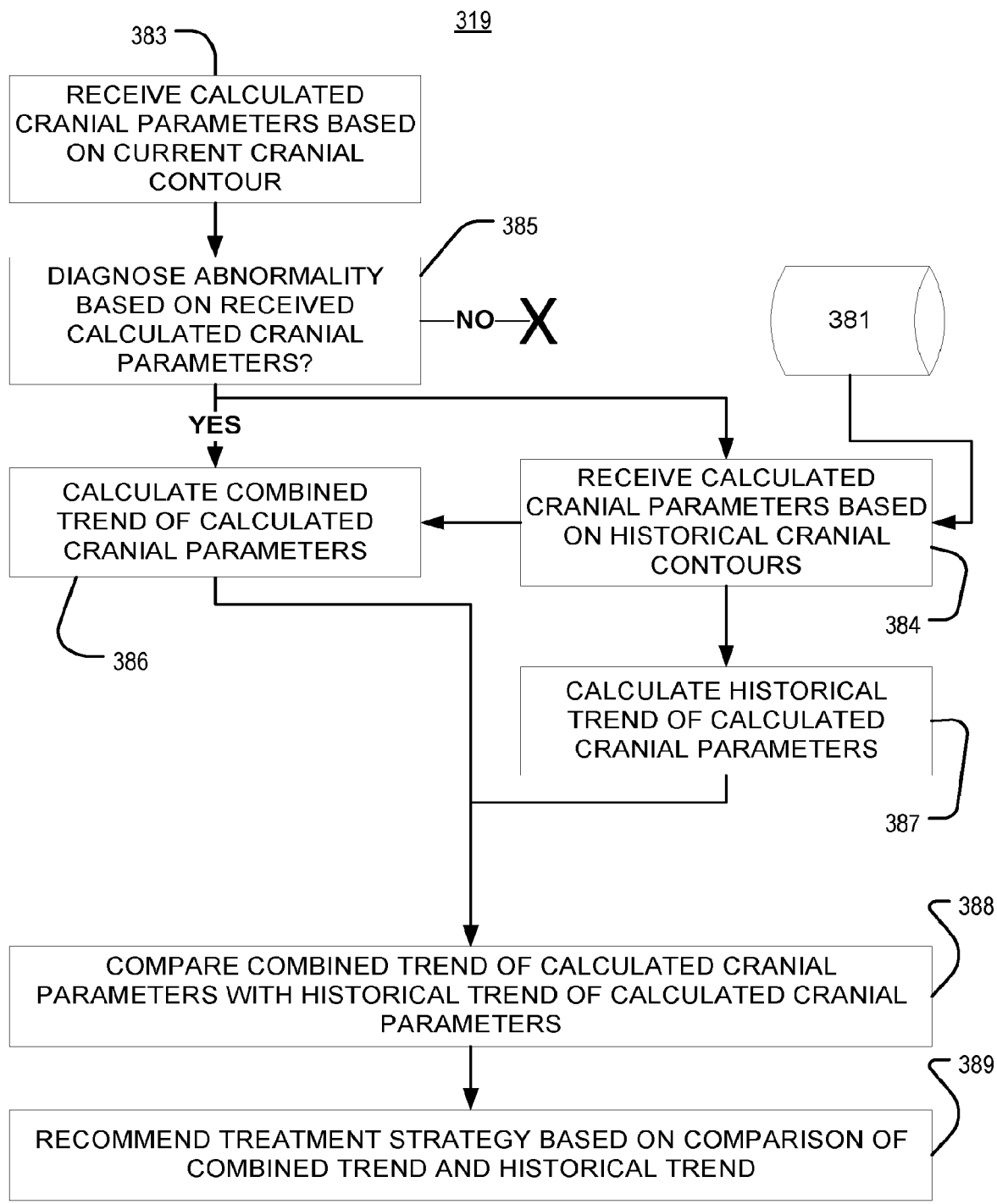
FIG. 3D is a flow diagram of a method of evaluating a measured body part of a patient, according to an exemplary embodiment of the present disclosure.

As shown in the flow diagram of FIG. 3B, the above-described transient application of the method 300, and sub-process 319, described with respect to, in particular, FIG. 3C, can also be considered in the context of a continuous application, wherein longitudinal data of patient growth is considered. Therefore, FIG. 3D is a flow diagram of sub process 319, wherein determining a diagnosis and providing recommended treatment strategy for a patient with a cranial abnormality can be performed in context of historical patient data.

At step 383 of sub process 319, calculated cranial parameters (step 318 of process 300), or current cranial parameters, based on the current cranial contour can be received by processing circuitry.

At step 385 of sub process 319, as generally described with respect to FIG. 3B, the calculated cranial parameters of the cranial contour can be compared with known benchmarks for cranial abnormalities, such as CI, CVA, and CVAI, and a diagnosis or a recommended treatment can be determined, accordingly. If the calculated cranial parameters do not meet a pre-determined benchmark for a positive diagnosis, sub process 319 may end. If, however, the calculated cranial parameters meet the pre-determined benchmark for the positive diagnosis of a cranial abnormality, sub process 319 can proceed.

At step 384 of sub process 319, calculated cranial parameters based on historical cranial contours, or historical cranial parameters, can be received from a database (e.g., local server or remote server 381), where historical, or longitudinal, patient data can be stored.

At step 386 of sub process 319, the current cranial parameters can be appended to the historical cranial parameters and a combined cranial model can be generated, the combined cranial model indicating a trend of the cranial parameters over time.

Similarly, at step 387 of sub process 319, a model of the historical cranial parameters can be generated, the historical cranial model indicating a trend of the cranial parameters up to and excluding the current calculation of cranial parameters.

Accordingly, at step 388 of sub process 319, the combined cranial model and the historical cranial model can be compared to determine, for instance, differences between the curves or trends of the models. Moreover, the curves can be used to estimate future parameters of the cranial contour, providing predictive power in evaluating the progression of a patient.

In this way, as at step 389 of sub process 319, it may be possible to determine if a therapy, such as repositioning therapy, has been effective or if the patient is growing within healthy parameters. For instance, though a patient may continue to be diagnosed as having a cranial abnormality, a comparison of the combined cranial model and the historical cranial model may indicate that the cranial abnormality is improving and the current therapy should continue. Alternatively, the comparison of the combined cranial model and the historical cranial model may indicate that the cranial abnormality is worsening and that an alternative treatment, such as helmet therapy, should be considered and/or recommended, and pursued. Alternatively, the model can be used to monitor normal infant growth.

Figure 6B:
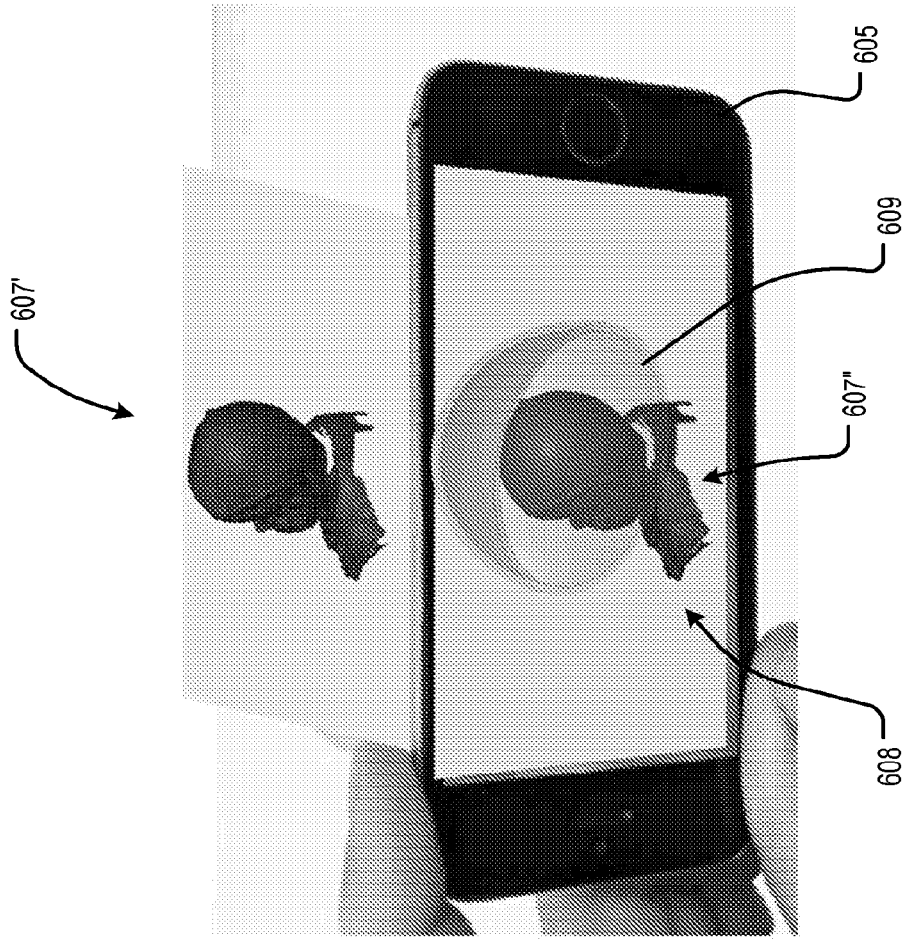
FIG. 6B is an image of an augmented hemisphere allowing for a variety of camera angles, according to an exemplary embodiment of the present disclosure.
Figure 6A:
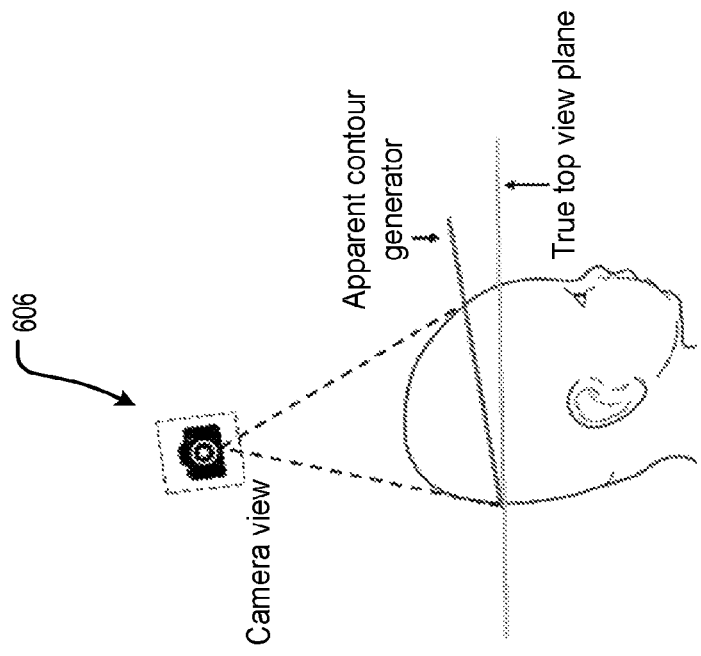
FIG. 6A is a schematic demonstrating camera angle influence on contour generation, according to an exemplary embodiment of the present disclosure.

As described above, process 300 can utilize one or more images gathered from a birds' eye view of a head of a patient. Therefore, it can be appreciated that camera angle can affect CI and CVAI measurement, as depicted in FIG. 6A and FIG. 6B. As shown in FIG. 6A, a camera 606 positioned from a birds' eye view of a patient must be appropriately angled in order to capture the 'true top view plane' necessary for accurate cranial measurements. In the case that an 'apparent contour generator' is not similar to the 'true top view plane', the processing circuitry can be further configured to provide visual guidance to the user during image acquisition such that a sufficient series of images can be acquired and the 'true top view plane' can be sufficiently captured. To this end, as shown in FIG. 6B, a mobile device 605 having a display 608 and at least one camera can acquire a series of images or videos in order to capture the complete head of the patient. The processing circuitry of the mobile device 605 can project a guiding feature 609 onto the display 608, overlaying the guiding feature 609 onto a virtual image 607" of real image 607' of a head of a patient. This guiding feature 609 can be a partial sphere (e.g. +/−30°) that can be augmented on the display 608 during image or video capture to aid the user in capturing all necessary images, thus compensating for shooting angle error (i.e. a view other than the birds' eye view, or top view). In an example, a thin cap with custom designed markers may be necessary to ensure image capture across the entire partial sphere.

According to an embodiment, it can be appreciated that side view images, rear view images, front view images, and the like, can also be acquired and used for redundant measurement of the CI and CVAI.

Figure 7A:
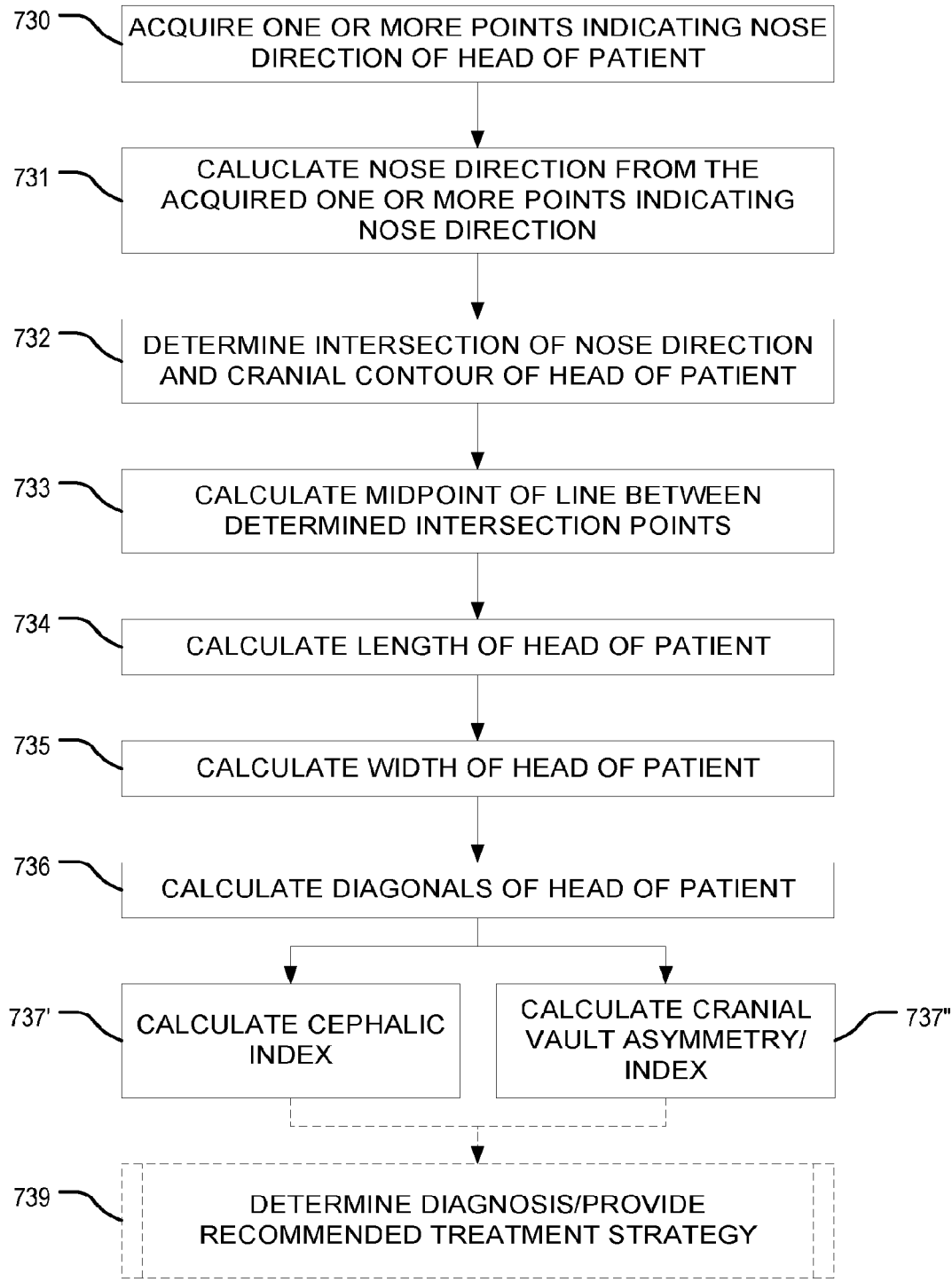
FIG. 7A is a flow diagram of a method of determination of cephalic index and cranial vault asymmetry index, according to an exemplary embodiment of the present disclosure.
Figure 7B:
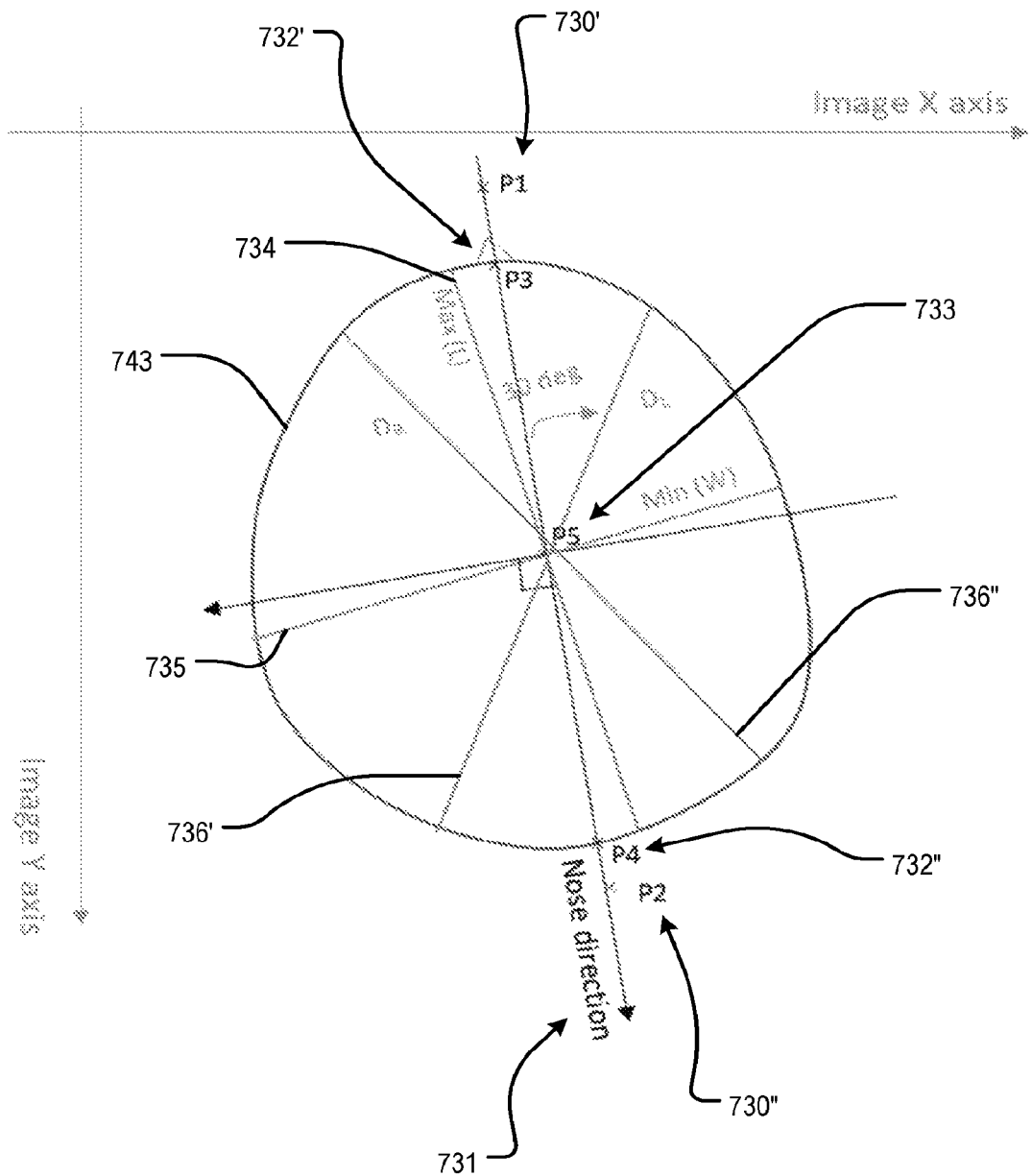
FIG. 7B is an illustration of a method of determination of cephalic index and cranial vault asymmetry index, according to an exemplary embodiment of the present disclosure.

With reference now to FIG. 7A and FIG. 7B, and in view of sub process 328 of FIG. 3D, calculations can be performed on the generated cranial contour 743 in order to calculate a subset of the fundamental and complex cranial parameters for sub process 329.

First, at step 730 of sub process 328, a landmark such as a tip of a nose of a patient can be selected as an anatomical reference. The nose can be indicated by a user, can be identified using image analysis methods, or can be identified by identifying a maximum radius of curvature on the cranial contour 743 as P1 730'.

At step 731 of sub process 328, nose direction 731 can be determined from the selected one or more points of step 730. In an embodiment, a center of mass of the cranial contour 743 can be identified as P2 730" and nose direction ($\theta_{nose}$) 731 can be calculated, therefrom. In an embodiment, the midpoint of the longest diagonal of the cranial contour 743 or the midpoint of a diagonal that divides the head area in half can be identified as P2 730".

At step 732 of sub process 328, an intersection of the nose direction 731 and the cranial contour 743 can be defined as P3 732' and P4 732".

At step 733 of sub process 328, the midpoint of a line formed between P3 732' and P4 732" can be defined as P5 733.

At step 734 of sub process 328, length (L) 734 of the head of the patient can be calculated as the length of a line inside the cranial contour 743 with maximum length that has an angle θ, where $\theta_{nose}-1 \leq \theta \leq \theta_{nose}+1$, and the line passes through point P5 733.

At step 735 of process 328, width (W) 735 of the head of the patient can be calculated as the length of a line inside the cranial contour 743 that is perpendicular to L 734 and passes through point P5 733.

At step 736 of sub process 328, the diagonals ($D_R$, $D_L$) (736', 736") can be calculated as the length of one or more lines inside the cranial contour that have α and −α degrees angles relative to the $\theta_{nose}$ 731 and pass through point P5 733, where a is either {30, 40, 45}.

At step 737' of sub process 328, CI, an exemplary cranial parameter, can be calculated as CI=W/L.

At step 737" of sub process 328, CVAI, an exemplary cranial parameter, can be calculated as $$CVAI = \frac{|D_R - D_L|}{\max(D_R, D_L)}.$$

In an embodiment, and if a cap with a known pattern geometry is used, CVA can also be calculated concurrent with step 737' and step 737" of sub process 328 as CVA=$|D_R-D_L|$.

The above-calculated exemplary cranial parameters can then be used at step 739 of sub process 328 to determine a diagnosis of a patient and/or recommend a treatment strategy.

Figure 8B:
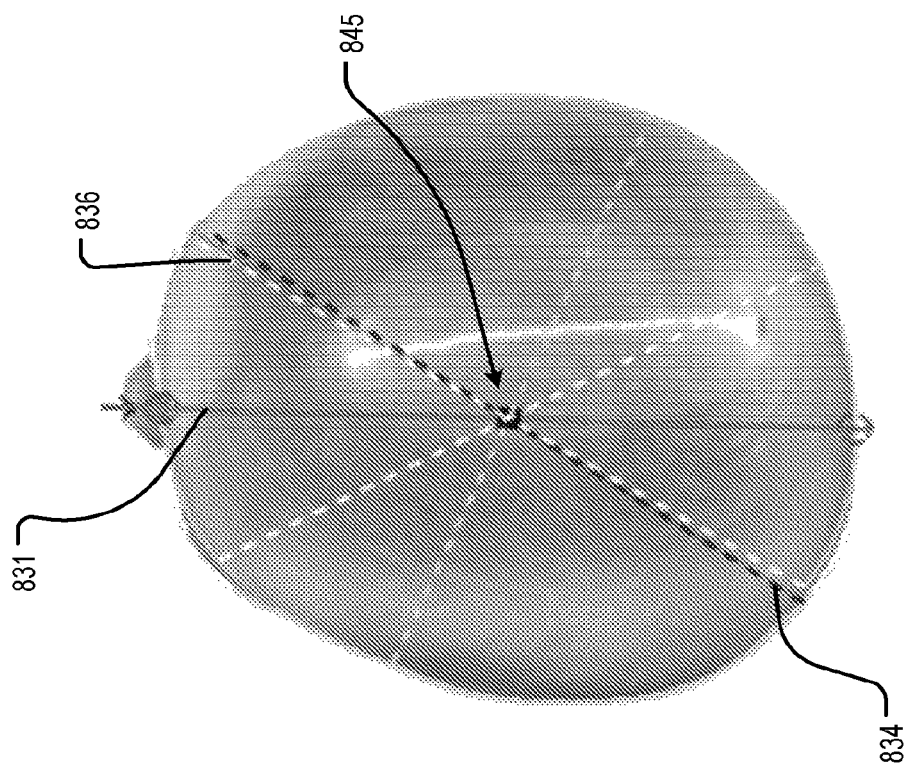
FIG. 8B is an image of a nose direction defined by mid of maximum diagonal of a cranial contour, according to an exemplary embodiment of the present disclosure.
Figure 8A:
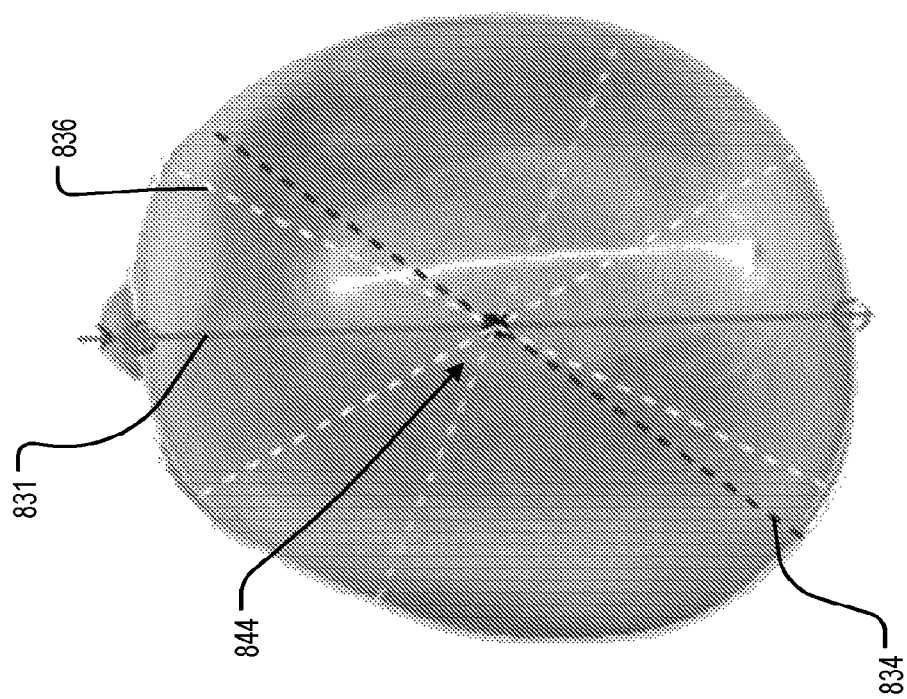
FIG. 8A is an image of a nose direction defined by a center of mass of a cranial contour, according to an exemplary embodiment of the present disclosure.

Referring now to FIG. 8A and FIG. 8B, in view of step 731 of sub process 328, nose direction of a patient can be calculated either based on center of mass or based on a midpoint of a maximum diagonal. FIG. 8A and FIG. 8B are each annotated to illustrate a nose direction 831, a diagonal 836, and a length 834. FIG. 8A, however, illustrates a nose direction calculation according to a center of mass 844 while FIG. 8B shows a nose direction calculation according to a midpoint of maximum length 845, therein illustrating the variation between the approaches in determination of the fundamental cranial parameters of the cranial contour.

FIG. 9A through FIG. 11 illustrate preliminary results of an implementation of the above-described methodology in evaluating cranial shapes of patients. Severity scales were tested using 33 birds' eye view (i.e., top view) images of infants with different forms of FHS and attendant ground truth CI data and 58 birds' eye view images of infants with different types of FHS and attendant ground truth CVAI data acquired via 3D scanners.

Figure 9B:
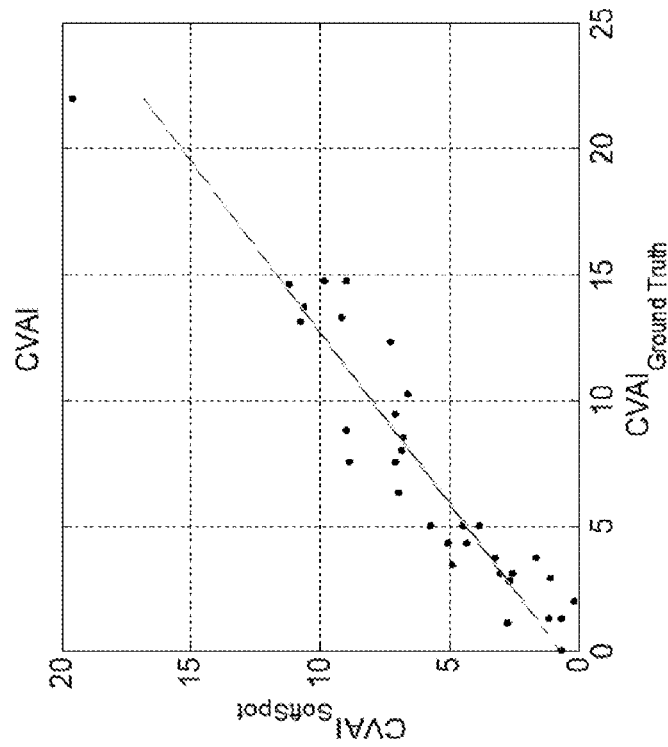
FIG. 9B is a graphical comparison of experimentally determined cranial vault asymmetry index and ground truth cranial vault asymmetry index, according to an exemplary embodiment of the present disclosure.
Figure 9A:
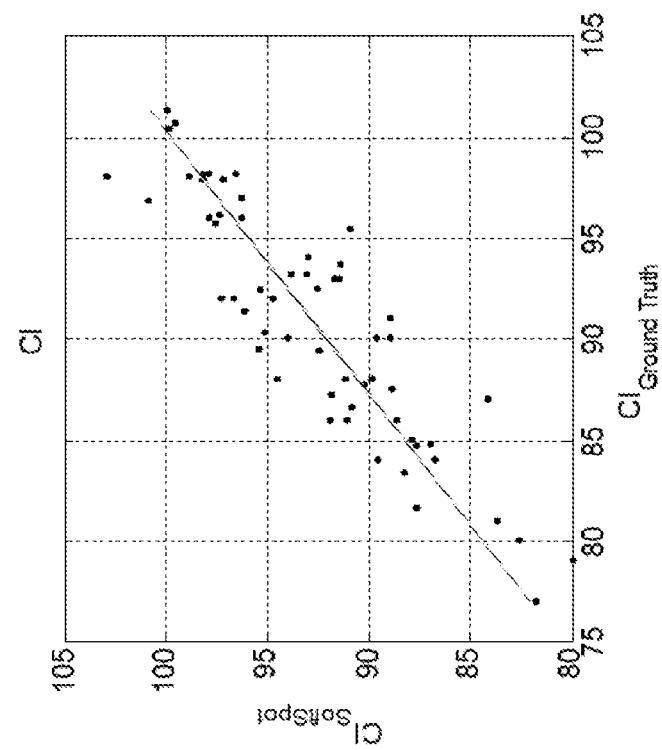
FIG. 9A is a graphical comparison of experimentally determined cephalic index and ground truth cephalic index, according to an exemplary embodiment of the present disclosure.
Figure 10A:
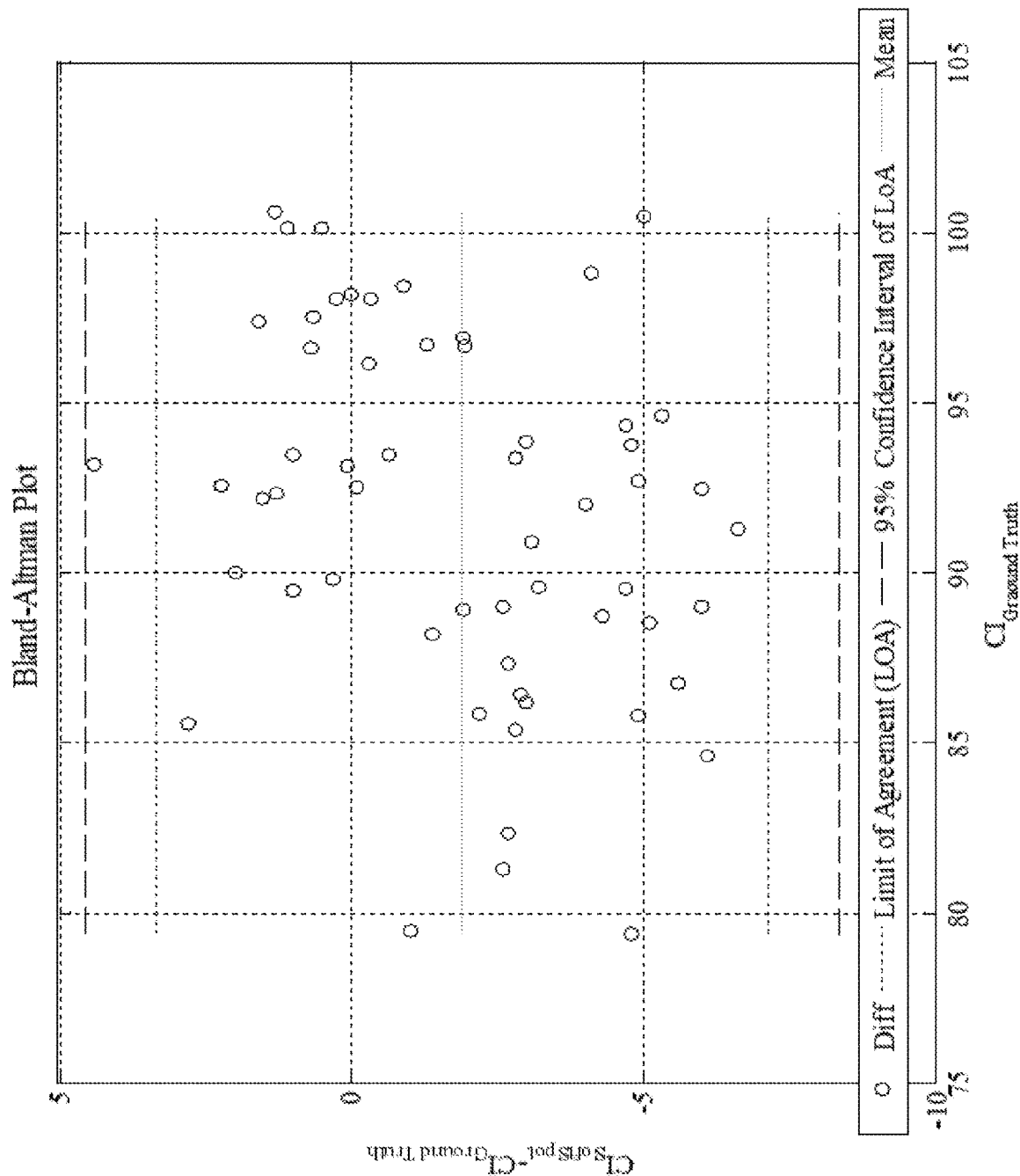
FIG. 10A is a graphical representation of a Bland-Altman Plot comparing experimentally determined cephalic index and ground truth cephalic index, according to an exemplary embodiment of the present disclosure.
Figure 10B:
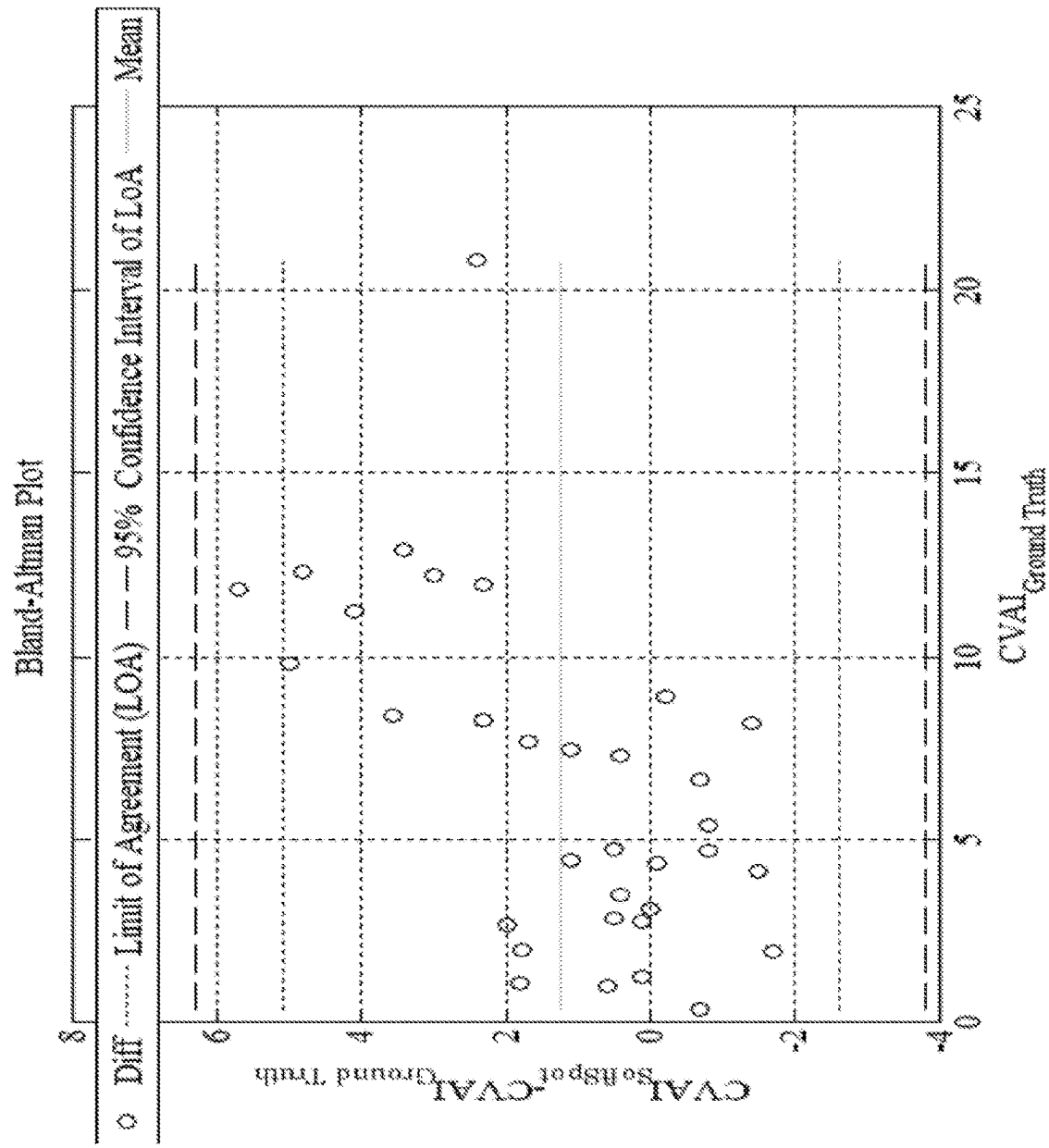
FIG. 10B is a graphical representation of a Bland-Altman Plot comparing experimentally determined cranial vault asymmetry index and ground truth cranial vault asymmetry index, according to an exemplary embodiment of the present disclosure.

As shown in FIG. 9A and FIG. 9B, respectively, the Spearman correlation coefficient between the image-based measurements and the ground-truth data was 0.928 (p<0.001) and 0.909 (p<0.001) for CI and CVAI, demonstrating the high correlation between the two measurements. The error of the image-based method was −1.9±2.6% for CI and 1.2±1.9% for CVAI. All data points lie within the 95% confidence interval of the Limit of Agreement for both CI and CVAI, as shown in FIG. 10A and FIG. 10B.

FIG. 11 is a tabular representation of the above-described results of the Bland-Altman analysis in context of prior work implementing manual human expert measurements.

Figure 12:
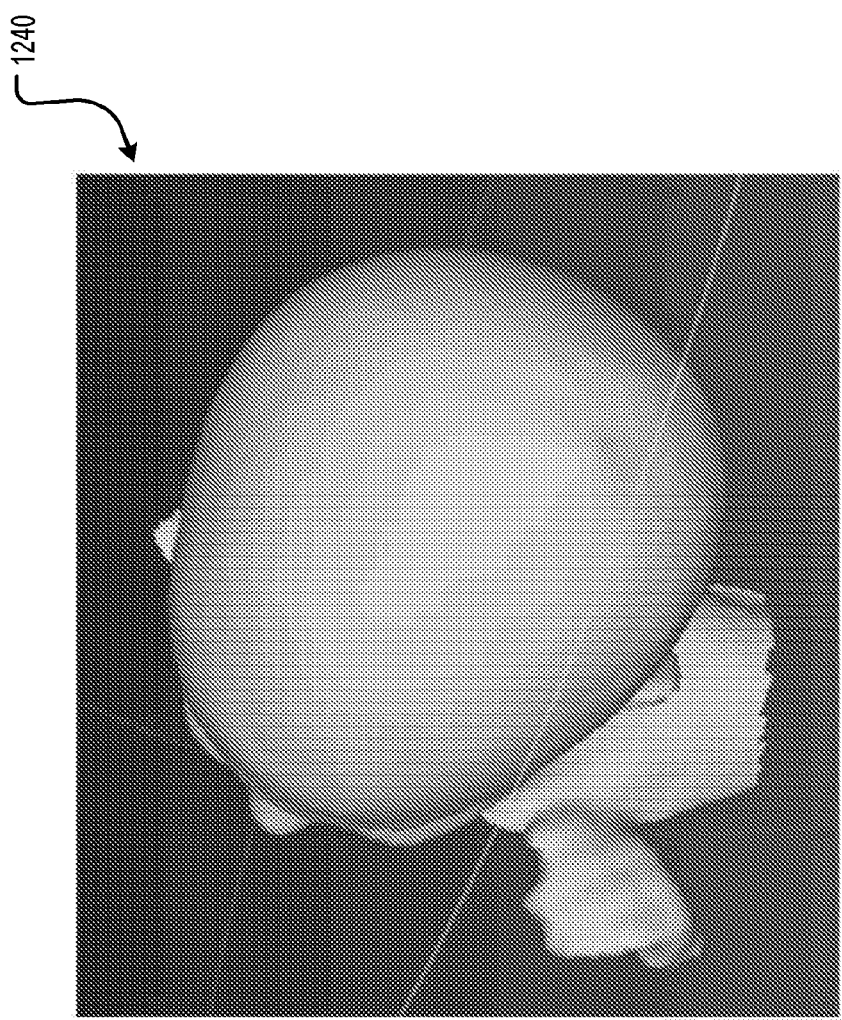
FIG. 12 is an image of a 3D head scan, according to an exemplary embodiment of the present disclosure.

According to an embodiment, the above-implementation of the process for 2D images can be similarly implemented with 3D image datasets. 3D photography or images can be acquired using, for instance, an added depth sensor (e.g., a structured light, built-in depth sensor). FIG. 12 is an exemplary 3D scan 1240 of a head of a patient acquired via added depth sensor.

Figure 13A:
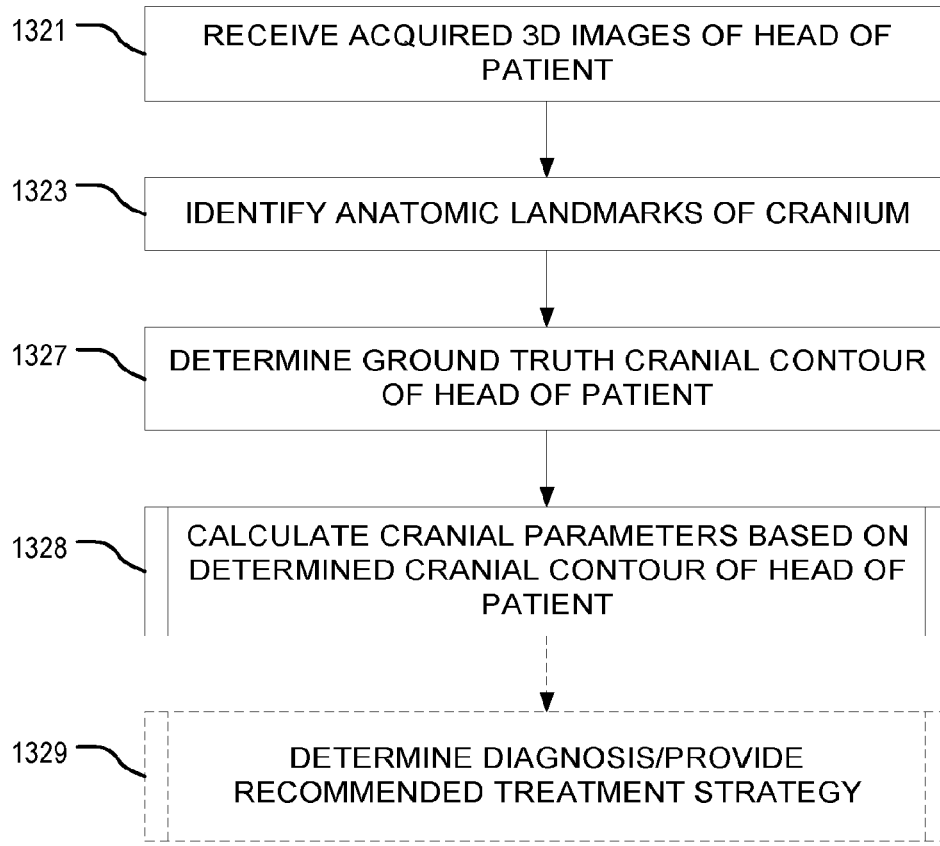
FIG. 13A is a flow diagram of a method of determination of cephalic index, cranial vault asymmetry index, and cranial vault asymmetry, according to an exemplary embodiment of the present disclosure.

Referring now to FIG. 13A, the process described above can be similarly implemented with 3D scans. As shown, at step 1321 of process 300, one or more acquired 3D images of a head of a patient can be received. The one or more acquired 3D images can be acquired by, for instance, a 3D scanner, a plurality of acquired images, or an image sensor, and can comprise depth information. In an embodiment, the image sensor can be integrated within a camera of a smartphone. Each of the one or more acquired images can be 3D images acquired via, for instance, application of structured light. In an embodiment, the 3D images can be 2D images acquired at multiple viewpoints and later stitched together to form a 3D image. In an embodiment, the 3D image can be a time series of images to account for patient movement.

At step 1323 of process 300, the one or more acquired 3D images can be annotated in order to identify anatomical landmarks. In an embodiment, the one or more acquired 3D images can be segmented in order to identify anatomical landmarks on the head of the patient. The segmentation can be an automated process or a semi-automated process. With respect to an automated process, the segmentation can proceed by automatic segmentation methods, such as thresholding, of the image according to known pixel relationships or by application of a machine learning method such as a convolutional neural network, the convolutional neural network being trained to identify an anatomical landmark of an head of a patient. Such machine learning approaches will be described in detail with respect to FIG. 20 through FIG. 23B. With respect to a semi-automated process, the processing circuitry can be configured to receiver a user command indicating where an anatomical landmark of the head of the patient may be.

According to an embodiment, the anatomical landmarks of the cranium can include the left and right tragions, nasion, and subnasale, among others. Such anatomical landmarks can be identified by a user or by a machine learning (e.g. deep learning) and image processing approach, as described above.

According to an embodiment, in order to facilitate acquisition of the 3D scan, the head of the patient may be outfitted with a cap, as previously shown in FIG. 4A and FIG. 4B. An uncovered head of a patient can be seen in FIG. 4A, while FIG. 4B shows a head of a patient covered with a thin cap 441 to smooth the cranial surface and expedite acquisition and processing.

Figure 14:
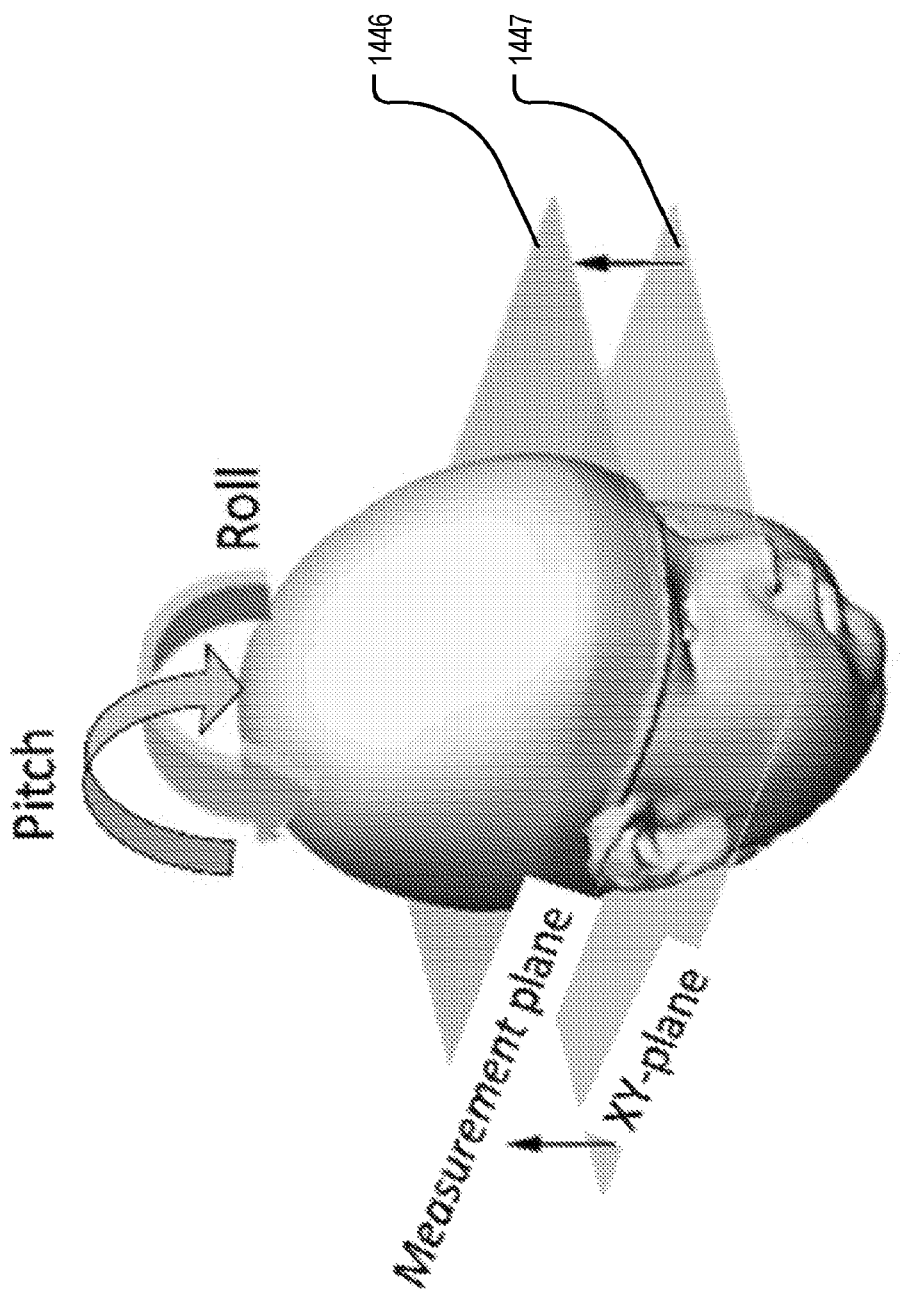
FIG. 14 is an illustration of a measurement plane and camera angle of a 3D scan of a head, according to an exemplary embodiment of the present disclosure.

Based on the above, a cranial contour of the head of the patient can be determined at step 1327 of process 300. In an embodiment, the cranial contour of the head of the patient is a ground truth cranial contour of the head obtained by intersecting a measurement plane, indicated by numeral 1446 in FIG. 14, with the 3D surface of the head of the patient in the 3D image data. In an example, the measurement plane 1446 is a plane that parallels an XY plane, indicated by number 1445 in FIG. 14, at the level of the largest head circumference. As defined above, the XY plane 1445 can be defined based on anatomical landmarks including the left and right tragions, nasion, subnasale, and the like. In an embodiment, the cranial contour of the head of the patient is a head circumference.

At sub process 1328 of process 300, the cranial contour of the head of the patient can be used to determine cranial parameters of the head of the patient. In an embodiment, the cranial parameters can include fundamental parameters such as length, width, right diagonal, left diagonal, circumference, and volume, among others. In an embodiment, the cranial parameters can include complex cranial parameters such as CI, CVA, and CVAI, among others.

At sub process 1329 of process 300, the determined cranial parameters of the head of the patient can be compared with known benchmarks for a specific cranial parameter, and a diagnosis or a recommend treatment can be determined, accordingly. For instance, as described previously, if CI of a head of a patient is less than 75%, the patient can be diagnosed as having scaphocephaly and attendant treatment can be recommended. The treatment may include visiting a physician or surgeon and may include repositioning therapy, as described previously in this disclosure.

Figure 13B:
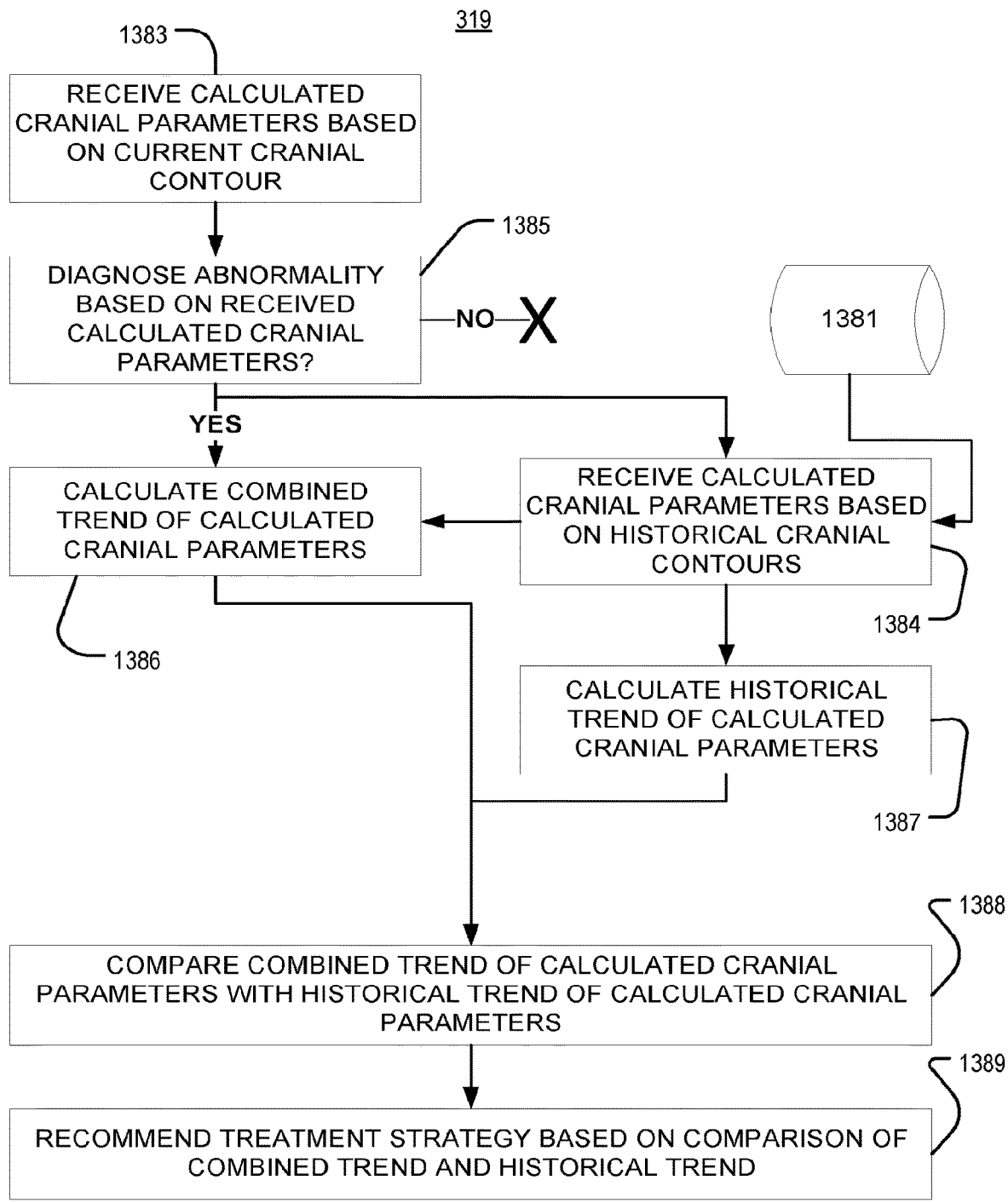
FIG. 13B is a flow diagram of a method of evaluating a determined cephalic index, cranial vault asymmetry index, and cranial vault asymmetry, according to an exemplary embodiment of the present disclosure.

As described in FIG. 13B, and similarly to FIG. 3D, the above-described transient application of the method 300, and sub-process 319, can also be considered in the context of a continuous application, wherein longitudinal data of patient growth is considered. Therefore, FIG. 13B is a flow diagram of sub process 319, wherein determining a diagnosis and providing recommended treatment strategy for a patient with a cranial abnormality can be performed in context of 3D historical patient data.

At step 1383 of sub process 319, calculated cranial parameters (step 318 of process 300), or current cranial parameters, based on the current cranial contour can be received by processing circuitry.

At step 385 of sub process 319, the calculated cranial parameters of the cranial contour can be compared with known benchmarks for cranial abnormalities, such as CI, CVA, and CVAI, and a diagnosis or a recommended treatment can be determined, accordingly. If the calculated cranial parameters do not meet a pre-determined benchmark for a positive diagnosis, sub process 319 may end. If, however, the calculated cranial parameters meet the pre-determined benchmark for the positive diagnosis of a cranial abnormality, sub process 319 can proceed.

At step 1384 of sub process 319, calculated cranial parameters based on historical cranial contours, or historical cranial parameters, can be received from a database (e.g., local server or remote server 1381), where historical, or longitudinal, patient data can be stored.

At step 1386 of sub process 319, the current cranial parameters can be appended to the historical cranial parameters and a combined cranial model can be generated, the combined cranial model indicating a trend of the cranial parameters over time.

Similarly, at step 1387 of sub process 319, a model of the historical cranial parameters can be generated, the historical cranial model indicating a trend of the cranial parameters up to and excluding the current calculation of cranial parameters.

Accordingly, at step 1388 of sub process 319, the combined cranial model and the historical cranial model can be compared to determine, for instance, differences between the curves of the models. Moreover, the curves can be used to estimate future parameters of the cranial contour, providing predictive power in evaluating the progression of diagnosis of a patient.

In this way, as at step 389 of sub process 319, it may be possible to determine if a therapy, such as repositioning therapy, has been effective or if the subject is growing within healthy parameters. For instance, though a patient may continue to be diagnosed as having a cranial abnormality, a comparison of the combined cranial model and the historical cranial model may indicate that the cranial abnormality is improving and the current therapy should continue. Alternatively, the comparison of the combined cranial model and the historical cranial model may indicate that the cranial abnormality is worsening and that an alternative treatment, such as a surgical intervention, should be considered and/or recommended, and pursued. Alternatively, the model can be used to monitor normal infant growth.

Figure 13C:
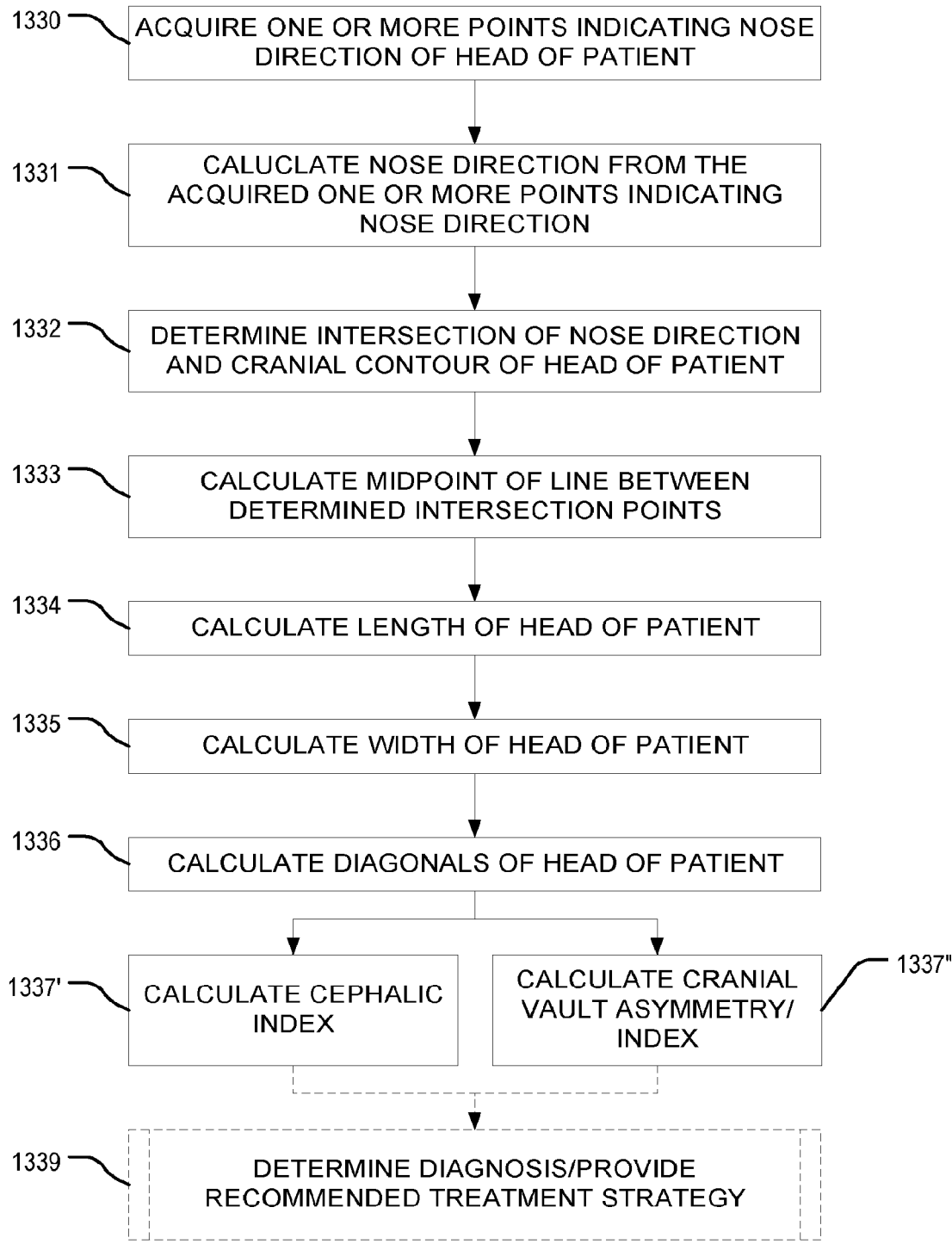
FIG. 13C is a flow diagram of a method of determination of cephalic index, cranial vault asymmetry index, and cranial vault asymmetry, according to an exemplary embodiment of the present disclosure.

With reference now to FIG. 13C, and in view of sub process 1328 of FIG. 13A, calculations can be performed on the generated cranial contour in order to calculate a subset of the fundamental and complex cranial parameters for sub process 1328.

First, at step 1330 of sub process 1328, a landmark, such as a nose of a patient, can be selected as an anatomical reference. The nose can be indicated by a user, can be identified using image classification via machine learning, or can be identified by identifying a maximum radius of curvature on the cranial contour as P1.

At step 1331 of sub process 1328, nose direction can be determined from the selected one or more points of step 1330. In an embodiment, a center of mass of the cranial contour can be identified as P2 and nose direction ($\theta_{nose}$) can be calculated, therefrom. In an embodiment, the midpoint of the longest diagonal of the cranial contour or the midpoint of a diagonal that divides the head area in half can be identified as P2.

At step 1332 of sub process 1328, an intersection of the nose direction and the cranial contour can be defined as P3 and P4.

At step 1333 of sub process 1328, the midpoint of a line formed between P3 and P4 can be defined as P5.

At step 1334 of sub process 1328, length (L) of the head of the patient can be calculated as the length of a line inside the cranial contour with maximum length that has an angle $\theta$, where $\theta_{nose}-1 \leq \theta \leq \theta_{nose}+1$, and the line passes through point P5.

At step 1335 of sub process 1328, width (W) of the head of the patient can be calculated as the length of a line inside the cranial contour perpendicular to L that passes through point P5.

At step 1336 of sub process 1328, the diagonals ($D_R$, $D_L$) can be calculated as the length of one or more lines inside the cranial contour that have $\alpha$ and $-\alpha$ degrees angles relative to $\theta_{nose}$ and pass through point P5, where a is either {30, 40, 45}.

At step 1337' of sub process 1328, CI, an exemplary cranial parameter, can be calculated as CI=W/L.

At step 1337" of sub process 1328, CVAI, an exemplary cranial parameter, can be calculated as $$CVAI = \frac{|D_R - D_L|}{\max(D_R, D_L)}.$$

The above-calculated cranial parameters can then be used at step 1339 of sub process 1328 to determine a diagnosis of a patient and/or recommend a treatment strategy.

In an embodiment, and because the use of 3D scanning allows for the collection of depth dependent measurements, CVA can also be calculated as CVA=$|D_R-D_L|$.

Figure 15:
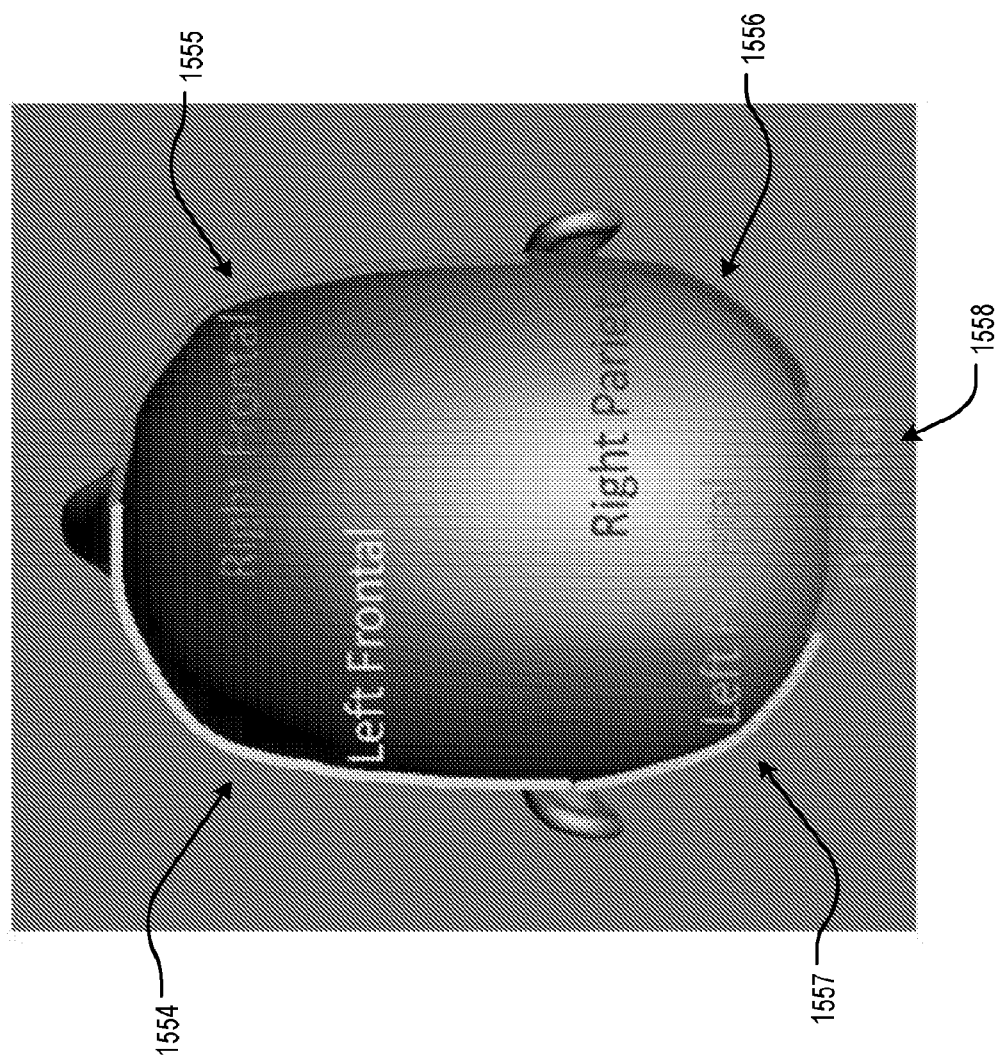
FIG. 15 is an image of curvature features that can be extracted from a head curve, according to an exemplary embodiment of the present disclosure.

According to an embodiment of the present disclosure, FIG. 15 is an illustration of curvature features that can be extracted from each segment of a cranial contour. As shown, such curvature features include left frontal 1554, right frontal 1555, right parietal 1556, occipital 1558, and left parietal 1557.

Additionally, metrics other than local shape (e.g., curvature, shape index), such as malformation or deviation from normal shape (based on normative data), circularity, blobness, and the like, can be derived from 2D curves or 3D surfaces and similarly computed.

Figure 16B:
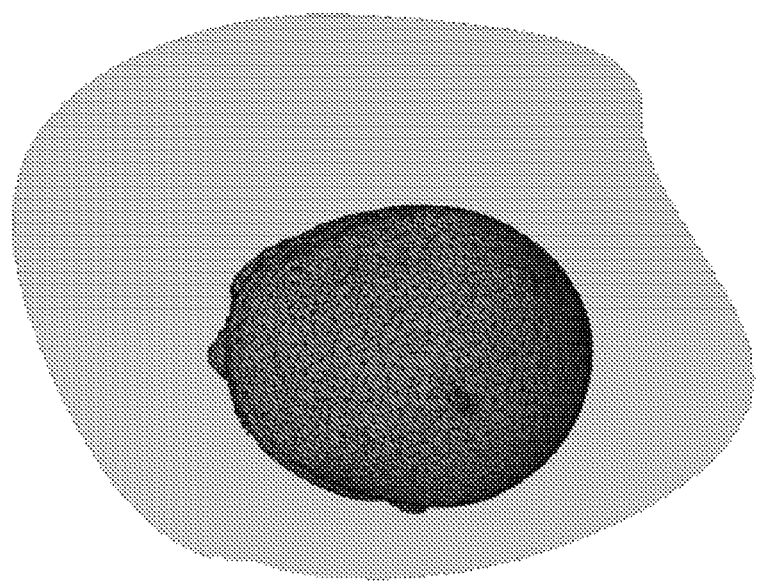
FIG. 16B is an image of a perspective of a head of a patient wearing a custom cap, according to an exemplary embodiment of the present disclosure.
Figure 16A:
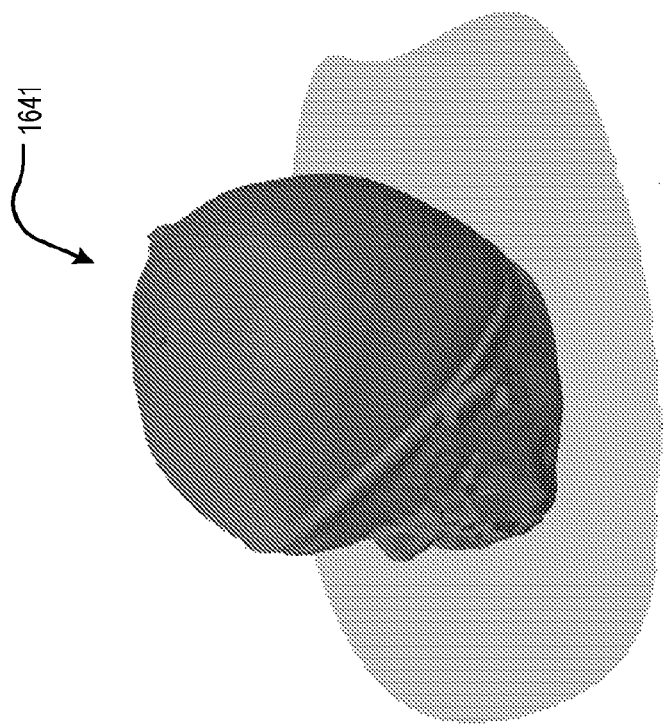
FIG. 16A is an image of a perspective of a head of a patient wearing a custom cap, according to an embodiment of the present disclosure.

According to an embodiment of the present disclosure, the cap can be designed such that a center portion is thin and stretchy, similar to a stocking cap that covers the head to the ears and nose while allowing the baby to easily breath. As shown in FIG. 16A and FIG. 16B, the surrounding of the cap 1641 can stay relatively rigid (like a sun hat) or non-rigid but can extend well beyond the center of the cap 1641. The color of the center of the cap 1641 can be easily distinguishable from the surrounding. The hands of a parent or guardian or a nurse can be placed/hidden under the surrounding part to hold the chin gently to avoid head movement. In another embodiment, the cap 1641 can be only the central part with no surrounding. However, due to the strong contrast with a normal background, it would be expected to remain easily segmentable using methods such as graph cut and the like.

Figure 17B:
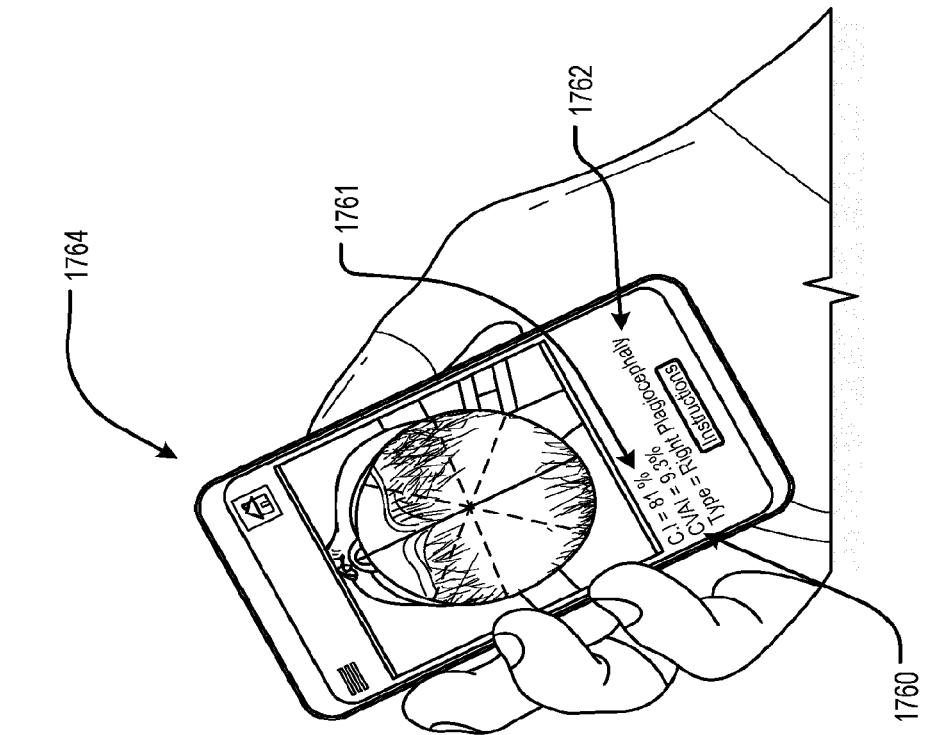
FIG. 17B is an illustration of a mobile app employing system and methods for determining cephalic index and cranial vault asymmetry index of a head of a patient, according to an exemplary embodiment of the present disclosure.
Figure 17A:
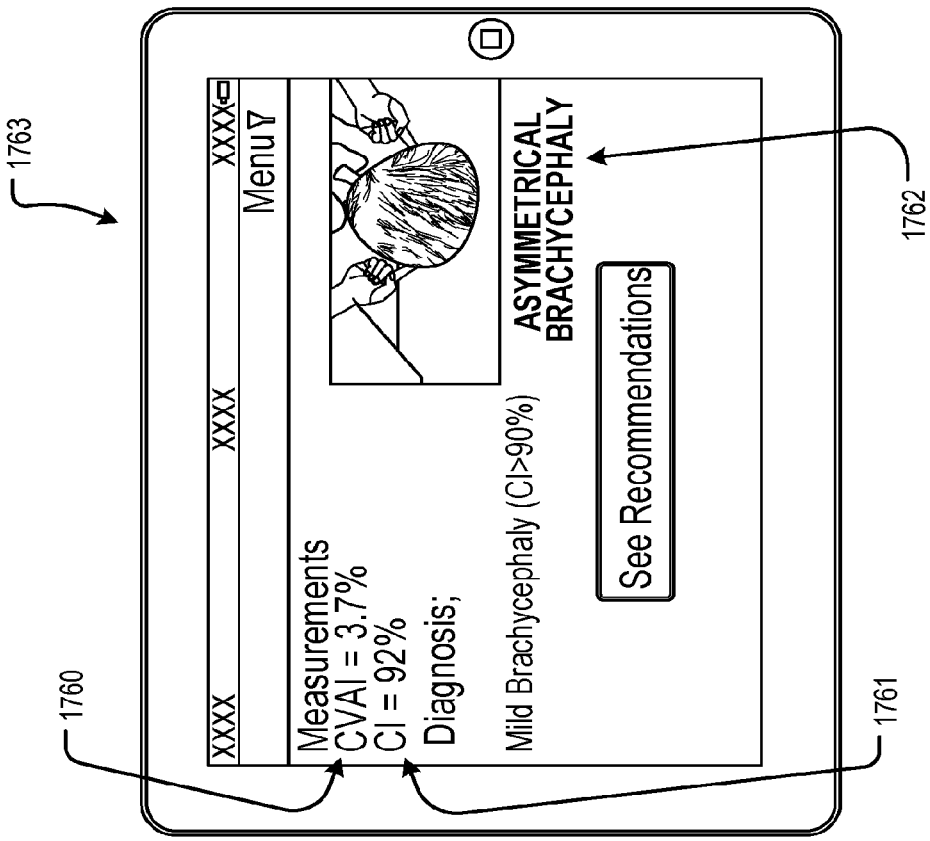
FIG. 17A is an illustration of a mobile app employing system and methods for determining cephalic index and cranial vault asymmetry index of a head of a patient, according to an exemplary embodiment of the present disclosure.

According to an embodiment, the above-described method of the present disclosure can be implemented on a device having necessary components and circuitry configured for, at least, image processing of acquired images of a region of a body of a patient. In an embodiment, the region of the body of the patient is a head of a patient. Accordingly, FIG. 17A and FIG. 17B are representative illustrations of mobile devices suitable for such a method. Regarding FIG. 17A, the mobile device can be a tablet 1763. The tablet 1763 can have a standard camera, a built-in depth sensor or structured light projector, an externally-coupled depth sensor or structured light projector, a stereoscopic camera, or a 3D photographic device. Regarding FIG. 17B, the mobile device can be a smartphone 1764. The smartphone 1764 can have a standard camera, a built-in depth sensor or structured light projector, an externally-coupled depth sensor or structured light projector, a stereoscopic camera, or a 3D photographic device. Both the tablet 1763 and the smartphone 1764 can be controlled by a user interface displayed on a display of the mobile device. In an example, the user interface can be a mobile application user interface, as described with respect to FIG. 18A through FIG. 18H.

As shown in FIG. 17A, a user interface of the tablet 1763 can provide calculations as to, in the case of head shape, CVAI 1760 and CI 1761, as well as a preliminary diagnosis 1762 of the patient based upon these factors. In an instance when CI 1761 is greater than 90%, the patient can be preliminarily diagnosed as having asymmetrical brachycephaly.

As shown in FIG. 17B, a user interface of the smartphone 1764 can provide calculations as to, in the case of head shape, CVAI 1760 and CI 1761, as well as a preliminary diagnosis 1762 of the patient based upon these factors. In an instance when CVAI 1760 is greater than 3.5%, the patient can be preliminarily diagnosed as having right plagiocephaly.

A more detailed workflow of a mobile application user interface implemented in cooperation with the method of the present disclosure will now be described with reference to FIG. 18A through FIG. 18H.

Figures 18A, 18B, 18C, 18D:
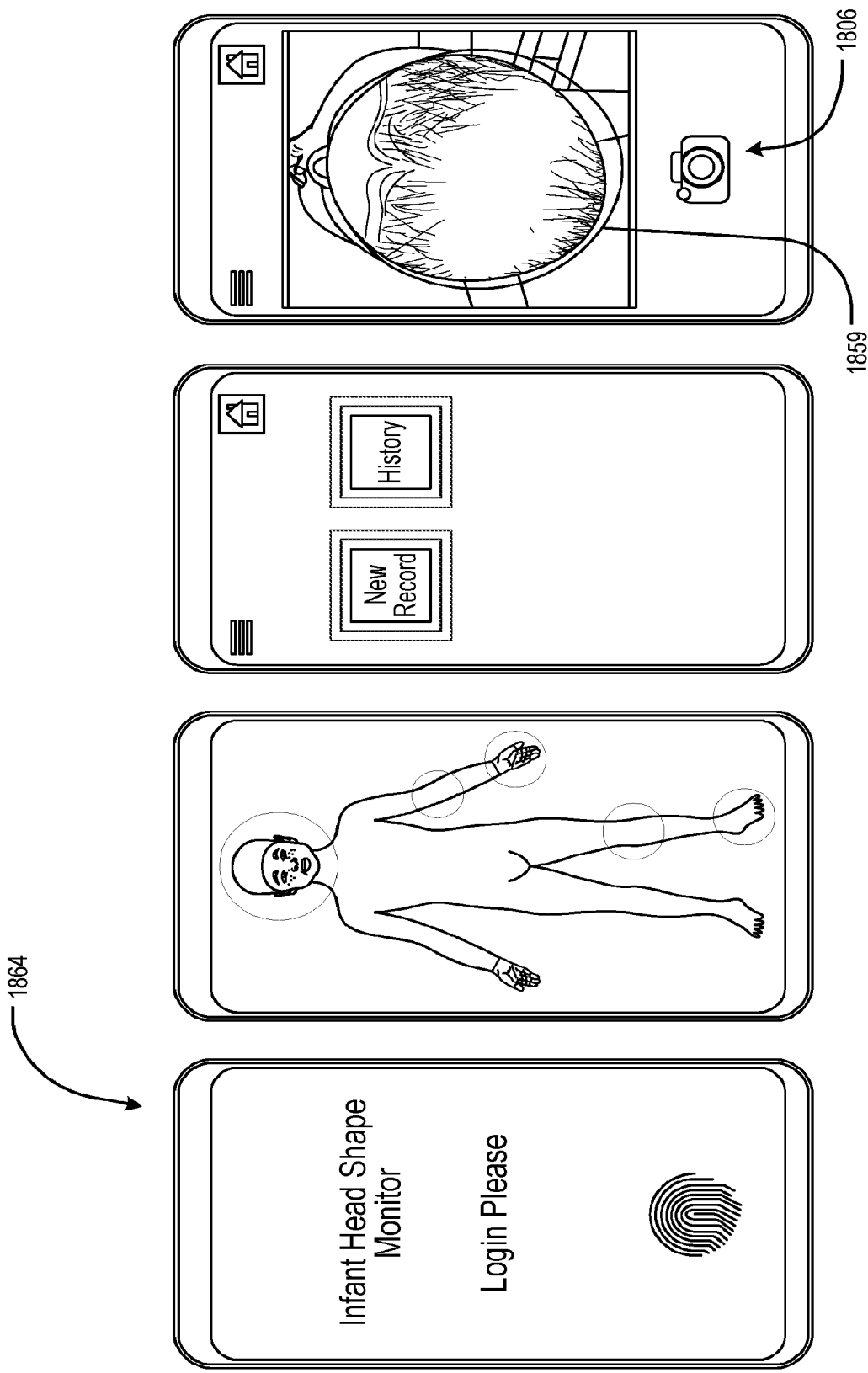
FIG. 18A is an illustration of a workflow event of a mobile app employing system and methods for determining cephalic index and cranial vault asymmetry index of a head of a patient, according to an exemplary embodiment of the present disclosure.
FIG. 18B is an illustration of a workflow event of a mobile app employing system and methods for determining cephalic index and cranial vault asymmetry index of a head of a patient, according to an exemplary embodiment of the present disclosure.
FIG. 18C is an illustration of a workflow event of a mobile app employing system and methods for determining cephalic index and cranial vault asymmetry index of a head of a patient, according to an exemplary embodiment of the present disclosure.
FIG. 18D is an illustration of a workflow event of a mobile app employing system and methods for determining cephalic index and cranial vault asymmetry index of a head of a patient, according to an exemplary embodiment of the present disclosure.

As shown in FIG. 18A, the mobile application user interface can be implemented on a tablet 1863 and can include a login page, wherein a user can create user credentials or login via an Internet account such as a social-medial account (e.g., Facebook) or an e-mail account (e.g., Google). Logging in allows the user to store any and all user data for future diagnostic evaluation or longitudinal patient monitoring. Alternatively, the user can login as a guest, in which case the acquired images and diagnoses will be a onetime experience and any user data will be erased following the session.

As shown in FIG. 18B, having logged in, a screen can displayed asking the user to identify a part of the body to be imaged or reviewed. As shown in FIG. 18C, the user may then select whether a new diagnostic session is desired or if a review of past session is desired. If, for example, a new diagnostic session is desired and the identified part of the body is the head, a camera icon 1806 can be displayed, as shown in FIG. 18D. Alongside the camera icon 1806, a mock head contour, or mock cranial contour 1859, can be displayed. It can be appreciated that, in cases of an ear, lower extremities, upper extremities, facial deformities, and the like, similar patterns may be augmented for assistance. In the case displayed in FIG. 18D and FIG. 18E, this assistance allows the user to place the camera of the tablet (or other smart device) near the optimum focal distance to allow for maximum image resolution (though the focal distance does not matter in calculation of CI/CVAI using the method described herein). During image acquisition, as illustrated in FIG. 18D, several embodiments can be considered when acquiring images, including 1) a single birds eye view image, 2) multiple birds' eye view images, 3) multiple images at different angles of the head (i.e., birds' eye, side, front, back, etc.), 4) a video image of the head, 5) a 3D image captured using a front or back depth sensor or dual/multiple camera in front or back. In an embodiment, the user captures necessary images via manual or automatic image capture mode. In automatic image capture mode, a partial sphere, described previously, with ±30 degree, for example (i.e. FIG. 6B), can be augmented on the display during acquisition of one or more images, helping the user to acquire images in all directions to compensate for the shooting angle error (i.e. a view other than true top view, or birds' eye view, wherein both ears and tip of the nose visible and no forehead). In an embodiment, the partial sphere can be +/−45°. A cap with custom designed markers may be necessary to facilitate acquisition of images across the entire partial sphere. After acquiring images according to the augmented partial sphere, the camera icon 1806 may be illuminated as green when all potentially relevant shooting angles have been acquired. In manual image capture mode, the user can manually capture each of the one or more images. Voice control may also assist the user during image capturing.

Figures 18E, 18F, 18G, 18H:
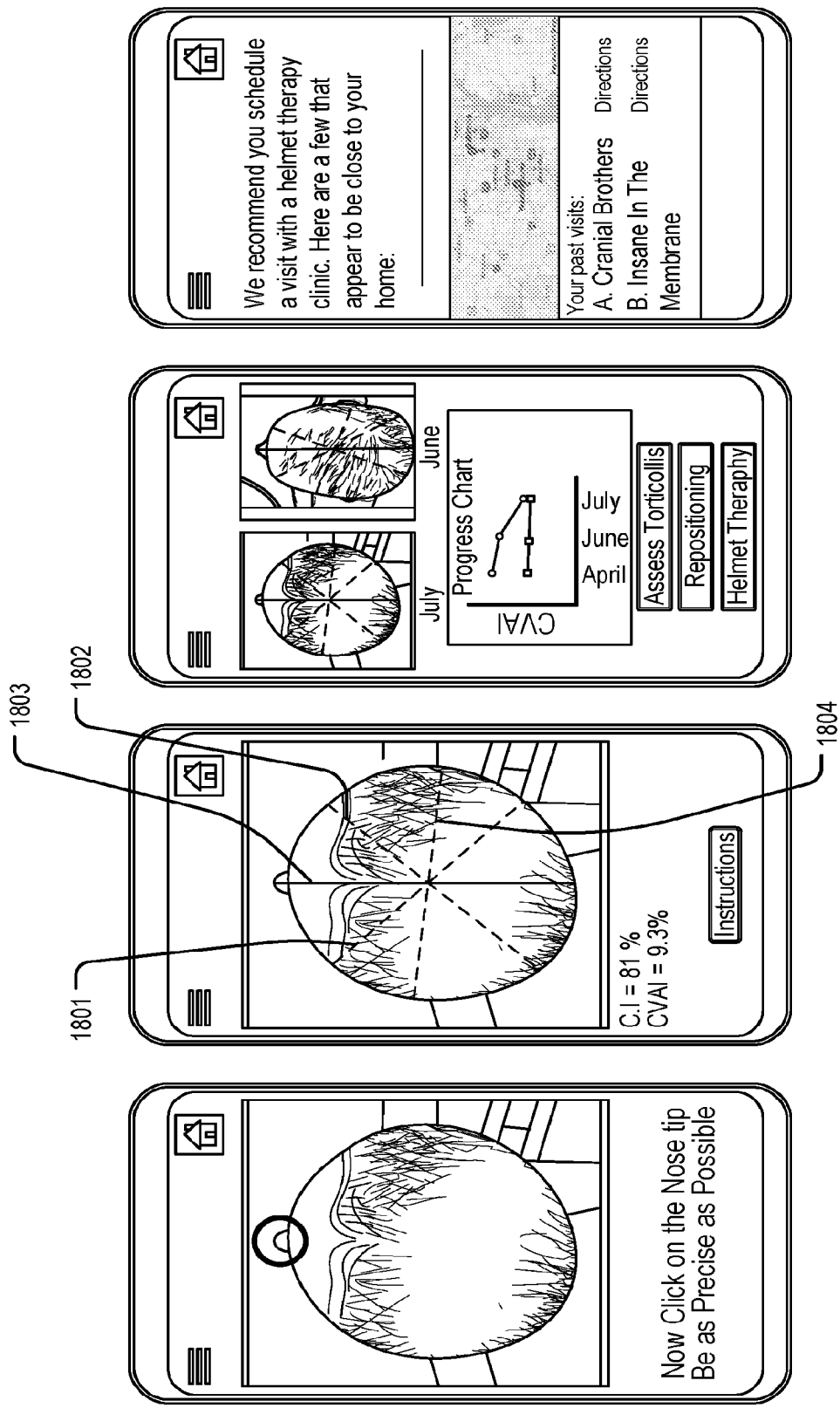
FIG. 18E is an illustration of a workflow event of a mobile app employing system and methods for determining cephalic index and cranial vault asymmetry index of a head of a patient, according to an exemplary embodiment of the present disclosure.
FIG. 18F is an illustration of a workflow event of a mobile app employing system and methods for determining cephalic index and cranial vault asymmetry index of a head of a patient, according to an exemplary embodiment of the present disclosure.
FIG. 18G is an illustration of a workflow event of a mobile app employing system and methods for determining cephalic index and cranial vault asymmetry index of a head of a patient, according to an exemplary embodiment of the present disclosure.
FIG. 18H is an illustration of a workflow event of a mobile app employing system and methods for determining cephalic index and cranial vault asymmetry index of a head of a patient, according to an exemplary embodiment of the present disclosure.

As described with reference to the flow diagrams, having acquired the necessary images of the patient, the user may select landmarks on one or more of the acquired images, the landmarks including, among others, the ears, the nose, and the eyebrows on the forehead. As shown in FIG. 18E, the selected landmark can be the tip of the nose of the patient.

As shown in FIG. 18F, the selected landmark can then be used to determine a cranial contour of the head of the patient.

From this, cranial parameters such as a length 1803, a width 1804, a minimum diagonal 1801, and a maximum diagonal 1802 can be calculated.

Moreover, these fundamental cranial parameters can be used to calculate more complex cranial parameters such as CI, CVA, CVAI, head circumference, head volume, and craniosynostosis type, as well as ear deformity type and other metrics of deformities of the lower and upper extremities. As shown in FIG. 18F, the user may be presented with CI and CVAI, indicating, for example, that the patient may have a form of plagiocephaly. Results can be displayed to the user with interactive buttons to "send", "save", and "see instructions", with an estimation of error range or reliability score.

As shown in FIG. 18G, these results can be used to generate a recommendation. The recommendation can included specific repositioning therapy recommendations or pediatrician or orthoptist/physiotherapist visit scheduling. These results can also include displaying a graph of cranial parameters including CVAI, CI, CVA, and circumference as a function of time to allow longitudinal evaluation. This graphical data can be supported by a sequence of photos that illustrate the patient's head in a time-matched chronological manner. Moreover, the user can save/delete the results, view additional plots of the measurements over time, share the results with their physician, chat with an online specialist, schedule appointments, or watch related and personalized educational materials and resources. The app may also send automated reminders to ensure parents compliance with best repositioning practices customized based on the measurements' history.

As shown in FIG. 18H, a list of medical professionals with their office hours and geographical locations can be shown to the user. The list can be based on the area code of the user which may be found automatically by the app or input manually by the user.

According to an embodiment, the user interface may instruct and permit a user to acquire and/or upload one or more images of the head of the user. To this end, the user interface may guide the user in acquiring the best possible image both by showing samples of desired images and by processing the current image and measuring its accuracy. The user interface may also use voice control to start or stop photo/video acquisition.

In an embodiment, the user interface may offer manual and/or automatic image acquisition. For automated acquisition, a partial sphere (e.g. ±30 degree) can be augmented on the screen during image (i.e., video or photo) acquisition, thereby aiding the user in acquiring photos in order to compensate for shooting angle error. A cap with custom designed markers may be used to ensure acquisition of the entire partial sphere. An icon displayed via the user interface may be illuminated as green once the user has acquired the entire partial sphere.

In an embodiment, the user may then be asked to determine one or more anatomical landmarks on the photo that will be used to initialize the segmentation and/or indices calculations. After the calculations are complete, the software application may display the results to the user, the results including the type and severity of FHS, if present. The user interface can then provide the user the option to (1) save the results, and/or (2) send to a primary care physician, and/or (3) receive instructions on corresponding repositioning methods, and/or (4) view a list of medical professionals near their current or desired location.

In an embodiment, the software application may also provide the option to graphically display the longitudinal growth of, for example, an infant's head shape.

In addition, the software application may use a 3D image to perform the calculations. This image may be acquired using a built in 3D camera/depth sensor on a smart device or an add-on 3D camera. In an embodiment, the 3D image can be constructed by combining images from several 2D photographs or by a video recorded by rotating the camera around the head. The software application with 3D camera may report the CI, CVA, and CVAI indices at different depths. The 3D images may be transmitted to a remote server, or cloud-based server, via wireless communication method and processing may be performed therein, the results of which being transmitted back to the user's device for display via the user interface. Alternatively, the calculations may be performed locally on the user device.

In an embodiment, the software application may also provide, for instance, the circumference of the head. This circumference may represent or correlate with the head circumference that a pediatrician may measure during a doctor's visit.

In an embodiment, the software application can provide head volume when a 3D sensor is used.

In an embodiment, the software application can display multiple icons indicating different deformities of the body including, among others, the head (i.e., FHS, craniosynostosis), the legs, the fingers, and the ears.

In an embodiment, the software application may also monitor a mileage a parent drives with an infant and may alert the parent to reposition the baby during longer trips.

Figure 19:
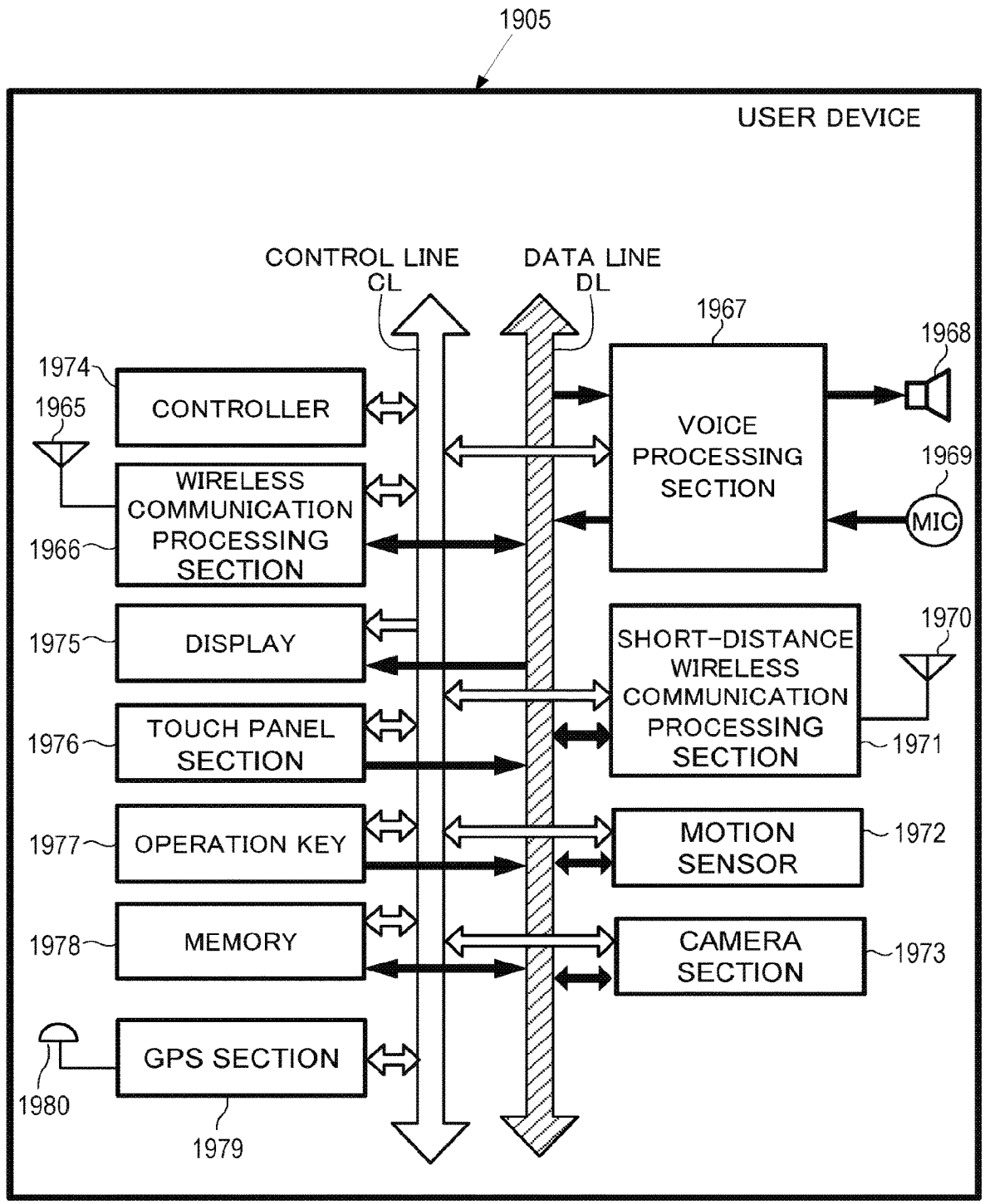
FIG. 19 is a hardware description of a mobile device, according to an exemplary embodiment of the present disclosure.

FIG. 19 is a more detailed block diagram illustrating an exemplary user device 1905, or mobile device, according to certain embodiments of the present disclosure. In certain embodiments, user device 1905 may be a smartphone. However, the skilled artisan will appreciate that the features described herein may be adapted to be implemented on other devices (e.g., a laptop, a tablet, a server, an e-reader, a camera, a navigation device, etc.). The exemplary user device 1905 of FIG. 19 includes a controller 1974 and a wireless communication processor 1966 connected to an antenna 1965. A speaker 1968, or an output device, and a microphone 1969 are connected to a voice processor 1967.

The controller 1974 is an example of a control unit and may include one or more central processing units (CPUs) and/or one or more graphics processing units (GPUs), and may control each element in the user device 1905 to perform functions related to communication control, audio signal processing, control for the audio signal processing, still and moving image processing and control, and other kinds of signal processing. The controller 1974 may perform these functions by executing instructions stored in a memory 1978. Alternatively or in addition to the local storage of the memory 1978, the functions may be executed using instructions stored on an external device accessed on a network or on a non-transitory computer readable medium.

The memory 1978 is an example of a storage unit and includes but is not limited to Read Only Memory (ROM), Random Access Memory (RAM), or a memory array including a combination of volatile and non-volatile memory units. The memory 1978 may be utilized as working memory by the controller 1974 while executing the processes and algorithms of the present disclosure. Additionally, the memory 1978 may be used for long-term storage, e.g., of image data and information related thereto. As disclosed above, the memory 1978 may be configured to store longitudinal patient information including anatomical measurements or, in an example, cranial parameters.

The user device 1905 includes a control line CL and data line DL as internal communication bus lines. Control data to/from the controller 1974 may be transmitted through the control line CL. The data line DL may be used for transmission of voice data, display data, etc.

The antenna 1965 transmits/receives electromagnetic wave signals between base stations for performing radio-based communication, such as the various forms of cellular telephone communication. The wireless communication processor 1966 controls the communication performed between the user device 1905 and other external devices via the antenna 1965. For example, the wireless communication processor 1966 may control communication between base stations for cellular phone communication.

The speaker 1968 emits an audio signal corresponding to audio data supplied from the voice processor 1967. The microphone 1969 detects surrounding audio and converts the detected audio into an audio signal. The audio signal may then be output to the voice processor 1967 for further processing. The voice processor 1967 demodulates and/or decodes the audio data read from the memory 1978 or audio data received by the wireless communication processor 1966 and/or a short-distance wireless communication processor 1971. Additionally, the voice processor 1967 may decode audio signals obtained by the microphone 1968.

The exemplary user device 1905 may also include a display 1975, a touch panel 1976, an operation key 1977, and a short-distance communication processor 1971 connected to an antenna 1970. The display 1975 may be a Liquid Crystal Display (LCD), an organic electroluminescence display panel, or another display screen technology. In addition to displaying still and moving image data, the display 1975 may display operational inputs, such as numbers or icons which may be used for control of the user device 1905. The display 1975 may additionally display a GUI for a user to control aspects of the user device 1905 and/or other devices. Further, the display 1975 may display characters and images received by the user device 1905 and/or stored in the memory 1978 or accessed from an external device on a network. For example, the user device 1905 may access a network such as the Internet and display text and/or images transmitted from a Web server.

The touch panel 1976 may include a physical touch panel display screen and a touch panel driver. The touch panel 1976 may include one or more touch sensors for detecting an input operation on an operation surface of the touch panel display screen. The touch panel 1976 also detects a touch shape and a touch area. Used herein, the phrase "touch operation" refers to an input operation performed by touching an operation surface of the touch panel display with an instruction object, such as a finger, thumb, or stylus-type instrument. In the case where a stylus or the like is used in a touch operation, the stylus may include a conductive material at least at the tip of the stylus such that the sensors included in the touch panel 1976 may detect when the stylus approaches/contacts the operation surface of the touch panel display (similar to the case in which a finger is used for the touch operation).

One or more of the display 1975 and the touch panel 1976 are examples of a touch screen panel display as might be implemented according to the present disclosure.

In certain aspects of the present disclosure, the touch panel 1976 may be disposed adjacent to the display 1975 (e.g., laminated) or may be formed integrally with the display 1975. For simplicity, the present disclosure assumes the touch panel 1976 is formed integrally with the display 1975 and therefore, examples discussed herein may describe touch operations being performed on the surface of the display 1975 rather than the touch panel 1976. However, the skilled artisan will appreciate that this is not limiting.

For simplicity, the present disclosure assumes the touch panel 1976 is a capacitance-type touch panel technology. However, it should be appreciated that aspects of the present disclosure may easily be applied to other touch panel types (e.g., resistance-type touch panels) with alternate structures. In certain aspects of the present disclosure, the touch panel 1976 may include transparent electrode touch sensors arranged in the X-Y direction on the surface of transparent sensor glass.

The touch panel driver may be included in the touch panel 1976 for control processing related to the touch panel 1976, such as scanning control. For example, the touch panel driver may scan each sensor in an electrostatic capacitance transparent electrode pattern in the X-direction and Y-direction and detect the electrostatic capacitance value of each sensor to determine when a touch operation is performed. The touch panel driver may output a coordinate and corresponding electrostatic capacitance value for each sensor. The touch panel driver may also output a sensor identifier that may be mapped to a coordinate on the touch panel display screen. Additionally, the touch panel driver and touch panel sensors may detect when an instruction object, such as a finger is within a predetermined distance from an operation surface of the touch panel display screen. That is, the instruction object does not necessarily need to directly contact the operation surface of the touch panel display screen for touch sensors to detect the instruction object and perform processing described herein. For example, in certain embodiments, the touch panel 1976 may detect a position of a user's finger around an edge of the display panel 1975 (e.g., gripping a protective case that surrounds the display/touch panel). Signals may be transmitted by the touch panel driver, e.g. in response to a detection of a touch operation, in response to a query from another element based on timed data exchange, etc.

The touch panel 1976 and the display 1975 may be surrounded by a protective casing, which may also enclose the other elements included in the user device 1905. In certain embodiments, a position of the user's fingers on the protective casing (but not directly on the surface of the display 1975) may be detected by the touch panel 1976 sensors. Accordingly, the controller 1974 may perform display control processing described herein based on the detected position of the user's fingers gripping the casing. For example, an element in an interface may be moved to a new location within the interface (e.g., closer to one or more of the fingers) based on the detected finger position.

Further, in certain embodiments, the controller 1974 may be configured to detect which hand is holding the user device 19, based on the detected finger position. For example, the touch panel 1976 sensors may detect a plurality of fingers on the left side of the user device 1905 (e.g., on an edge of the display 1975 or on the protective casing), and detect a single finger on the right side of the user device 1905. In this exemplary scenario, the controller 1974 may determine that the user is holding the user device 1905 with his/her right hand because the detected grip pattern corresponds to an expected pattern when the user device 1905 is held only with the right hand.

The operation key 1977 may include one or more buttons or similar external control elements, which may generate an operation signal based on a detected input by the user. In addition to outputs from the touch panel 1976, these operation signals may be supplied to the controller 1974 for performing related processing and control. In certain aspects of the present disclosure, the processing and/or functions associated with external buttons and the like may be performed by the controller 1974 in response to an input operation on the touch panel 1976 display screen rather than the external button, key, etc. In this way, external buttons on the user device 1905 may be eliminated in lieu of performing inputs via touch operations, thereby improving water-tightness.

The antenna 2070 may transmit/receive electromagnetic wave signals to/from other external apparatuses, and the short-distance wireless communication processor 1971 may control the wireless communication performed between the other external apparatuses. Bluetooth, IEEE 802.11, and near-field communication (NFC) are non-limiting examples of wireless communication protocols that may be used for inter-device communication via the short-distance wireless communication processor 1971.

The user device 1905 may include a motion sensor 1972. The motion sensor 1972 may detect features of motion (i.e., one or more movements) of the user device 1905. For example, the motion sensor 1972 may include an accelerometer to detect acceleration, a gyroscope to detect angular velocity, a geomagnetic sensor to detect direction, a geolocation sensor to detect location, etc., or a combination thereof to detect motion of the user device 1905. In certain embodiments, the motion sensor 1972 may generate a detection signal that includes data representing the detected motion. For example, the motion sensor 1972 may determine a number of distinct movements in a motion (e.g., from start of the series of movements to the stop, within a predetermined time interval, etc.), a number of physical shocks on the user device 1905 (e.g., a jarring, hitting, etc., of the electronic device), a speed and/or acceleration of the motion (instantaneous and/or temporal), or other motion features. The detected motion features may be included in the generated detection signal. The detection signal may be transmitted, e.g., to the controller 1974, whereby further processing may be performed based on data included in the detection signal. The motion sensor 1972 can work in conjunction with a Global Positioning System (GPS) section 1979. The GPS section 1979 detects the present position of the user device 1905. The information of the present position detected by the GPS section 1979 is transmitted to the controller 1974. An antenna 1980 is connected to the GPS section 1979 for receiving and transmitting signals to and from a GPS satellite.

The user device 1905 may include a camera section 1973, which includes a lens and shutter for capturing photographs of the surroundings around the user device 1905. In an embodiment, the camera section 1973 captures surroundings of an opposite side of the user device 1905 from the user. The images of the captured photographs can be displayed on the display panel 1975. A memory section saves the captured photographs. The memory section may reside within the camera section 1973 or it may be part of the memory 1978. The camera section 1973 can be a separate feature attached to the user device 1905 or it can be a built-in camera feature. According to an embodiment, the camera section 1973 of the user device 1905 can be implemented in order to acquire a single image or a series of images of anatomy of a patient. For instance, the camera section 1973 of the user device 1905 can be used to capture a single image or a series of images of a head of a patient.

Further to the above, the camera section 1973 of the user device 1905 can include both 2D and 3D capacities. Under the flow diagram described with respect to FIG. 3A, the camera section 1973 can employ a high-resolution 2D camera. Under the flow diagram described with respect to FIG. 13A, the camera section 1973 can employ a structured light projector and image sensors to capture a structured light image of an anatomy (e.g., head) of a patient, the captured structured light image being a 3D surface of the anatomy of the patient.

In an embodiment, the memory 1978 can store instructions for executing the method of the present disclosure via a user interface of a software application, described in FIG. 18A through FIG. 18H. The user interface can be displayed via the touch panel 1976, the touch panel 1876 being formed integrally with the display 1975. The method of the present disclosure can be by performed responsive to user interaction with the user device 1905 via the user interface, the user interface being controlled by a processor executing the software application displayed on the touch panel 1976. In an embodiment, the memory 1978 can be a remote server in communication with the user device 1905 via the wireless communication processor 1966. Similar to the memory 1978 local to the user device 1905, the remote server can store instructions for executing the software application according to that which is described herein with reference to FIG. 18A and FIG. 18H.

According to an embodiment, each of the above-described processing sections can be a central processing unit such as a Xenon or Core processor from Intel of America or an Opteron processor from AMD of America, or may be other processor types that would be recognized by one of ordinary skill in the art. Alternatively, the processing sections may be implemented on an FPGA, ASIC, PLD or using discrete logic circuits, as one of ordinary skill in the art would recognize. Further, the processing sections may be implemented as multiple processors cooperatively working in parallel to perform the instructions of the inventive processes described above.

In an embodiment, certain aspects of the present disclosure, as described above, can be implemented via machine learning approaches. These approaches can be one of a variety of approaches that generate, for instance, a classifier, such approaches including, among others, support vector machines, Bayesian networks, regression algorithms, and artificial neural networks. Moreover, in an embodiment, machine learning approaches may be applied to whole images of anatomy of a patient in order to generate complex cranial parameters such as CI, CVA, and CVAI. For instance, deformities may be identified by application of a trained neural network to whole images of a section of anatomy of a patient, the trained neural network being able to classify images as normal or abnormal. The classifier may be trained according to a training database including normative anatomical shapes. In certain cases, the training database can be built from synthetic models (e.g. computer-generated models based on real patient data) of anatomical development and growth. Further, multiple training databases, and therefore trained classifiers, may be generated such that a diagnosis may be based on patient specific factors including, among others, age, ancestry, birth height and birth weight, clinical and behavioral parameters. In this way, as it relates to cranial applications, the trained neural network can diagnose, based only on an acquired image, a cranial condition of a head of a patient without the need for additional measurements. It can be appreciated that the acquired image, as applied to any anatomical feature, may be a 2D image or a 3D image, the corresponding trained neural network being a 2D neural network or a 3D neural network.

According to an embodiment of the present disclosure, however, machine learning approaches can be applied to obtain, for instance, the fundamental cranial parameters described herein. Accordingly, what follows is a description of neural network functionality, wherein the input may be one or more images of a head of a patient and the output may be a prediction of a cranial parameter, a cranial contour, a cranial abnormality, a bodily deformity, or the like.

Figure 20:
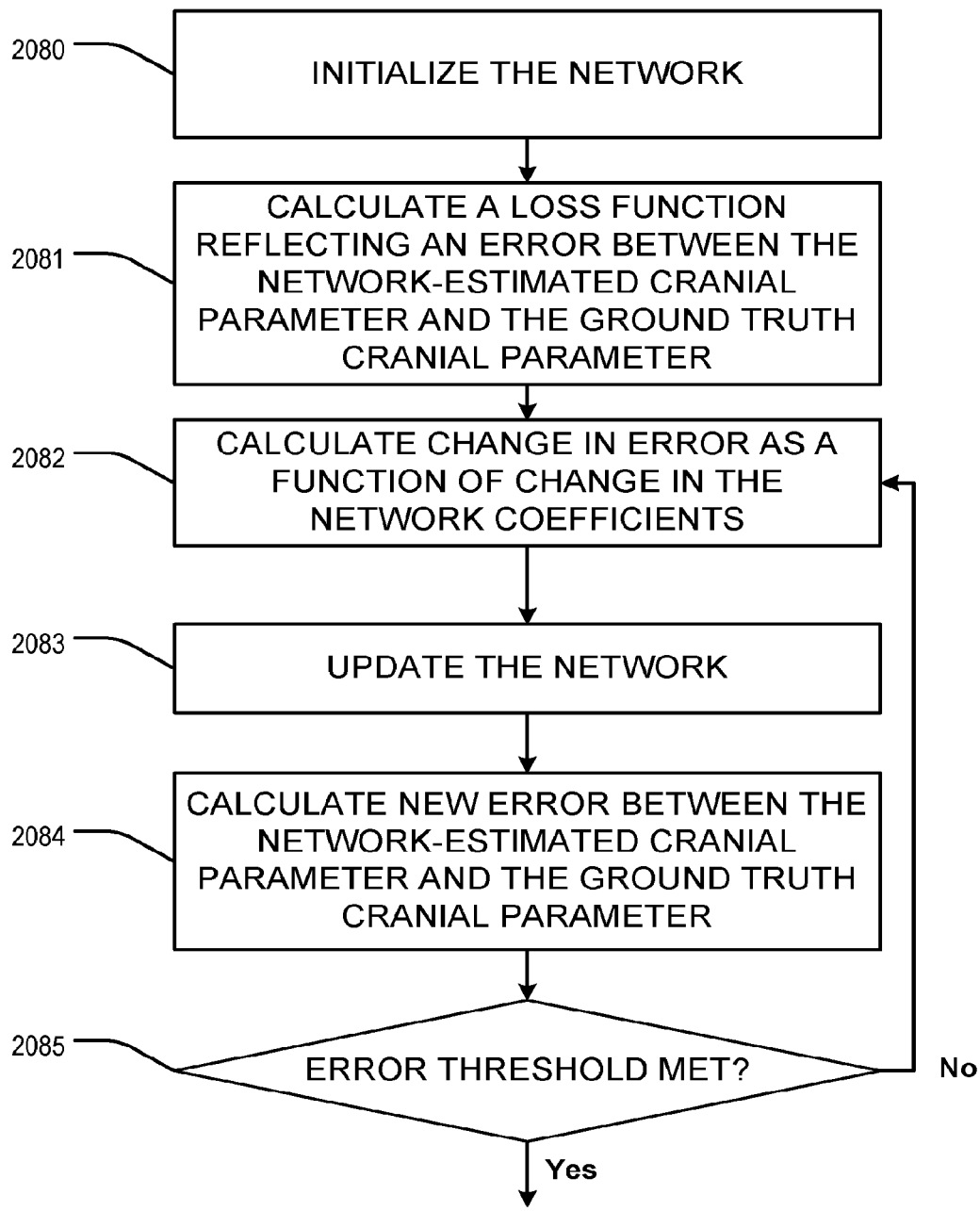
FIG. 20 is a flowchart of neural network training of the training phase of a method of deformity estimation, according to an exemplary embodiment of the present disclosure.

It should be appreciated that this description can be generalized, as would be understood by one of ordinary skill in the art. FIG. 20 is a flow diagram of one implementation of a training step performed in accordance with the present disclosure, and, for clarity, will be described in context of estimation of a cranial parameter.

As introduction, training a neural network model essentially means selecting one model from the set of allowed models (or, in a Bayesian framework, determining a distribution over the set of allowed models) that minimizes the cost criterion (i.e., the error value calculated using the cost function). Generally, a convolutional neural network (CNN) can be trained using any of numerous algorithms for training neural network models (e.g., by applying optimization theory and statistical estimation). In the present disclosure, the neural network will be referred to as a cranial-CNN (c-CNN).

For example, as related to the present disclosure, the optimization method used in training the c-CNN can use a form of gradient descent incorporating backpropagation to compute the actual gradients. This is done by taking the derivative of the cost function with respect to the network parameters and then changing those parameters in a gradient-related direction. The backpropagation training algorithm can be: a steepest descent method (e.g., with variable learning rate, with variable learning rate and momentum, and resilient backpropagation), a quasi-Newton method (e.g., Broyden-Fletcher-Goldfarb-Shanno, one step secant, and Levenberg-Marquardt), or a conjugate gradient method (e.g., Fletcher-Reeves update, Polak-Ribiére update, Powell-Beale restart, and scaled conjugate gradient). Additionally, evolutionary methods, such as gene expression programming, simulated annealing, expectation-maximization, non-parametric methods and particle swarm optimization, can also be used for training the c-CNN.

With reference again to FIG. 20, the flow diagram is a non-limiting example of an implementation of a training step for training the c-CNN using training data. The data in the training data can be from any of the training datasets, comprising a plurality of images of heads of patients, within the training database. In an embodiment, the plurality of images of heads of patients can be raw or segmented according to any number of pre-determined filters. In another embodiment, the plurality of images of heads of patients can be synthetic data generated by a processor and based upon a normal and abnormal head atlas.

In step 2080, an initial guess is generated for the coefficients of the c-CNN. For example, the initial guess can be based on a priori knowledge of the region of the head of the patient being imaged or one or more exemplary denoising methods, edge-detection methods, and/or blob detection methods. Additionally, the initial guess can be based on one of the LeCun initialization, an Xavier initialization, and a Kaiming initialization.

Step 2081 provides a non-limiting example of an optimization method for training the c-CNN. In step 2081, an error is calculated (e.g., using a loss function or a cost function) to represent a measure of the difference (e.g., a distance measure) between a ground truth cranial parameter and the output data of the c-CNN as applied in a current iteration of the c-CNN. The error can be calculated using any known cost function or distance measure between the image data, including those cost functions described above. Further, in certain implementations the error/loss function can be calculated using one or more of a hinge loss and a cross-entropy loss. In an example, the loss function can be defined as the mean square error between the output of the c-CNN ($P_{c\text{-}CNN}$) and the ground truth cranial parameter data ($P_{GT}$), or $$\frac{1}{n}\sum_{i=1}^{n} \|P_{GT} - P_{c\text{-}CNN}\|^2$$

where n is the number for the training object. As described above, this loss can be minimized using optimization methods including, among others, stochastic gradient descent.

Additionally, the loss function can be combined with a regularization approach to avoid overfitting the network to the particular instances represented in the training data. Regularization can help to prevent overfitting in machine learning problems. If trained too long, and assuming the model has enough representational power, the network will learn the noise specific to that dataset, which is referred to as overfitting. In case of overfitting, the c-CNN becomes a poor generalization, and the variance will be large because the noise varies between datasets. The minimum total error occurs when the sum of bias and variance are minimal. Accordingly, it is desirable to reach a local minimum that explains the data in the simplest possible way to maximize the likelihood that the trained network represents a general solution, rather than a solution particular to the noise in the training data. This goal can be achieved by, for example, early stopping, weight regularization, lasso regularization, ridge regularization, or elastic net regularization.

In certain implements the c-CNN is trained using backpropagation. Backpropagation can be used for training neural networks and is used in conjunction with gradient descent optimization methods. During a forward pass, the algorithm computes the network's predictions based on the current parameters $\Theta$. These predictions are then input into the loss function, by which they are compared to the corresponding ground truth labels. During the backward pass, the model computes the gradient of the loss function with respect to the current parameters, after which the parameters are updated by taking a step size of a predefined size in the direction of minimized loss (e.g., in accelerated methods, such that the Nesterov momentum method and various adaptive methods, the step size can be selected to more quickly converge to optimize the loss function.)

The optimization method by which the backprojection is performed can use one or more of gradient descent, batch gradient descent, stochastic gradient descent, and mini-batch stochastic gradient descent. Additionally, the optimization method can be accelerated using one or more momentum update techniques in the optimization approach that results in faster convergence rates of stochastic gradient descent in deep networks, including, e.g., Nesterov momentum technique or an adaptive method, such as Adagrad sub-gradient method, an Adadelta or RMSProp parameter update variation of the Adagrad method, and an Adam adaptive optimization technique. The optimization method can also apply a second order method by incorporating the Jacobian matrix into the update step.

The forward and backward passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to the non-limiting example shown in FIG. 20, step 2082 determines a change in the error as a function of the change in the network can be calculated (e.g., an error gradient) and this change in the error can be used to select a direction and step size for a subsequent change in the weights/coefficients of the c-CNN. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 2083, a new set of coefficients are determined for the c-CNN. For example, the weights/coefficients can be updated using the change calculated in step 2082, as in a gradient descent optimization method or an over-relaxation acceleration method.

In step 2084, a new error value is calculated using the updated weights/coefficients of the c-CNN.

In step 2085, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations are reached. When the stopping criteria is not satisfied the training process will continue back to the start of the iterative loop by returning and repeating step 2082 using the new weights and coefficients (the iterative loop includes steps 2082, 2083, 2084, and 2085). When the stopping criteria are satisfied, the training process is completed.

Figure 21:
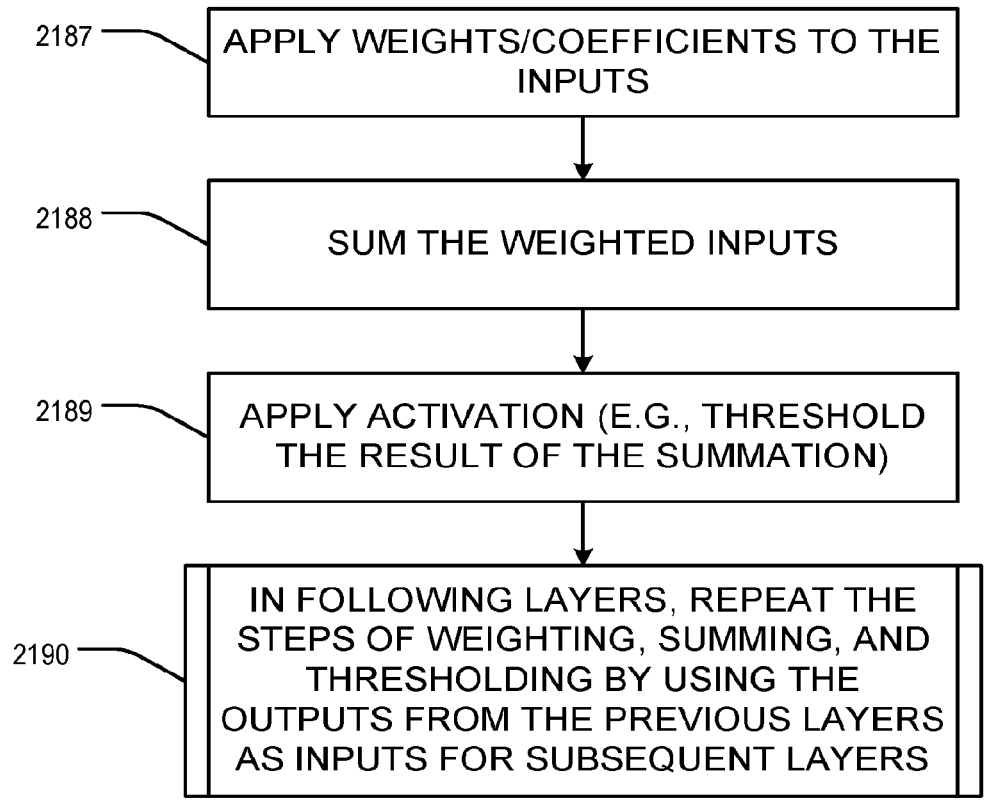
FIG. 21 is a generalized flowchart of implementation of an artificial neural network.
Figure 22:
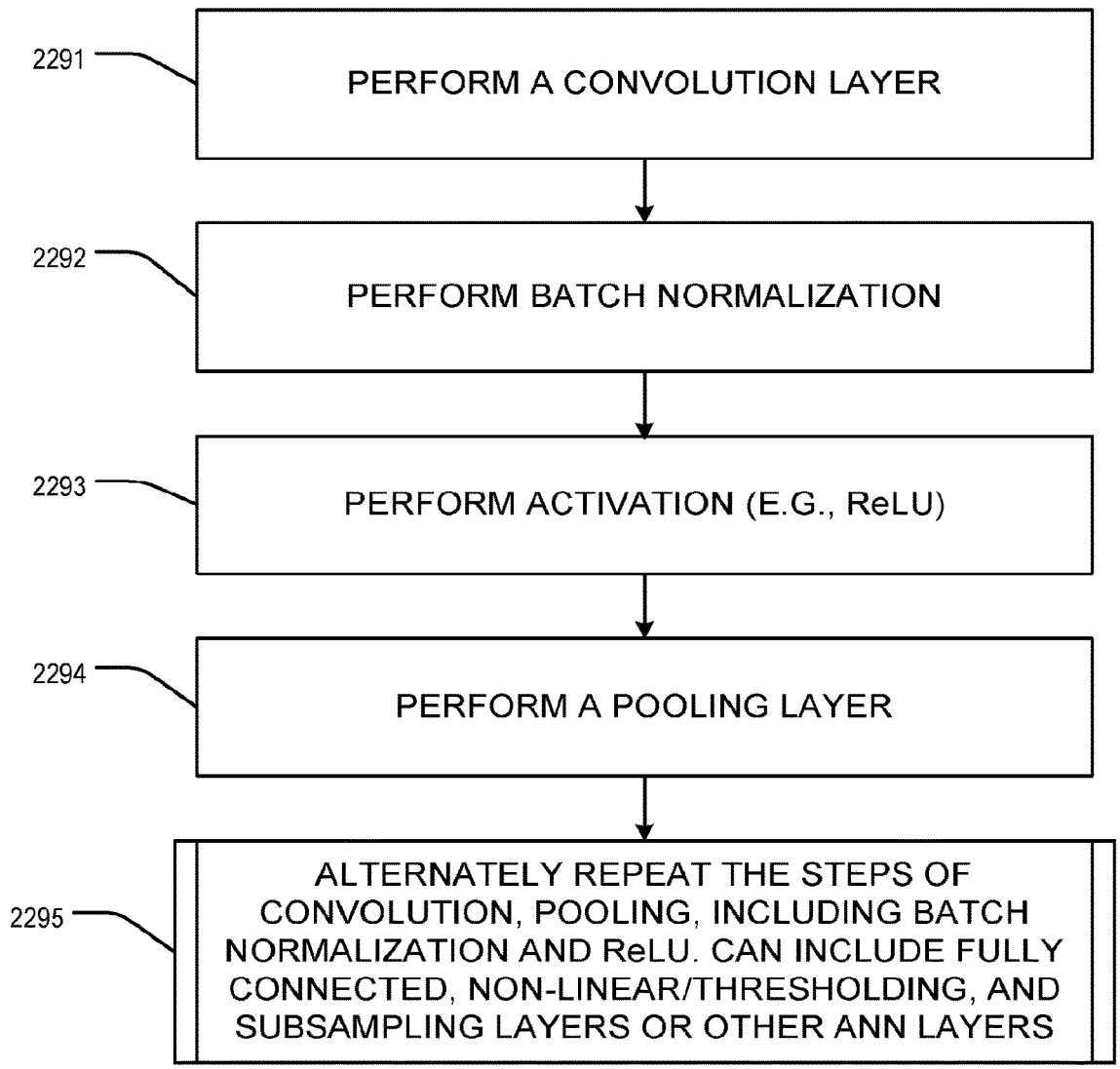
FIG. 22 is a flowchart of implementation of a convolutional neural network, according to an exemplary embodiment of the present disclosure.

FIG. 21 and FIG. 22 show flow diagrams of implementations of the training process. FIG. 21 is general for any type of layer in a feedforward artificial neural network (ANN), including, for example, fully connected layers, whereas FIG. 22 is specific to convolutional, pooling, batch normalization, and ReLU layers in a CNN. The c-CNN can include both fully connected layers and convolutional, pooling, batch normalization, and ReLU layers, resulting in a flow diagram that is a combination of FIG. 21 and FIG. 22, as would be understood by one of ordinary skill in the art. The implementations of the training process shown in FIG. 21 and FIG. 22 also correspond to applying the c-CNN to the respective data, or training images, of the training dataset.

In step 2187, the weights/coefficients corresponding to the connections between neurons (i.e., nodes) are applied to the respective inputs corresponding to, for example, the pixels of the training image.

In step 2188, the weighted inputs are summed. When the only non-zero weights/coefficients connecting to a given neuron on the next layer are regionally localized in an image represented in the previous layer, the combination of step 2187 and step 2188 is essentially identical to performing a convolution operation.

In step 2189, respective thresholds are applied to the weighted sums of the respective neurons.

In process 2190, the steps of weighting, summing, and thresholding are repeated for each of the subsequent layers.

FIG. 22 shows a flow diagram of another implementation of the training process. The implementation shown in FIG. 22 corresponds to operating on the training image at a hidden layer using a non-limiting implementation of the c-CNN.

In step 2291, the calculations for a convolution layer are performed as discussed in the foregoing and in accordance with the understanding of convolution layers of one of ordinary skill in the art.

In step 2292, following convolution, batch normalization can be performed to control for variation in the output of the previous layer, as would be understood by one of ordinary skill in the art.

In step 2293, following batch normalization, activation is performed according to the foregoing description of activation and in accordance with the understanding of activation of one of ordinary skill in the art. In an example, the activation function is a rectified activation function or, for example, a ReLU, as discussed above.

In another implementation, the ReLU layer of step 2293 may be performed prior to the batch normalization layer of step 2292.

In step 2294, the outputs from the convolution layer, following batch normalization and activation, are the inputs into a pooling layer that is performed according to the foregoing description of pooling layers and in accordance with the understanding of pooling layers of one of ordinary skill in the art.

In process 2295, the steps of a convolution layer, pooling layer, batch normalization layer, and ReLU layer can be repeated in whole or in part for a predefined number of layers. Following (or intermixed with) the above-described layers, the output from the ReLU layer can be fed to a predefined number of ANN layers that are performed according to the description provided for the ANN Layers in FIG. 21. The final output will be cranial parameter estimation.

Figure 23A:
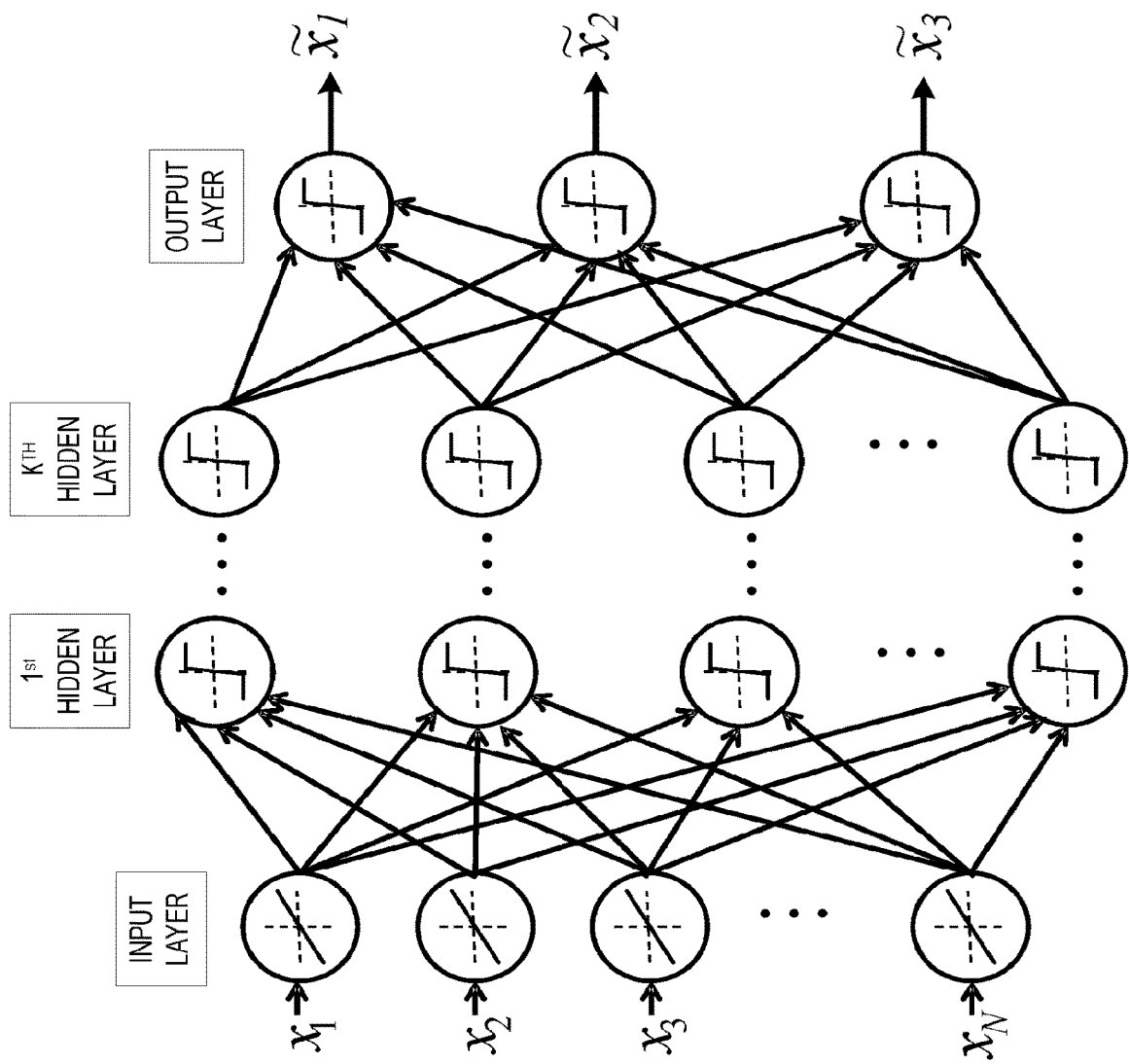
FIG. 23A is an example of a feedforward artificial neural network.
Figure 23B:
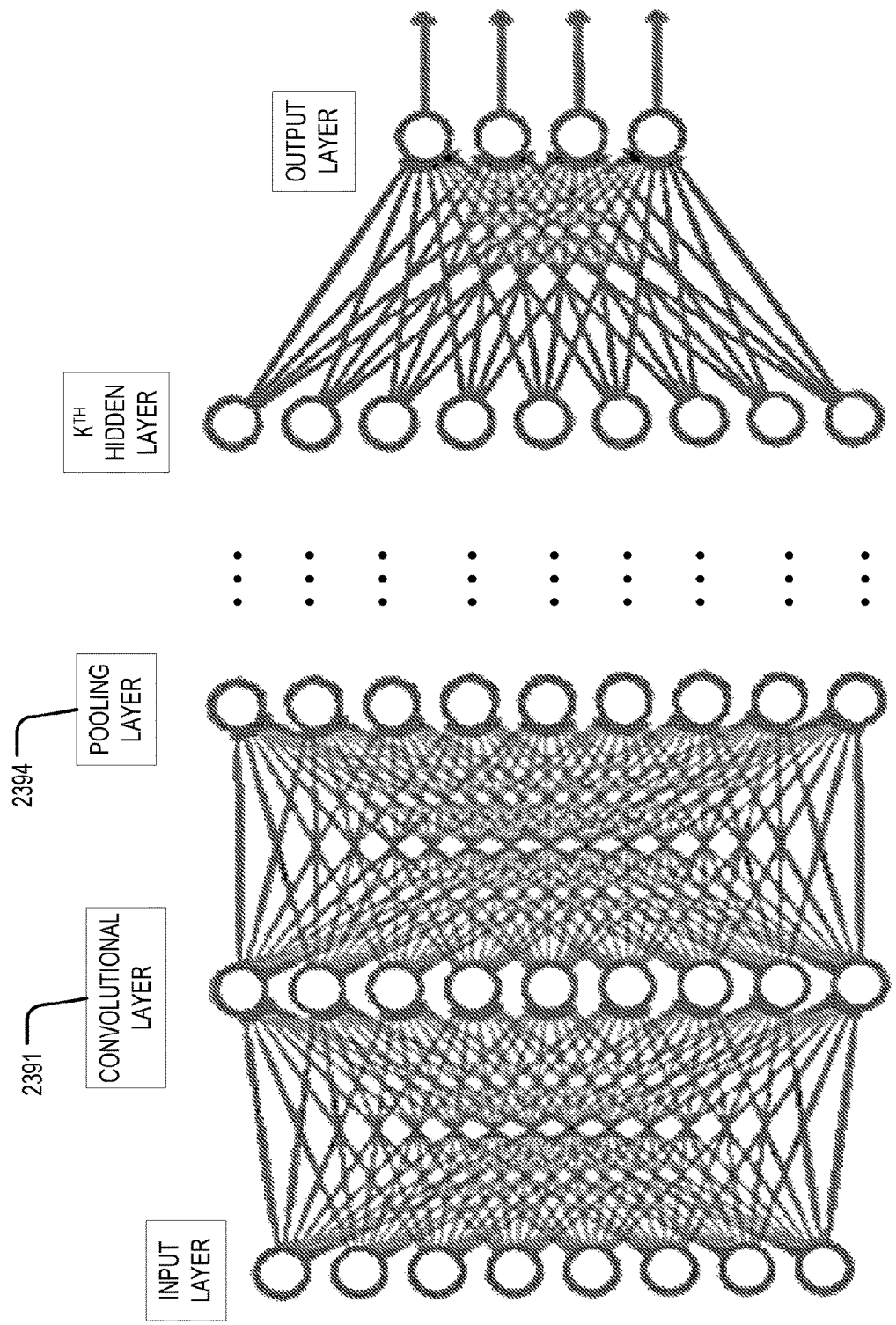
FIG. 23B is an example of a convolutional neural network, according to an embodiment of the present disclosure.

FIG. 23A and FIG. 23B show various examples of the inter-connections between layers in the c-CNN network. The c-CNN can include fully connected, convolutional, pooling, batch normalization, and activation layers, all of which are explained above and below. In certain preferred implementations of the c-CNN, convolutional layers are placed close to the input layer, whereas fully connected layers, which perform the high-level reasoning, are placed further down the architecture towards the loss function. Pooling layers can be inserted after convolutions and provide a reduction lowering the spatial extent of the filters, and thus the amount of learnable parameters. Batch normalization layers regulate gradient distractions to outliers and accelerate the learning process. Activation functions are also incorporated into various layers to introduce nonlinearity and enable the network to learn complex predictive relationships. The activation function can be a saturating activation function (e.g., a sigmoid or hyperbolic tangent activation function) or rectified activation function (e.g., ReLU discussed above).

FIG. 23A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers and is called an autoencoder. The c-CNN can have more than three layers of neurons and have as many output neurons as input neurons, wherein N is the number of, for example, pixels in the training image. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function $m(x)$ is defined as a composition of other functions $n_i(x)$, which can be further defined as a composition of other functions. This can be conveniently represented as a network structure, with arrows depicting the dependencies between variables, as shown in FIG. 23A and FIG. 23B. For example, the ANN can use a nonlinear weighted sum, wherein $m(x)=K(\Sigma_i w_i n_i(x))$ and where K (commonly referred to as the activation function) is some predefined function, such as the hyperbolic tangent.

In FIG. 23A (and similarly in FIG. 23B), the neurons (i.e., nodes) are depicted by circles around a threshold function. For the non-limiting example shown in FIG. 23A, the inputs are depicted as circles around a linear function and the arrows indicate directed communications between neurons. In certain implementations, the c-CNN is a feedforward network.

The c-CNN of the present disclosure operates to achieve a specific task, such as estimating a cranial parameter in a 2D or 3D image of a head, by searching within the class of functions F to learn, using a set of observations, to find $m^* \in F$, which solves the specific task in some optimal sense (e.g., the stopping criteria used in step 2085 discussed above). For example, in certain implementations, this can be achieved by defining a cost function $C:F \rightarrow m$ such that, for the optimal solution $m^*$, $C(m)^* \leq C(m) \forall m \in F$ (i.e., no solution has a cost less than the cost of the optimal solution). The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training data).

FIG. 23B shows a non-limiting example in which the c-CNN is a convolutional neural network (CNN). CNNs are a type of ANN that have beneficial properties for image processing and, therefore, have special relevancy for applications of image classification. CNNs use feed-forward ANNs in which the connectivity pattern between neurons can represent convolutions in image processing. For example, CNNs can be used for image-processing optimization by using multiple layers of small neuron collections which process portions of the input image, called receptive fields. The outputs of these collections can then be tiled so that they overlap to obtain a better representation of the original image. This processing pattern can be repeated over multiple layers having convolution and pooling layers, as shown, and can include batch normalization and activation layers.

As generally applied above, following after a convolution layer, a CNN can include local and/or global pooling layers which combine the outputs of neuron clusters in the convolution layers. Additionally, in certain implementations, the CNN can also include various combinations of convolutional and fully connected layers, with pointwise nonlinearity applied at the end of or after each layer.

CNNs have several advantages for image processing. To reduce the number of free parameters and improve generalization, a convolution operation on small regions of input is introduced. One significant advantage of certain implementations of CNNs is the use of shared weight in convolution layers, which means that the same filter (weights bank) is used as the coefficients for each pixel in the layer, both reducing memory footprint and improving performance. Compared to other image processing methods, CNNs advantageously use relatively little pre-processing. This means that the network is responsible for learning the filters that in traditional algorithms were hand-engineered. The lack of dependence on prior knowledge and human effort in designing features is a major advantage for CNNs.

The above-generalized machine learning framework can considered in view of the present disclosure. For instance, machine learning algorithms, such as neural networks, support vectors machines, random forests, regression models, and the like, can be used to analyze a 2D image or 3D image of the head or a 2D contour/3D mesh of the head extracted from an image. Head images with known diagnoses from real patients or from synthetically generated data (e.g. synthetically deformed 2D contours or 3D meshes from normal 2D contour and 3D meshes of a head) can be used for training. A trained machine learning approach, or classifier, can then output a class of the input, such as different types of FHS, including plagiocephaly, brachycephaly, and scaphocephaly, different types of craniosynostosis, including metopic, sagittal, coronal, and lambdoid, or degree of severity of the head malformation. The trained machine learning classifier can then be used to measure global shape metrics, such as CI/CVAI, CVA, head circumference, head volume, and local shape metrics, such as curvature measures. Measurement of such metrics over time may be used to enhance detection of other related conditions including hydrocephalus and torticollis. In case of torticollis, a customized questionnaire based on the head-growth patterns may be generated in order to obtain a more accurate diagnosis.

As related to craniosynostosis, specifically, different conditions manifests as different features. This is especially true with regard to 2D cranial contour. Therefore, subtle differences in head curvature in craniosynostosis, FHS, and normal head can be potentially captured by curvature features.

In one embodiment, a head cranial contour is divided into 5 segments. Given that FHS can be defined by 3 classes (plagiocephaly, brachycephaly, and scaphocephaly) and craniosynostosis can be defined by 5 classes (bi-coronal, uni-coronal, sagittal, metopic, and lambdoid), a combination thereof, including a normal condition, yields a class of 9 members. It can be appreciated that the number of class members is non-limiting and merely exemplary of a variety of class sizes suitable for such an application. For each class, shape parameters including mean bending energy and cubic spline parametrization of curve segments can be extracted and stored in a matrix. The matrix can be a matrix $C_{ijk}$ where i={1, ..., 9} and j can be the number of the features (e.g. if a $3^{rd}$ order spline is used to represent each segment of the cranial contour, j=5×4=20). k can be the number of training images available for each class. The distribution of $C_{mjk}$ and $C_{njk}$ (where m≠n) can then be compared to determine if the p-value is smaller than 0.001 (in other words, whether $C_{mjk}$ and $C_{njk}$ are statistically significantly different which means that each set of features have been able to differentiate class m from class n). Synthetic data representing how the head curve progresses into a deformed shape over time can then be generated, thereby creating temporal features. Such features may be able to efficiently model how the head shape may change over time.

In an embodiment, a machine learning approach including neural networks, support vector machines, random forests, regression models, and the like can be trained to use an image of a head of a patient or a cranial contour as an input with a type/severity of craniosynostosis (metopic, sagittal, etc.) as an output.

In an embodiment, a machine learning approach including neural networks, support vectors machines, random forests, regression models can be trained to use a 3D mesh of the head as an input and an type/severity of craniosynostosis (metopic, sagittal, etc.) an output.

Returning to the Figures, what follows is a visual description of certain body deformities and treatments thereof that have been discussed above.

Figure 24:
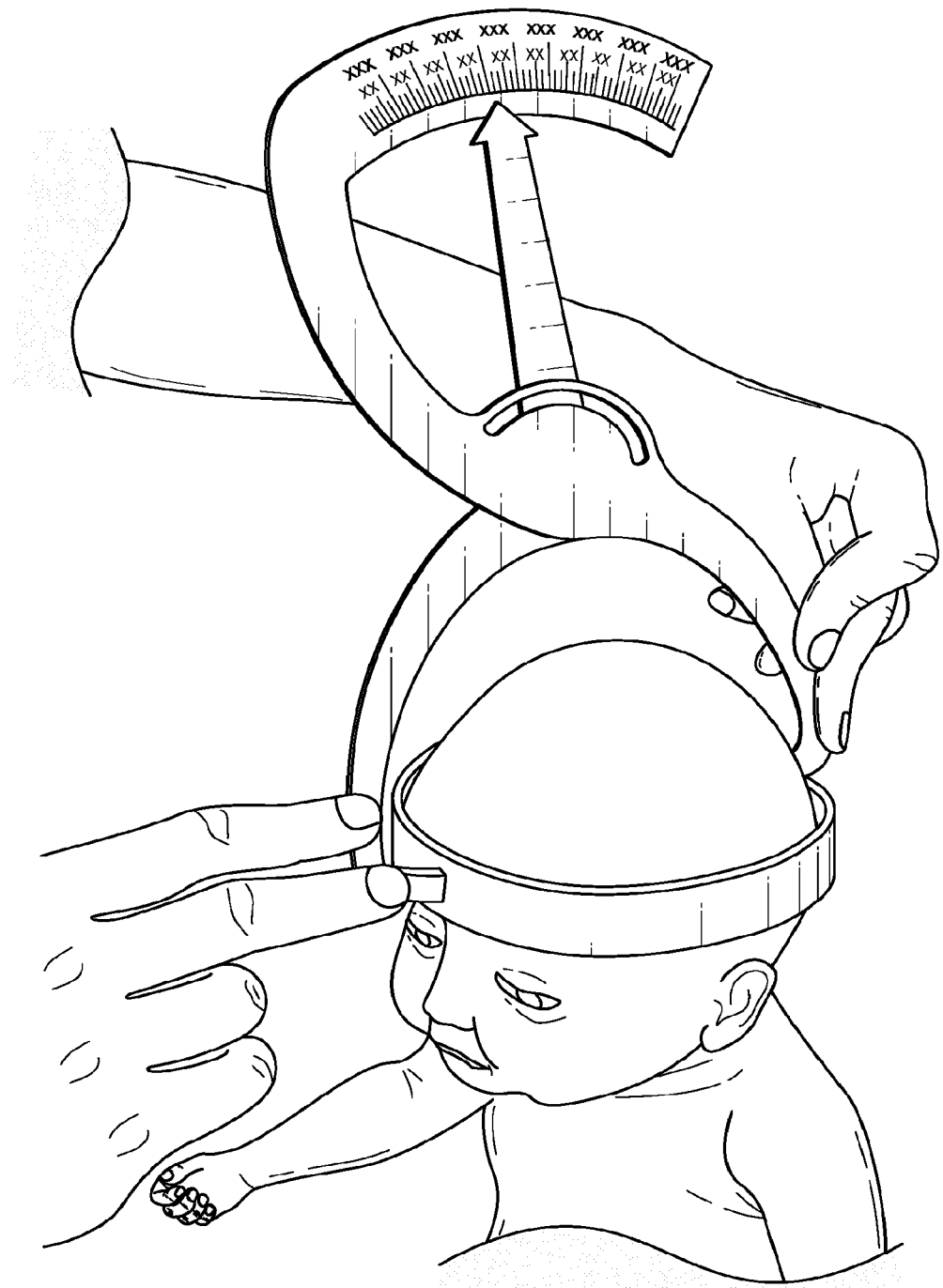
FIG. 24 is an image of a craniometer.

In an embodiment, FIG. 24 is an image of a craniometer used to determine head measurements and necessity for intervention.

Figure 25:
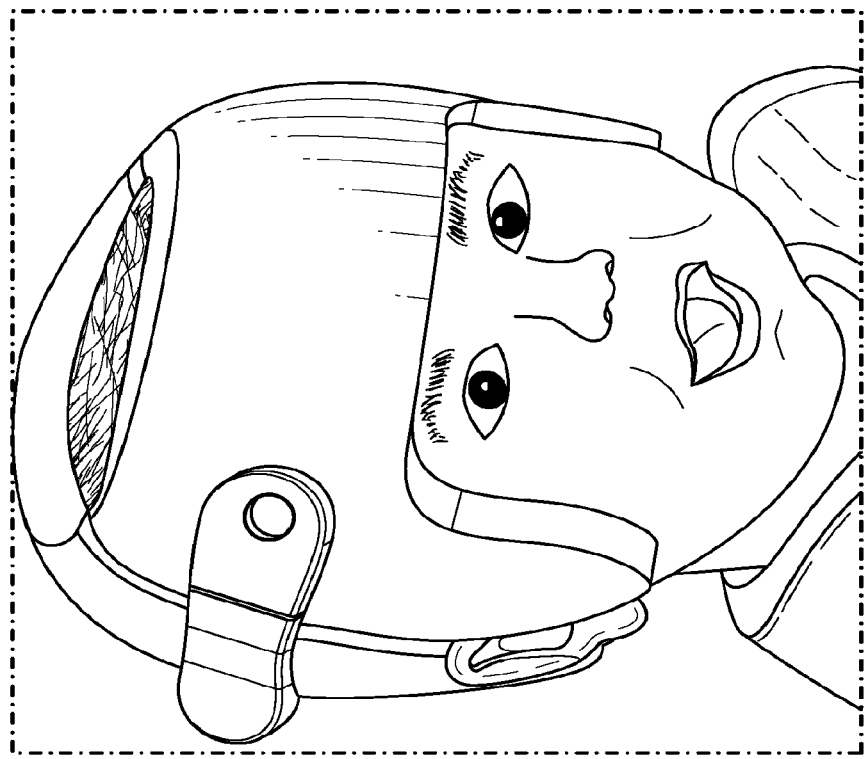
FIG. 25 is an image of a correctional helmet for flat head syndrome.

In an embodiment, FIG. 25 is an image of a correctional helmet for the treatment of FHS.

Figure 26A:
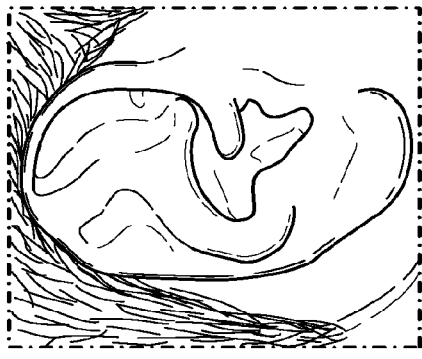
FIG. 26A is an image of an exemplary ear deformity.

In an embodiment, FIG. 26A is an image of a patient with Stahl's ear deformity, also known as Spock ear or elf ear. The transverse crux extends outwards from the antihelix and there is partial or full absence of a helical rim.

Figure 26B:
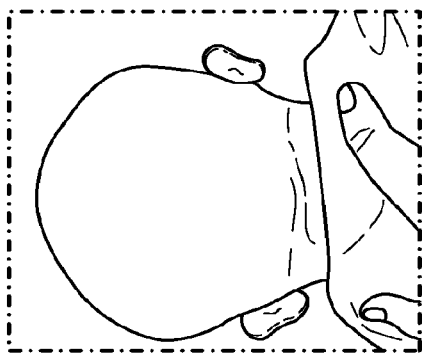
FIG. 26B is an image of an exemplary ear deformity.

In an embodiment, FIG. 26B is an image of a patient with prominent ear, also known as bat ear or Dumbo ear. In patients with prominent ear, the ears are over projected outwards.

Figure 26C:
FIG. 26C is an image of an exemplary ear deformity.

In an embodiment, FIG. 26C is an image of a patient with helical rim, wherein an irregular fold or outline along the edge of the helical rim is present.

Figure 26D:
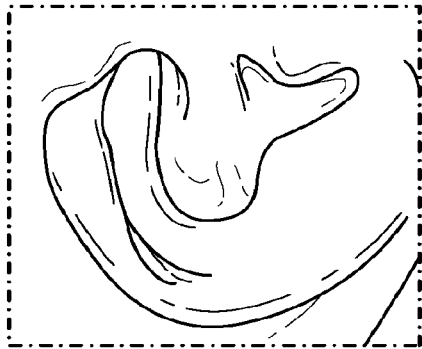
FIG. 26D is an image of an exemplary ear deformity.

In an embodiment, FIG. 26D is an image of a patient with cryptotia, wherein parts of the ear may appear buried beneath the skin with no apparent meeting point between the ear and the skull.

Figure 26E:
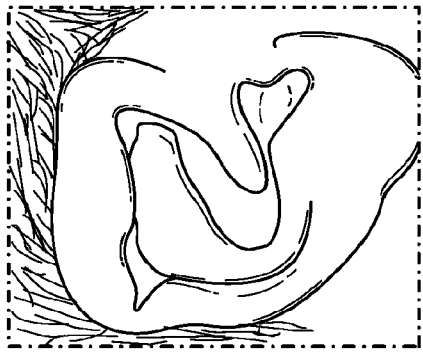
FIG. 26E is an image of an exemplary ear deformity.

In an embodiment, FIG. 26E is an image of a patient with lidding. In the case of lidding, the helical rim of the ear folds downwards on the upper part of the ear. In cases where the lidding is more severe, it is considered a lop ear.

Figure 26F:
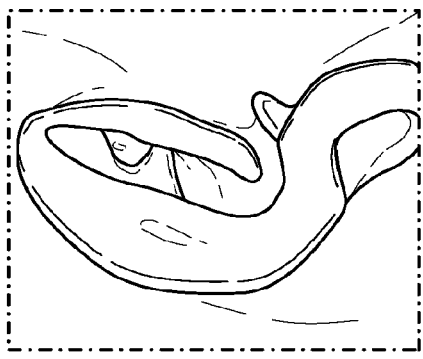
FIG. 26F is an image of an exemplary ear deformity.

In an embodiment, FIG. 26F is an image of a patient with a cup ear, a more pronounced form of prominent ear. In cup ear, the opening of the ears appears to be incomplete and the cartilage around the scapha is usually very stiff.

Figure 26G:
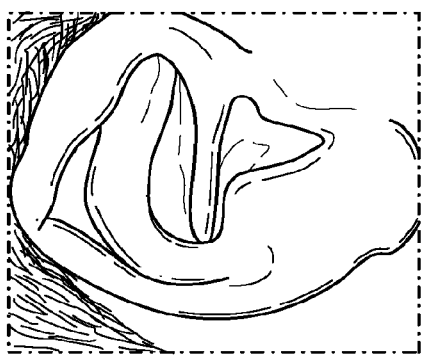
FIG. 26G is an image of an exemplary ear deformity.

In an embodiment, FIG. 26G is an image of a patient with conchal crus, wherein there exists folded cartilage that cuts across the mid portion of the ear.

Figure 26H:
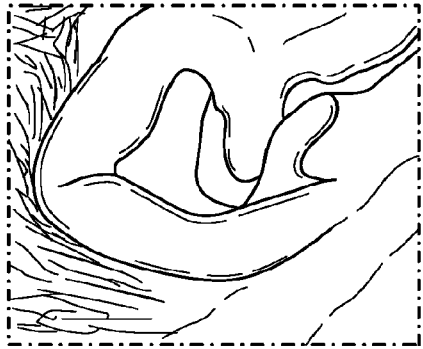
FIG. 26H is an image of an exemplary ear deformity.

In an embodiment, FIG. 26H is an image of a patient with a combination of deformities, wherein the patient has one or more instances of the above-described deformities.

Figure 27B:
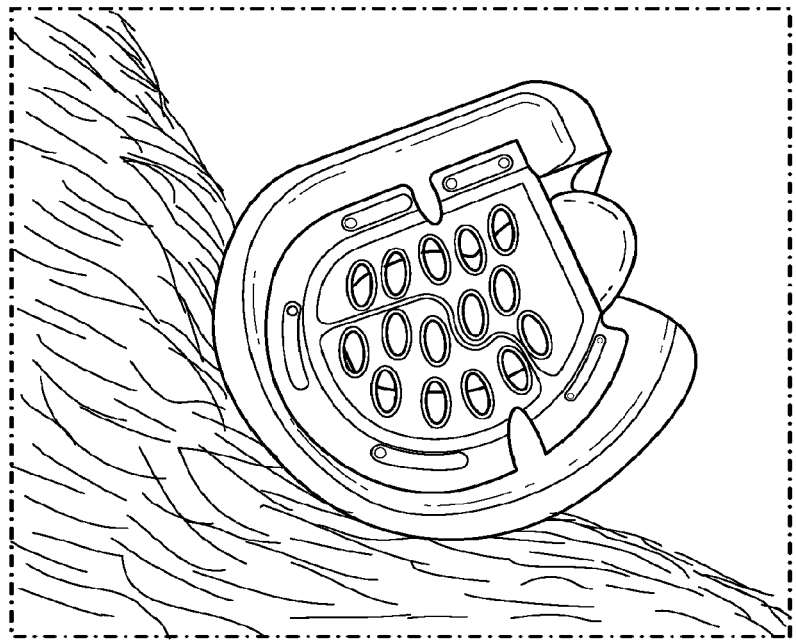
FIG. 27B is an image of an ear molding for treatment of an ear deformity.
Figure 27A:
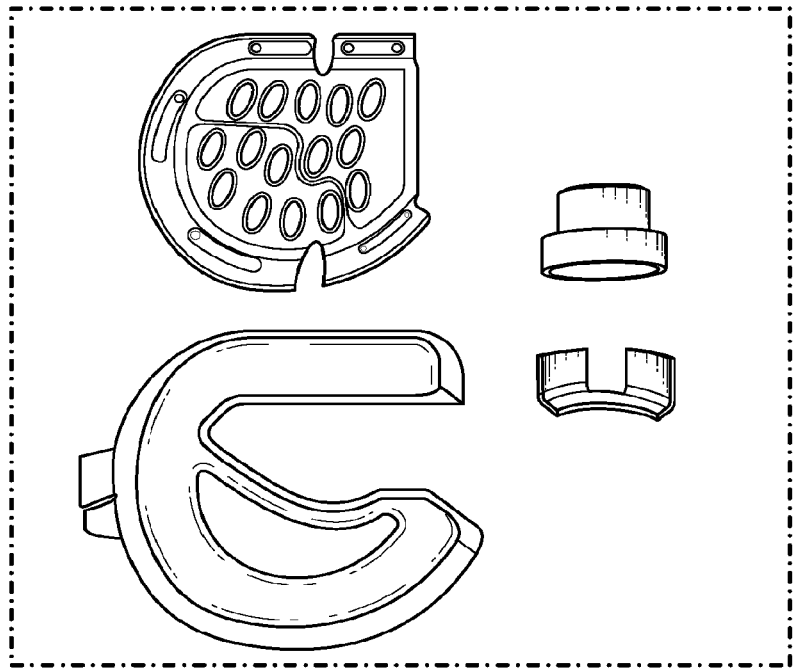
FIG. 27A is an image of an ear molding for treatment of an ear deformity.

In an embodiment, FIG. 27A is an image of an ear molding for treatment of an ear deformity, wherein each of the components is separated. The ear molding is a noninvasive method performed at pediatric offices when deformities are detected within 4 weeks of age. It is applicable in certain cases of ear deformities.

In an embodiment, FIG. 27B is an image of an ear molding for treatment of an ear deformity formed to the ear of a patient.

Figure 28A:
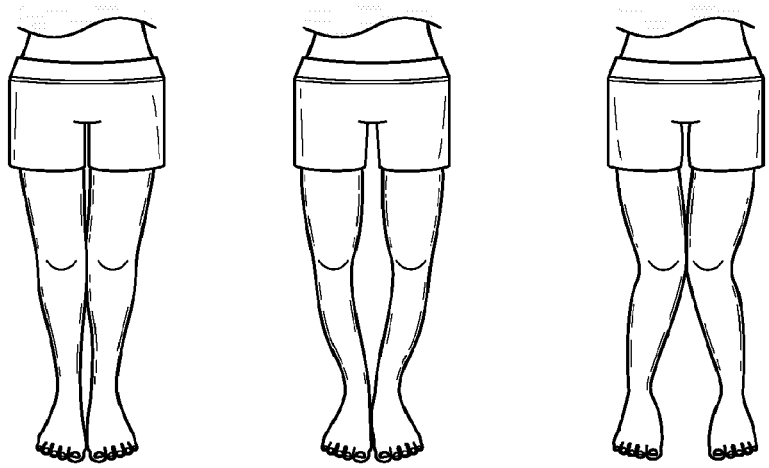
FIG. 28A is an image of an extremity deformity.

In an embodiment, FIG. 28A is a series of images of legs of a patient, wherein the legs are, from left to right, normal legs, bowed legs, and knock knee legs.

Figure 28B:
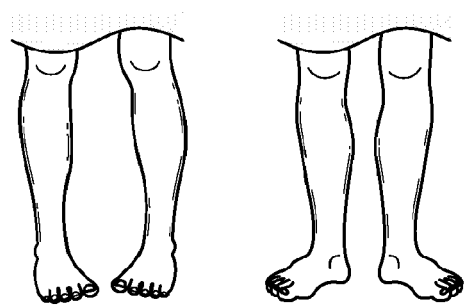
FIG. 28B is an image of an extremity deformity.

In an embodiment, FIG. 28B is a series of images of feet of a patient, wherein the feet of the patient are, from left to right, toe-in and toe-out.

Figure 28C:
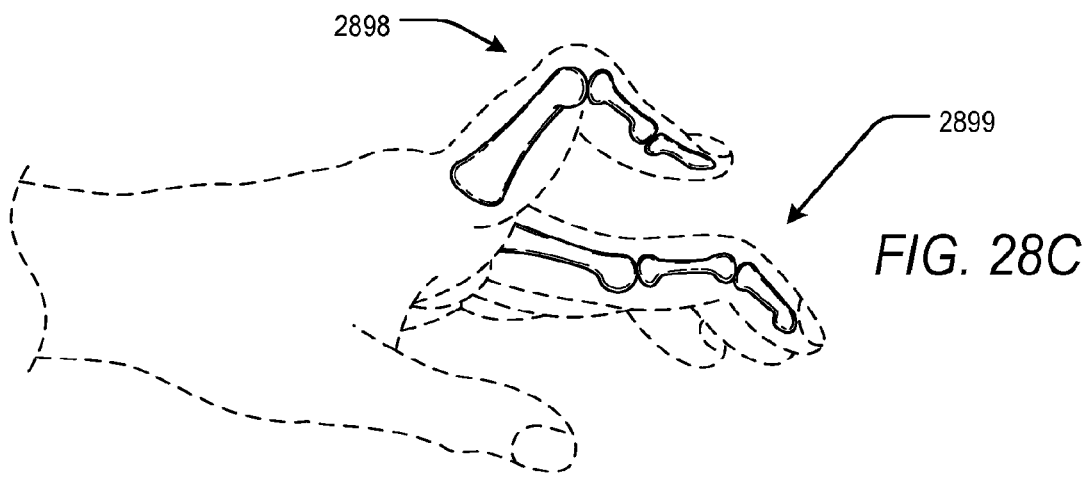
FIG. 28C is an image of an extremity deformity.

In an embodiment, FIG. 28C is an image of a hand of a patient, wherein the hand contains a Boutonniere deformity 2898 and a Swan-neck deformity 2899.

Embodiments of the present disclosure may also be as set forth in the following parenthetical s.

(1) A system, comprising an image sensor configured to acquire one or more images of a head of a patient, the head of the patient having a cranial shape, a display, and processing circuitry configured to receive the one or more images of the head of the patient, determine a cranial contour based on the received one or more images of the head of the patient, calculate at least one cranial parameter based on the determined cranial contour, the at least one cranial parameter being one selected from a group including cephalic index and cranial vault asymmetry index, compare the at least one cranial parameter to a pre-determined threshold of the at least one cranial parameter, and determine, based on the comparison, an abnormality of the cranial shape of the head of the patient.

(2) The system according to (1), wherein the processing circuitry is further configured to, during acquisition of the one or more images of the head of the patient by the image sensor, overlay an assistant feature on a live image being displayed on the display such that the acquired one or more images of the head of the patient, individually or combined, capture a cranial contour of the head of the patient.

(3) The system according to either (1) or (2), wherein the processing circuitry is further configured to determine the cranial contour by segmenting the head of the patient from a background.

(4) The system according to any of (1) to (3), wherein the processing circuitry is further configured to calculate the at least one cranial parameter by applying image analysis or machine learning to the segmented head of the patient to identify a landmark of a nose through which a nose direction is calculated.

(5) The system according to any of (1) to (4), wherein the processing circuitry is further configured to calculate the nose direction by determining a center of mass of the head of the patient.

(6) The system according to any of (1) to (5), wherein the processing circuitry is further configured to calculate the nose direction by determining a midpoint of a longest diagonal of the cranial contour.

(7) The system according to any of (1) to (6), wherein the one or more images of the head of the patient are acquired from a birds-eye view.

(8) The system according to any of (1) to (7), wherein the head of the patient is outfitted with a cap having a calibration marker.

(9) The system according to any of (1) to (8), wherein the one or more images of the head of the patient are acquired from at least one of a side-view, a front-view, and a back-view.

(10) A method, comprising receiving, by processing circuitry, one or more images of a head of a patient, the head of the patient having a cranial shape, determining, by the processing circuitry, a cranial contour based on the received one or more images of the head of the patient, calculating, by the processing circuitry, at least one cranial parameter based on the determined cranial contour, the at least one cranial parameter being one selected from a group including cephalic index and cranial vault asymmetry index, comparing, by the processing circuitry, the at least one cranial parameter to a pre-determined threshold of the at least one cranial parameter, and determining, based on the comparison and by the processing circuitry, an abnormality of a cranial shape of the head of the patient.

(11) The method according to (10), further comprising segmenting, by the processing circuitry, the head of the patient from a background, the head of the patient being covered by a cap having a calibration marker.

(12) The method according to either (10) or (11), further comprising applying, by the processing circuitry, image analysis or machine learning to the segmented head of the patient to identify a landmark of a nose through which a nose direction is calculated.

(13) The method according to any of (10) to (12), further comprising calculating the nose direction by determining a center of mass of the head of the patient.

(14) The method according to any of (10) to (13), further comprising calculating the nose direction by determining a midpoint of a longest diagonal of the cranial contour.

(15) A system, comprising an image sensor configured to acquire one or more images of a region of a body of a patient, a display, and processing circuitry configured to receive the one or more images of the region of the body of the patient, calculate at least one region parameter based on the received one or more images, determine, based on the at least one region parameter, an abnormality of the region of the body of the patient.

(16) The system according to (15), wherein the processing circuitry is further configured to, during acquisition of the one or more images of the region of the body of the patient by the image sensor, overlay an assistant feature on a live image being displayed on the display such that the acquired one or more images of the region of the body of the patient, individually or combined, capture a complete representation of the region of the body of the patient.

(17) The system according to (16), wherein the processing circuitry is further configured to segment the region of the body of the patient from a background.

(18) The system according to either (15) or (16), wherein the processing circuitry is further configured to calculate the at least one region parameter by applying image analysis or machine learning to the received one or more images of the region of the body of the patient.

(19) The system according to any of (15) to (18), wherein the processing circuitry is further configured to calculate the at least one region parameter by applying image analysis or machine learning to the segmented region of the body of the patient.

(20) The system according to any of (15) to (19), wherein the one or more images of the region of the body of the patient are acquired from a birds-eye view.

(21) The system according to any of (15) to (20), wherein the region of the body of the patient is outfitted with a calibration marker.

(22) The system according to any of (15) to (21), wherein the region of the body of the patient is one selected from a group including a facial skeleton, a cranium, an ear, a leg, a foot, a finger, a spine, and a vertebral body.

(23) The system according to any of (15) to (22), wherein the machine learning applied to the segmented region of the body of the patient is trained on a training database comprising real images of segmented regions of the body of the patient or computer-generated segmented regions of the body of the patient.

(24) The system according to any of (15) to (23), wherein the machine learning applied to the received one or more images of the region of the body of the patient is trained on a training database comprising real images of regions of the body of the patient or computer-generated regions of the body of the patient.

(25) A system, comprising an image sensor, a display, a touch screen panel, and processing circuitry implementing a user interface ("UI") by being configured to guide a user in acquiring, via the image sensor, one or more images of a region of a body of a patient, and display an evaluation of at least one parameter of the region of the body of the patient, the evaluation of the at least one parameter indicating whether the region of the body of the patient is abnormal, wherein the at least one parameter of the region of the body of the patient is calculated based on the acquired one or more images of the region of the body of the patient.

(26) The system according to (25), wherein the user is guided by verbal instructions output by an output device controlled by the processing circuitry.

(27) The system according to either (25) or (26), wherein the user is guided by a partial sphere augmented on the display during acquisition of the one or more images of the region of the body of the patient.

(28) The system according to any of (25) to (27), wherein the processing circuitry is further configured to generate an indicator when acquisition of the one or more images of the region of the body of the patient is complete.

(29) The system according to any of (25) to (28), wherein the processing circuitry implementing the UI is further configured to receive user input, via the touch screen panel, indicating landmarks of the region of the body of the patient.

(30) The system according to any of (25) to (29), wherein the processing circuitry implementing the UI is further configured to display the evaluation of the at least one parameter in context of one or more historical evaluations of the at least one parameter, the contextualized display of the evaluation of the at least one parameter indicating a trend of the at least one parameter.

(31) The system according to any of (25) to (30), wherein the processing circuitry implementing the UI is further configured to transmit the evaluation of the at least one parameter to a clinician.

(32) The system according to any of (25) to (31), wherein the processing circuitry implementing the UI is further configured to display a navigational map, the navigational map indicating a location of a clinician.

(33) The system according to any of (25) to (32), wherein the processing circuitry implementing the UI is further configured to display, based on the evaluation of the at least one parameter, one or more treatment options.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof.

Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A system, comprising:
an image sensor configured to acquire one or more images of a head of a patient, the head of the patient having a cranial shape;
a display; and
processing circuitry configured to
receive the one or more images of the head of the patient,
determine a cranial contour based on an appearance of a surface of the head of the patient in the received one or more images of the head of the patient, the cranial contour encompassing the head of the patient,
calculate at least one cranial parameter based on the determined cranial contour, the at least one cranial parameter being one selected from a group including cephalic index and cranial vault asymmetry index,
calculate a nose direction by determining a center of mass of the cranial contour, the nose direction being defined by a tip of a nose and the center of mass of the cranial contour,
compare the at least one cranial parameter to a pre-determined threshold of the at least one cranial parameter, and
determine, based on the comparison, an abnormality of the cranial shape of the head of the patient.

2. The system according to claim 1, wherein the processing circuitry is further configured to, during acquisition of the one or more images of the head of the patient by the image sensor, overlay an assistant feature on a live image being displayed on the display such that the acquired one or more images of the head of the patient, individually or combined, capture the cranial contour of the head of the patient.

3. The system according to claim 1, wherein the processing circuitry is further configured to determine the cranial contour by segmenting the head of the patient from a background.

4. The system according to claim 3, wherein the processing circuitry is further configured to calculate the at least one cranial parameter by applying image analysis or machine learning to the segmented head of the patient to identify a landmark of the nose through which the nose direction is calculated.

5. The system according to claim 1, wherein the one or more images of the head of the patient are acquired from a birds-eye view.

6. The system according to claim 1, wherein the head of the patient is outfitted with a cap having a calibration marker.

7. The system according to claim 1, wherein the one or more images of the head of the patient are acquired from at least one of a side-view, a front-view, and a back-view.

8. A method, comprising:
receiving, by processing circuitry, one or more images of a head of a patient, the head of the patient having a cranial shape;
determining, by the processing circuitry, a cranial contour based on an appearance of a surface of the head in the received one or more images of the head of the patient, the cranial contour encompassing the head of the patient;
calculating, by the processing circuitry, a nose direction by determining a center of mass of the cranial contour, the nose direction being defined by the center of mass and a tip of a nose;
calculating, by the processing circuitry, at least one cranial parameter based on the determined cranial contour, the at least one cranial parameter being one selected from a group including cephalic index, cranial vault asymmetry index, cranial vault asymmetry, cranial breadth, cranial length, intracranial volume, oblique right and left diagonals, oblique cranial minimum and maximum, local curvature, differences in cranial shape and size from normative values, cranial volume, and head circumference;
comparing, by the processing circuitry, the at least one cranial parameter to a pre-determined threshold of the at least one cranial parameter; and
determining, based on the comparison and by the processing circuitry, an abnormality of a cranial shape of the head of the patient.

9. The method according to claim 8, further comprising segmenting, by the processing circuitry, the head of the patient from a background, the head of the patient being covered by a cap having a calibration marker.

10. The method according to claim 9, further comprising applying, by the processing circuitry, image analysis or machine learning to the segmented head of the patient to identify a landmark of the nose through which the nose direction is calculated.

11. The method according to claim 8, further comprising calculating the nose direction by determining a midpoint of a longest diagonal of the cranial contour, the nose direction being defined by the midpoint of the longest diagonal of the cranial contour and the tip of the nose.

12. The method of claim 8, further comprising overlaying, during acquisition of the one or more images of the head of the patient by an image sensor, an assistant feature on a live image being displayed on a display such that the one or more images of the head of the patient, individually or combined, capture the cranial contour of the head of the patient.

13. A system, comprising:
an image sensor configured to acquire one or more images of a head of a patient, the head of the patient having a cranial shape;
a display; and
processing circuitry configured to:
receive the one or more images of the head of the patient,
determine a cranial contour based on the received one or more images of the head of the patient,
calculate at least one cranial parameter based on the determined cranial contour, the at least one cranial parameter being one selected from a group including cephalic index and cranial vault asymmetry index, cranial vault asymmetry, cranial breadth, cranial length, intracranial volume, oblique right and left diagonals, oblique cranial minimum and maximum, local curvature, differences in cranial shape and size from normative values, cranial volume, and head circumference,
compare the at least one cranial parameter to a pre-determined threshold of the at least one cranial parameter, and determine, based on the comparison, an abnormality of the cranial shape of the head of the patient, wherein the processing circuitry is further configured to calculate a nose direction by determining a center of mass of the cranial contour, the nose direction being defined by the center of mass of the cranial contour and a tip of a nose.

14. The system according to claim 13, wherein the processing circuitry is further configured to, during acquisition of the one or more images of the head of the patient by the image sensor, overlay an assistant feature on a live image being displayed on the display such that the acquired one or more images of the head of the patient, individually or combined, capture the cranial contour of the head of the patient.

15. The system according to claim 13, wherein the processing circuitry is further configured to determine the cranial contour by segmenting the head of the patient from a background.

16. The system according to claim 15, wherein the processing circuitry is further configured to calculate the at least one cranial parameter by applying image analysis or machine learning to the segmented head of the patient to identify a landmark of the nose through which the nose direction is calculated.

17. The system according to claim 13, wherein the one or more images of the head of the patient are acquired from a birds-eye view.

18. The system according to claim 13, wherein the head of the patient is outfitted with a cap having a calibration marker.

19. The system according to claim 13, wherein the one or more images of the head of the patient are acquired from at least one of a side-view, a front-view, and a back-view.

* * * * *